United States Patent
Lee et al.

(10) Patent No.: US 10,947,541 B2
(45) Date of Patent: *Mar. 16, 2021

(54) TREATMENT OF ATOPIC DERMATITIS AND ASTHMA USING RNA COMPLEXES THAT TARGET IL4Rα, TRPA1, OR F2RL1

(71) Applicant: OliX Pharmaceuticals, Inc., Gyeonggi-do (KR)

(72) Inventors: Dong-Ki Lee, Seoul (KR); Sun Woo Hong, Gyeonggi-do (KR); Hanna Lee, Seoul (KR); Dayeon Yu, Seoul (KR); Ji Eom, Seoul (KR)

(73) Assignee: OliX Pharmaceuticals, Inc., Gyeonggi-do (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/514,569

(22) Filed: Jul. 17, 2019

(65) Prior Publication Data

US 2020/0109405 A1    Apr. 9, 2020

Related U.S. Application Data

(63) Continuation of application No. 16/352,417, filed on Mar. 13, 2019, now abandoned, which is a continuation of application No. 15/422,186, filed on Feb. 1, 2017, now Pat. No. 10,358,648.

(60) Provisional application No. 62/290,298, filed on Feb. 2, 2016.

(51) Int. Cl.
C12N 15/113 (2010.01)

(52) U.S. Cl.
CPC ...... *C12N 15/1138* (2013.01); *C12N 2310/11* (2013.01); *C12N 2310/14* (2013.01); *C12N 2310/315* (2013.01); *C12N 2310/321* (2013.01); *C12N 2310/3515* (2013.01); *C12N 2310/3521* (2013.01)

(58) Field of Classification Search
None
See application file for complete search history.

(56) References Cited

U.S. PATENT DOCUMENTS

| | | | |
|---|---|---|---|
| 5,837,258 A | 11/1998 | Grotendorst | |
| 7,078,196 B2 | 7/2006 | Tuschl et al. | |
| 7,691,997 B2* | 4/2010 | Khvorova | C12N 15/113 536/24.5 |
| 7,700,541 B2 | 4/2010 | Tanaka et al. | |
| 8,410,260 B2 | 4/2013 | Collin-Djangone et al. | |
| 8,614,309 B2 | 12/2013 | Feinstein et al. | |
| 8,802,733 B2 | 8/2014 | Ganesan et al. | |
| 8,822,428 B2 | 9/2014 | Collin-Djangone et al. | |
| 8,980,273 B1 | 3/2015 | Clube | |
| 9,453,226 B2 | 9/2016 | Ambati et al. | |
| 9,637,742 B2 | 5/2017 | Lee | |
| 9,707,235 B1 | 7/2017 | Ambati | |
| 10,059,949 B2 | 8/2018 | Lee et al. | |
| 10,064,801 B2 | 9/2018 | Hong et al. | |
| 10,125,362 B2 | 11/2018 | Hong | |
| 10,214,744 B2 | 2/2019 | Lee | |
| 10,358,648 B2 | 7/2019 | Lee et al. | |
| 2004/0138163 A1 | 7/2004 | McSwiggen et al. | |
| 2004/0180351 A1 | 9/2004 | Giese et al. | |
| 2004/0266707 A1 | 12/2004 | Leake et al. | |
| 2005/0119202 A1 | 6/2005 | Kreutzer et al. | |
| 2005/0282188 A1 | 12/2005 | Haeberli et al. | |
| 2006/0069050 A1 | 3/2006 | Rana | |
| 2006/0094032 A1 | 5/2006 | Fougerolles et al. | |
| 2006/0105976 A1 | 5/2006 | Soutschek et al. | |
| 2006/0134787 A1 | 6/2006 | Zamore et al. | |
| 2006/0142228 A1 | 6/2006 | Ford et al. | |
| 2006/0160123 A1 | 7/2006 | Quay | |
| 2007/0218495 A1 | 9/2007 | Birmingham et al. | |
| 2007/0275914 A1 | 11/2007 | Manoharan et al. | |
| 2008/0125386 A1 | 5/2008 | Rana et al. | |
| 2008/0188430 A1 | 8/2008 | Usman et al. | |
| 2009/0004668 A1 | 1/2009 | Chen et al. | |
| 2009/0012022 A1 | 1/2009 | Milner et al. | |
| 2009/0130751 A1 | 5/2009 | Davidson et al. | |
| 2009/0191625 A1 | 7/2009 | Khvorova et al. | |
| 2009/0208564 A1 | 8/2009 | Li et al. | |
| 2010/0197023 A1 | 8/2010 | Leake et al. | |
| 2010/0254945 A1 | 10/2010 | Ge et al. | |
| 2010/0291681 A1 | 11/2010 | Khvorova et al. | |
| 2011/0028534 A1 | 2/2011 | Shepard et al. | |
| 2011/0054160 A1 | 3/2011 | Manoharan | |
| 2011/0237647 A1 | 9/2011 | Shirasawa et al. | |
| 2011/0237648 A1 | 9/2011 | Khvorova et al. | |

(Continued)

FOREIGN PATENT DOCUMENTS

| | | |
|---|---|---|
| CN | 102719432 | 10/2012 |
| EP | 2631291 | 8/2013 |

(Continued)

OTHER PUBLICATIONS

Yuan et al. (Human Gene Therapy 23:521-532 (2013).*
Shetty, Priya B., et al. "Variants in CXADR and F2RL1 are associated with blood pressure and obesity in African-Americans in regions identified through admixture mapping." Journal of hypertension 30.10 (2012): 1970.*
Ambati et al., "Mechanisms of Age-Related Macular Degeneration," Neuron, 75: 26-39 (2012).
Bhagwat et al., "Salmon and king crab tryspin stimulate interlukin-8 and matrix metalloproteinases via protease-activated receptor-2 in the sking keratinocytic HaCaT cell line," Food and Chemical Toxicology, vol. 69, Apr. 30, 2014, pp. 303-311.

(Continued)

*Primary Examiner* — Kimberly Chong
(74) *Attorney, Agent, or Firm* — Morgan, Lewis & Bockius LLP

(57) ABSTRACT

In certain aspects, provided herein are RNA complexes (e.g., asymmetric RNA complexes, such as asiRNAs or cell penetrating asiRNAs) that inhibit IL4Rα, TRPA1, and/or F2RL1 expression and are therefore useful for treating atopic dermatitis or asthma.

19 Claims, 41 Drawing Sheets

Specification includes a Sequence Listing.

(56) References Cited

U.S. PATENT DOCUMENTS

| | | |
|---|---|---|
| 2011/0251258 A1 | 10/2011 | Samarsky et al. |
| 2011/0263680 A1 | 10/2011 | Khvorova et al. |
| 2011/0269816 A1 | 11/2011 | Kaspar et al. |
| 2012/0016011 A1 | 1/2012 | Pickering et al. |
| 2012/0238017 A1 | 9/2012 | Lee et al. |
| 2013/0011922 A1 | 1/2013 | Quay et al. |
| 2013/0035368 A1 | 2/2013 | Avkin-Nachum et al. |
| 2013/0115613 A1 | 5/2013 | Madiraiu et al. |
| 2013/0123342 A1 | 5/2013 | Brown |
| 2013/0131142 A1 | 5/2013 | Libertine et al. |
| 2013/0190387 A1 | 7/2013 | Feinstein |
| 2013/0273657 A1 | 10/2013 | Lee |
| 2013/0317080 A1 | 11/2013 | Rajeev et al. |
| 2014/0094501 A1 | 4/2014 | Puri et al. |
| 2014/0227266 A1 | 8/2014 | Lee et al. |
| 2014/0249304 A1 | 9/2014 | Lee et al. |
| 2014/0328903 A1 | 11/2014 | Santel et al. |
| 2014/0350068 A1 | 11/2014 | Feinstein et al. |
| 2015/0111948 A1 | 4/2015 | Hong |
| 2015/0184163 A1 | 7/2015 | Wilson et al. |
| 2016/0017056 A1 | 1/2016 | Clube |
| 2016/0122764 A1 | 5/2016 | Chae et al. |
| 2016/0319278 A1 | 11/2016 | Khvorova et al. |
| 2017/0298358 A1 | 10/2017 | Lee et al. |
| 2017/0369882 A1* | 12/2017 | Khvorova ............ C12N 15/113 |

FOREIGN PATENT DOCUMENTS

| | | |
|---|---|---|
| JP | 2012502991 | 2/2012 |
| KR | 101207561 | 12/2012 |
| WO | WO0244321 | 6/2002 |
| WO | WO02055693 | 7/2002 |
| WO | WO2005062937 | 7/2005 |
| WO | WO2005079533 | 9/2005 |
| WO | WO2007002470 | 2/2007 |
| WO | WO2007128477 | 11/2007 |
| WO | WO2008109377 | 9/2008 |
| WO | WO2009020344 | 2/2009 |
| WO | WO2009029688 | 3/2009 |
| WO | WO2009029690 | 3/2009 |
| WO | WO2009078685 | 6/2009 |
| WO | WO2009105260 | 8/2009 |
| WO | WO2010033247 | 3/2010 |
| WO | WO2010090762 | 8/2010 |
| WO | WO201119887 | 9/2011 |
| WO | WO2012078536 | 6/2012 |
| WO | WO2012118911 | 9/2012 |
| WO | WO2014043291 | 3/2014 |
| WO | WO2015002513 | 1/2015 |
| WO | WO2015015498 | 2/2015 |
| WO | WO2015171641 | 11/2015 |
| WO | WO2017017523 | 2/2017 |
| WO | WO2017085550 | 5/2017 |
| WO | WO2017134525 | 8/2017 |
| WO | WO2017134526 | 8/2017 |
| WO | WO2017178883 | 8/2017 |
| WO | WO2018004284 | 1/2018 |
| WO | WO2018146557 | 8/2018 |

OTHER PUBLICATIONS

Bolcato-Bellemin et al., "Sticky overhangs enhance siRNA-mediated gene silencing," PNAS, vol. 104, No. 41, pp. 16050-16055 (2007).

Bramsen et al., "Improved silencing properties using small internally segmented interfering RNAs," Nucleic Acids Research, (2007), pp. 5886-5897, vol. 35.

Bushati et al., "MicroRNAs in Neurodegeneration," Current Opin Neurobiol, 18: 292-296 (2008).

Caplen et al., "Specific inhibition of gene expression by small double-stranded RNAs in invertebrate and vertebrate systems," Proc. Natl. Acad. Sci. USA, (2001), pp. 9742-9747, vol. 98, No. 17.

Chang et al., "Structural diversity repertoire of gene silencing small interfering RNAs," Nucleic acid therapeutics, (2011), 21(3), 125-131.

Chang et al., "The design, preparation, and evaluation of asymmetric small interfering RNA for specific gene silencing in mammalian cells." Methods Mol Biol. 2013; 942:135-52.

Chang et al., "Asymmetric shorter-duplex siRNA structures trigger efficient gene silencing with reduced nonsoecific effects," Mol Ther, (2009) vol. 17(4): 725-732.

Chiu et al., "siRNA Function in RNAi: A Chemical Modification Analysis," RNA, 9: 1034-1048 (2003).

Doench et al., "siRNAs Can Function as miRNAs," Gene Dev, 17(4): 438-442 (2003).

Doench et al., "Specificity of MicroRNA Target Selection in Translation Repression," Gene Dev, 18: 504-511 (2004).

Elbashir et al.,"Duplexes of 21-nucleotide RNAs mediate RNA interference in cultured mammalian cells," Nature, (2001), 411:494-498.

Elbashir et al., "Functional anatomy of siRNAs for mediating efficient RNAi in Drosophila melanogaster embryo lysate," The EMBO Journal, (2001), pp. 6877-6888, vol. 20, No. 23.

Fire, "RNA-triggered gene silencing," Trends in Genetics, (1999), vol. 15, No. 9, pp. 358-363.

Fire et al., "Potent and specific genetic interference by double-stranded RNA in Caenorhabditis elegans," Nature, (1998), pp. 806-811, vol. 391.

Grimm, "Small silencing RNAs: State of the art," Advanced Drug Delivery Reviews, 61: 672-703 (2009).

Hammond et al., "Post-Transcriptional Gene Silencing By Double-Stranded RNA," Nature Reviews Genetics, (2001), vol. 2: 110-119.

Hong et al., "Effect of the guide strand 3'-end structure on the gene-silencing potency of asymmetric siRNA," Biochemical Journal, (2014), 461(3): 427-434.

Huang et al., "Targeting the ANGPT-TIE2 Pathway in Malignancy," Nat Rev Cancer, 10: 575-585 (2010).

Hwang, "Development of Cell-Penetrating Asymmetric Interfering RNA Targeting Connective Tissue Growth Factor," Journal of Investigative Dermatology, (2016), 136(11), 2305-2313.

Jackson et al., "Expression Profiling Reveals Off-Target Gene Regulation by RNAi," Nat Biotechnol, 21: 635-637 (2003).

Jang et al., "Gene Delivery From Polymer Scaffolds for Tissue Engineering," Expert Rev Med Devic, 1(1): 127-138 (2004).

Jeong et al., "siRNA conjugate delivery systems," Bioconjugate Chem, 20:5-14 (2009).

Jo et al., "Selection and optimization of asymmetric siRNA targeting the human c-MET gene," Mol Cell, 32:(6) 543-548 (2011).

Joshi et al., "siRNA: novel therapeutics from functional genomics", Biotechnology and Genetic Enginnering Reviews (2014) vol. 30, No. 1, pp. 1-30.

Julovi et al., "Protease Activated Receptor-2 Mediates Activated Protein C-Induce Cutaneous Wound Healing via Inhibition of p38," American Journal of Pathology, vol. 179, np. 5, Nov. 1, 2011, pp. 2233-2242.

Kelly et al., "Cell Type-Specific Regulation of Angiogenic Growth Factor Gene Expression and Induction of Angiogenesis in Nonischemic Tissue by a Constitutively Active Form of Hypoxia-inducible Factor 1," Circ Res, 93: 1074-1081 (2003).

Kim et al., "Synthetic dsRNA Dicer substrates enhance RNAi potency and efficacy," Nature Biotechnology, 23: 222-226 (2005).

Kore et al., "Chemical modification of synthetic RNAi agents and in vivo delivery techniques," Curr Bioactive Compounds, 4:6-14 (2008).

Kubo et al., "Modified 27nt dsRNAs with Dramatically Enhanced Stability in Serum and Long-Term RNAi Activity," Oligonucleotides, 17:445-464 (2007).

Kulkarni et al., "Evidence of Off-Target Effects Associated with Long dsRNAs in Drosophila melanogaster Cell-Based Assays," Nat Methods, 3: 833-838 (2006).

Larsen et al., "Salmon tryspin stimulates the expression of interleukin-8 via protease-activated receptor-2," Toxicology and Applied Pharmacology, vol. 230, No. 3, Aug. 1, 2008, pp. 276-282.

Lee et al., "Asymmetric RNA Duplexes as Next Generation RNAi Inducers", Gene Silencing: Theory, Techniques and Applications, (2010), pp. 343-348.

(56) References Cited

OTHER PUBLICATIONS

Li et al., "Inhibition of connective tissue growth factor by siRNA prevents liver fibrosis in rats," The Journal of Gene Medicine, (2006), 8:889-900.
Lima et al., "Human Dicer Binds Short Single-strand and Double-strand RNA with High Affinity and Interacts with Different Regions of the Nucleic Acids," The Journal of Biological Chemistry (2009), 284:2535-2548.
Liu et al, "Human airway tryspin-like protease induces mucin5AC hypersection via a protease-activated receptor 2-meidated pathway in human airway epithelial cells," Archives of Biochemistry and Biophysics, vol. 535, No. 2, Apr. 19, 2013, pp. 234-240.
Luo et al., "Inhibition of Connective Tiss0.ue Growth Factor by Small Interfering RNA Prevents Renal Fibrosis in Rats Undergoing Chronic Allograft Nephropathy," Transplantation Proceedings, (2008), 40:2365-2369.
Marques et al., "A structural basis for discriminating between self and nonself double-stranded RNAs in mammalian cells," Nature Biotechnology, 24: 559-565 (2006).
Martinez et al., "Singe-Stranded Antisense siRNAs Guide Target RNA Cleavage in RNAi," Cell, 110: 563-574 (2002).
Opalinska et al., "Nucleic-acid Therapeutics: Basic Principles and Recent Applications," Nature Rev, 1 (7): 503-514 (2002).
Paroo et al., "Challenges for RNAi in vivo," Trends in Biotech, 22(8): 390-394 (2004).
Patel et al., "A Novel Protective Role for the Innate Immunity Toll-Like Receptor 3 (TLR3) in the Retina via Stat3," Mol Cell Neurosci, 63: 38-48 (2014).
Raouane et al., "Lipid conjugated oligonucleotides: a useful strategy for delivery," Bioconjugate Chem, 23:1091-104 (2012).
Rose et al., "Functional Polarity is Introduced by Dicer Processing of Short Substrate RNAs," Nucleic Acids Res, 33: 4140-4156 (2005).
Sano et al., "Effect of asymmetric terminal structures of short RNA duplexes on the RNA interference activity and strand selection," Nucleic Acids Research (2008), 36: 5812-5821.
Sharp et al., "RNA-interference-2001," Genes & Development, (2001), 15:485-490.
Sioud et al., "Cationic liposome-mediated delivery of siRNAs in adult mice," Biochem Biophys Res Commun. (Dec. 26, 2003); 312(4)1 220-5.
Sisco et al., "Antisense Inhibition of Connective Tissue Growth Factor (CTGF/CCN2) mRNA Limits Hypertrophic Scarring Without Affecting Wound Healing in Vivo," Wound Repair Regen, 16: 661-673 (2008).
Song et al., "The Crystal Structure of the Argonaute2 PAZ Domain Reveals an RNA Binding Motif in RNAi Effector Complexes," Nat Struct Biol, 10(12): 1026-1032 (2003).
Soutschek et al., "Therapeutic Silencing of an Endogenous Gene by Systemic Adminstration of Modified siRNAs," Nature, 432: 173-178 (2004).
Sun et al., "Asymmetric RNA duplexes mediate RNA interference in mammalian cells," Nature Biotechnology, 26: 1379-1382 (2008).
Ui-Tei et al., "Essential Notes Regarding the Design of Functional siRNAs for Efficient Mammalian RNAi," J Biomed Biotechnol, 2006; 2006(4):65052. doi: 10.1155/JBB/2006/65052.
Ui-Tei et al., "Guidelines for the selection of highly effective siRNA sequences for mammalian and chick RNA interference," (2004), Nucleic Acids Research, vol. 32, pp. 936-948.
Vasdudevan et al., "Switching from Repression to Activation: MicroRNAs Can Up-Regulate Translation," Science, 318: 1931-1934 (2007).
Wang et al., "Nucleation, Propagation and Cleavage of Target RNAs in Ago Silencing Complexes," Nature, 461: 754-762 (2009).
Yang et al., "HENI recognizes 21-24 nt small RNA duplexes and deposits a methyl group onto the 2' OH of the 3' terminal nucleotide," Nucleic Acids Research, 34: 667-675 (2006).
Yuan et al., "Asymmetric siRNA: New Strategy to Improve Specificity and Reduce Off-Target Gene Expression", Human Gene Therapy 23:521-532 (2013).
Zamore, "RNA interference: listening to the sound of silence," Nature Structural Biology, (2001), 8(9):746-750.

* cited by examiner

Figure 1
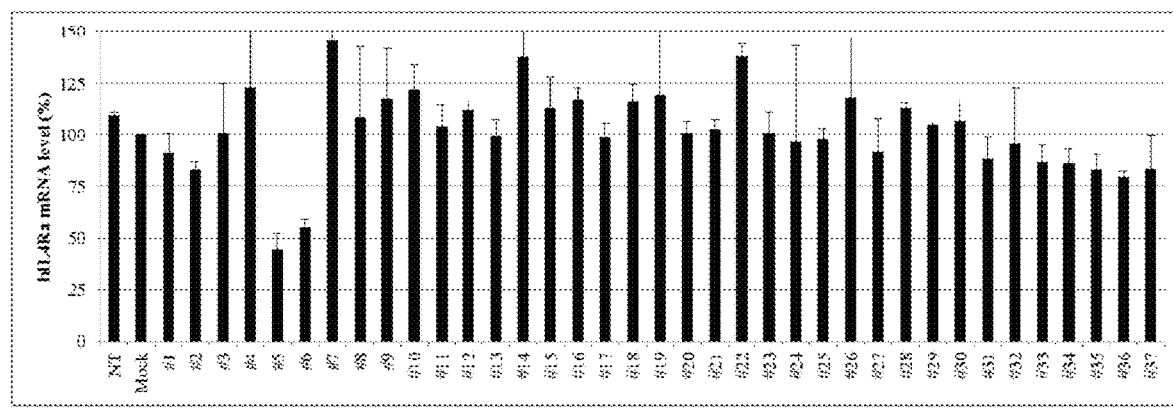
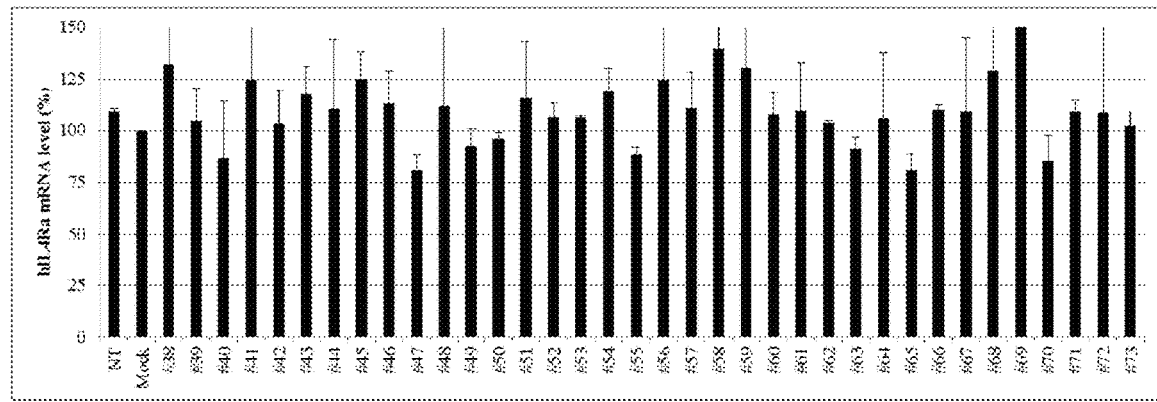

Figure 8

Human IL4Ra mRNA sequence (NM_000418.3).

```
   1 gggtctccgc gcccaggaaa gccccgcgcg gcgcgggcca gggaagggcc acccaggggt
  61 cccccacttc ccgcttgggc gcccggacgg cgaatggagc aggggcgcgc agataattaa
 121 agatttacac acagctggaa gaaatcatag agaagccggg cgtggtggct catgcctata
 181 atcccagcac ttttggaggc tgaggcgggc agatcacttg agatcaggag ttcgagacca
 241 gcctggtgcc ttggcatctc ccaatggggt ggctttgctc tgggctcctg ttccctgtga
 301 gctgcctggt cctgctgcag gtggcaagct ctgggaacat gaaggtcttg caggagccca
 361 cctgcgtctc cgactacatg agcatctcta cttgcgagtg gaagatgaat ggtcccacca
 421 attgcagcac cgagctccgc ctgttgtacc agctggtttt tctgctctcc gaagcccaca
 481 cgtgtatccc tgagaacaac ggaggcgcgg ggtgcgtgtg ccacctgctc atggatgacg
 541 tggtcagtgc ggataactat acactggacc tgtgggctgg gcagcagctg ctgtggaagg
 601 gctccttcaa gcccagcgag catgtgaaac cagggccccc aggaaacctg acagttcaca
 661 ccaatgtctc cgacactctg ctgctgacct ggagcaaccc gtatccccct gacaattacc
 721 tgtataatca tctcacctat gcagtcaaca tttggagtga aaacgacccg gcagatttca
 781 gaatctataa cgtgacctac ctagaaccct cctccgcat cgcagccagc accctgaagt
 841 ctgggatttc ctacagggca cgggtgaggg cctgggctca gtgctataac accacctgga
 901 gtgagtggag ccccagcacc aagtggcaca actcctacag ggagcccttc gagcagcacc
 961 tcctgctggg cgtcagcgtt tcctgcattg tcatcctggc cgtctgcctg ttgtgctatg
1021 tcagcatcac caagattaag aaagaatggt gggatcagat tcccaaccca gcccgcagcc
1081 gcctcgtggc tataataatc caggatgctc aggggtcaca gtgggagaag cggtcccgag
1141 gccaggaacc agccaagtgc ccacactgga agaattgtct taccaagctc ttgccctgtt
1201 ttctggagca caacatgaaa agggatgaag atcctcacaa ggctgccaaa gagatgcctt
1261 tccagggctc tggaaaatca gcatggtgcc cagtggagat cagcaagaca gtcctctggc
1321 cagagagcat cagcgtggtg cgatgtgtgg agttgtttga ggccccggtg gagtgtgagg
1381 aggaggagga ggtagaggaa gaaaaaggga gcttctgtgc atcgcctgag agcagcaggg
1441 atgacttcca ggagggaagg gagggcattg tggcccggct aacagagagc ctgttcctgg
1501 acctgctcgg agaggagaat gggggctttt gccagcagga catgggggag tcatgccttc
1561 ttccaccttc gggaagtacg agtgctcaca tgccctggga tgagttccca agtgcagggc
1621 ccaaggaggc acctccctgg ggcaaggagc agcctctcca cctggagcca agtcctcctg
1681 ccagcccgac ccagagtcca gacaacctga cttgcacaga gacgccctc gtcatcgcag
```

Figure 8 (Continued)

1741 gcaaccctgc ttaccgcagc ttcagcaact ccctgagcca gtcaccgtgt cccagagagc 1801 tgggtccaga cccactgctg gccagacacc tggaggaagt agaacccgag atgccctgtg 1861 tcccccagct ctctgagcca accactgtgc cccaacctga gccagaaacc tgggagcaga 1921 tcctccgccg aaatgtcctc cagcatgggg cagctgcagc ccccgtctcg gcccccacca 1981 gtggctatca ggagtttgta catgcggtgg agcagggtgg cacccaggcc agtgcggtgg 2041 tgggcttggg tcccccagga gaggctggtt acaaggcctt ctcaagcctg cttgccagca 2101 gtgctgtgtc cccagagaaa tgtgggtttg gggctagcag tggggaagag gggtataagc 2161 ctttccaaga cctcattcct ggctgccctg gggaccctgc cccagtccct gtcccttgt 2221 tcacctttgg actggacagg gagccacctc gcagtccgca gagctcacat ctcccaagca 2281 gctccccaga gcacctgggt ctggagccgg gggaaaaggt agaggacatg ccaaagcccc 2341 cacttcccca ggagcaggcc acagaccccc ttgtggacag cctgggcagt ggcattgtct 2401 actcagccct tacctgccac ctgtgcggcc acctgaaaca gtgtcatggc caggaggatg 2461 gtggccagac ccctgtcatg gccagtcctt gctgtggctg ctgctgtgga gacaggtcct 2521 cgcccccctac aaccccctg agggccccag acccctctcc aggtgggggtt ccactggagg 2581 ccagtctgtg tccggcctcc ctggcaccct cgggcatctc agagaagagt aaatcctcat 2641 catccttcca tcctgcccct ggcaatgctc agagctcaag ccagaccccc aaaatcgtga 2701 actttgtctc cgtgggaccc acatacatga gggtctctta ggtgcatgtc ctcttgttgc 2761 tgagtctgca gatgaggact agggcttatc catgcctggg aaatgccacc tcctggaagg 2821 cagccaggct ggcagatttc caaaagactt gaagaaccat ggtatgaagg tgattggccc 2881 cactgacgtt ggcctaacac tgggctgcag agactggacc ccgcccagca ttgggctggg 2941 ctcgccacat cccatgagag tagagggcac tgggtcgccg tgccccacgg caggcccctg 3001 caggaaaact gaggcccttg ggcacctcga cttgtgaacg agttgttggc tgctccctcc 3061 acagcttctg cagcagactg tccctgttgt aactgcccaa ggcatgtttt gccaccaga 3121 tcatggccca cgtggaggcc cacctgcctc tgtctcactg aactagaagc cgagcctaga 3181 aactaacaca gccatcaagg gaatgacttg ggcggccttg ggaaatcgat gagaaattga 3241 acttcaggga gggtggtcat tgcctagagg tgctcattca tttaacagag cttccttagg 3301 ttgatgctgg aggcagaatc ccggctgtca aggggtgttc agttaagggg agcaacagag 3361 gacatgaaaa attgctatga ctaaagcagg gacaatttgc tgccaaacac ccatgcccag 3421 ctgtatggct gggggctcct cgtatgcatg gaaccccag aataaatatg ctcagccacc 3481 ctgtgggccg ggcaatccag acagcaggca taaggcacca gttaccctgc atgttggccc

Figure 8 (Continued)

3541 agacctcagg tgctagggaa ggcgggaacc ttgggttgag taatgctcgt ctgtgtgttt
    3601 tagtttcatc acctgttatc tgtgtttgct gaggagagtg gaacagaagg ggtggagttt
    3661 tgtataaata aagtttcttt gtctctttaa aaaaaaaaaa aaaaaaaaa Figure 9
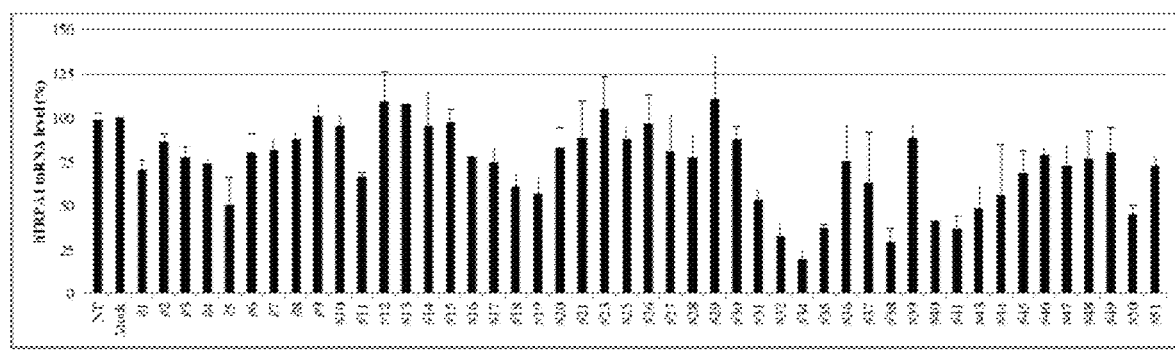
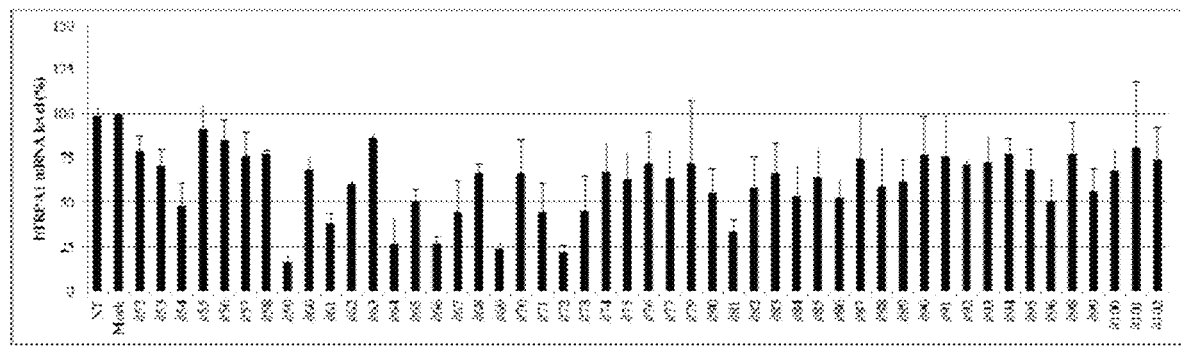

Figure 15
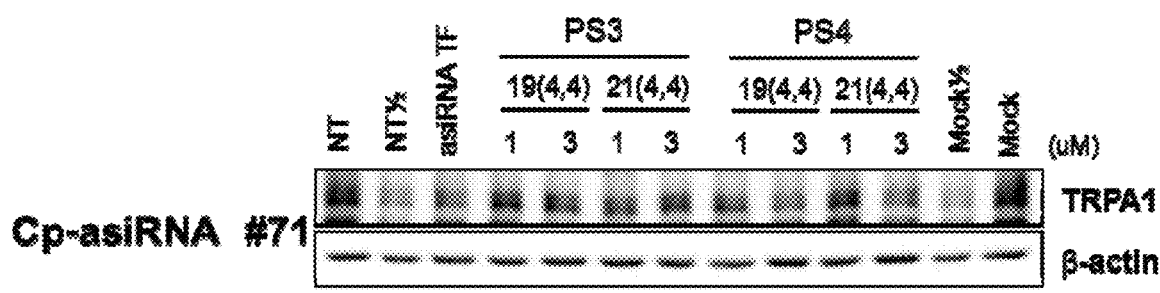
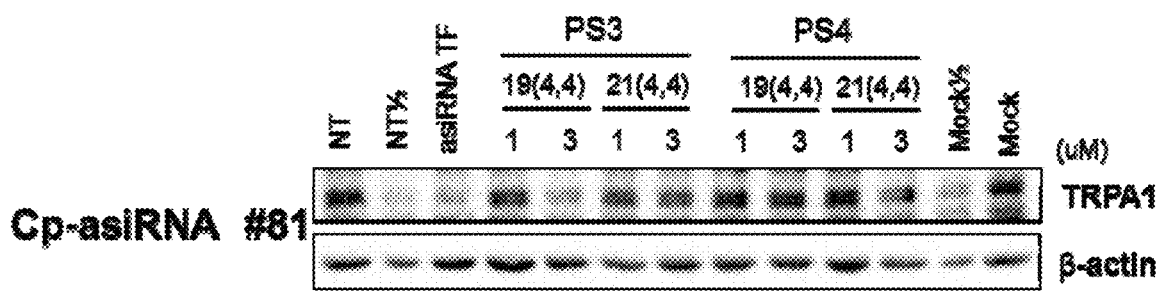

Figure 17

Human TRPA1 mRNA sequence (NM_007332)

```
   1 ccagaagttc tccagggctt ccgcagagcg acttttcgc tgcctgtgag ctgcagcgcg
  61 ggagagctcg ggctcgcgcg gaccccagcg cctggcaggc tgacagcgct ctctcgcccc
 121 aggtgcccgc gcgcgtggtg agcagctgca ccaggtggcg tccggggtgg ggtcaatgaa
 181 gcgcagcctg aggaagatgt ggcgccctgg agaaaagaag gagccccagg gcgttgtcta
 241 tgaggatgtg ccggacgaca cggaggattt caaggaatcg cttaaggtgg ttttgaagg
 301 aagtgcatat ggattacaaa actttaataa gcaaaagaaa ttaaaaagat gtgacgatat
 361 ggacaccttc ttcttgcatt atgctgcagc agaaggccaa attgagctaa tggagaagat
 421 caccagagat tcctctttgg aagtgctgca tgaaatggat gattatggaa atacccctct
 481 gcattgtgct gtagaaaaaa accaaattga aagcgttaag tttcttctca gcagaggagc
 541 aaacccaaat ctccgaaact tcaacatgat ggctcctctc cacatagctg tgcagggcat
 601 gaataatgag gtgatgaagg tcttgcttga gcatagaact attgatgtta atttggaagg
 661 agaaaatgga aacacagctg tgatcattgc gtgcaccaca aataatagcg aagcattgca
 721 gattttgctt aaaaaaggag ctaagccatg taaatcaaat aaatggggat gtttccctat
 781 tcaccaagct gcattttcag gttccaaaga atgcatggaa ataatactaa ggtttggtga
 841 agagcatggg tacagtagac agttgcacat taactttatg aataatggga aagccacccc
 901 tctccacctg gctgtgcaaa atggtgactt ggaaatgatc aaaatgtgcc tggacaatgg
 961 tgcacaaata gacccagtgg agaagggaag gtgcacagcc attcattttg ctgccaccca
1021 gggagccact gagattgtta aactgatgat atcgtcctat tctggtagcg tggatattgt
1081 taacacaacc gatggatgtc atgagaccat gcttcacaga gcttcattgt ttgatcacca
1141 tgagctagca gactatttaa tttcagtggg agcagatatt aataagatcg attctgaagg
1201 acgctctcca cttatattag caactgcttc tgcatcttgg aatattgtaa atttgctact
1261 ctctaaaggt gcccaagtag acataaaaga taattttgga cgtaattttc tgcatttaac
1321 tgtacagcaa ccttatggat taaaaaatct gcgacctgaa tttatgcaga tgcaacagat
1381 caaagagctg gtaatggatg aagacaacga tgggtgtact cctctacatt atgcatgtag
1441 acaggggggc cctggttctg taaataacct acttggcttt aatgtgtcca ttcattccaa
```

Figure 17 (Continued)

1501 aagcaaagat aagaaatcac ctctgcattt tgcagccagt tatgggcgta tcaatacctg 1561 tcagaggctc ctacaagaca taagtgatac gaggcttctg aatgaaggtg accttcatgg 1621 aatgactcct ctccatctgg cagcaaagaa tggacatgat aaagtagttc agcttcttct 1681 gaaaaaaggt gcattgtttc tcagtgacca caatggctgg acagctttgc atcatgcgtc 1741 catgggcggg tacactcaga ccatgaaggt cattcttgat actaatttga agtgcacaga 1801 tcgcctggat gaagacggga acactgcact tcactttgct gcaagggaag gccacgccaa 1861 agccgttgcg cttcttctga gccacaatgc tgacatagtc ctgaacaagc agcaggcctc 1921 cttttttgcac cttgcacttc acaataagag gaaggaggtt gttcttacga tcatcaggag 1981 caaaagatgg gatgaatgtc ttaagatttt cagtcataat tctccaggca ataaatgtcc 2041 aattacagaa atgatagaat acctccctga atgcatgaag gtacttttag atttctgcat 2101 gttgcattcc acagaagaca agtcctgccg agactattat atcgagtata atttcaaata 2161 tcttcaatgt ccattagaat tcaccaaaaa aacacctaca caggatgtta tatatgaacc 2221 gcttacagcc ctcaacgcaa tggtacaaaa taaccgcata gagcttctca atcatcctgt 2281 gtgtaaagaa tatttactca tgaaatggtt ggcttatgga tttagagctc atatgatgaa 2341 tttaggatct tactgtcttg gtctcatacc tatgaccatt ctcgttgtca atataaaacc 2401 aggaatggct ttcaactcaa ctggcatcat caatgaaact agtgatcatt cagaaatact 2461 agataccacg aattcatatc taataaaaac ttgtatgatt ttagtgtttt tatcaagtat 2521 atttgggtat tgcaaagaag cggggcaaat tttccaacag aaaaggaatt attttatgga 2581 tataagcaat gttcttgaat ggattatcta cacgacgggc atcattttg tgctgccctt 2641 gtttgttgaa ataccagctc atctgcagtg gcaatgtgga gcaattgctg tttacttcta 2701 ttggatgaat ttcttattgt atcttcaaag atttgaaaat tgtggaattt ttattgttat 2761 gttggaggta attttgaaaa ctttgttgag gtctacagtt gtatttatct tccttcttct 2821 ggcttttgga ctcagctttt acatcctcct gaatttacag gatcccttca gctctccatt 2881 gctttctata atccagacct tcagcatgat gctaggagat atcaattatc gagagtcctt 2941 cctagaacca tatctgagaa atgaattggc acatccagtt ctgtcctttg cacaacttgt 3001 ttccttcaca atatttgtcc caattgtcct catgaattta cttattggtt tggcagttgg

Figure 17 (Continued)

3061 cgacattgct gaggtccaga aacatgcatc attgaagagg atagctatgc aggtggaact 3121 tcataccagc ttagagaaga agctgccact ttggtttcta cgcaaagtgg atcagaaatc 3181 caccatcgtg tatcccaaca aacccagatc tggtgggatg ttattccata tattctgttt 3241 tttattttgc actggggaaa taagacaaga aataccaaat gctgataaat ctttagaaat 3301 ggaaatatta aagcagaaat accggctgaa ggatcttact tttctcctgg aaaaacagca 3361 tgagctcatt aaactgatca ttcagaagat ggagatcatc tctgagacag aggatgatga 3421 tagccattgt tcttttcaag acaggtttaa gaaagagcag atggaacaaa ggaatagcag 3481 atggaatact gtgttgagag cagtcaaggc aaaaacacac catcttgagc cttagctcct 3541 cagaccttca gtgaggcttc taatgggggg tgcatgactt gctggttcta actttcaatt 3601 taaaagagt gaggaagaag cagaatgatt cattttgctg cgtgtgaaat catggttcct 3661 gcatgctgta taaaagtaaa ccatctttta tcctctattc atattttcta ccaatcacta 3721 tgtattgggg atatctttgc agatatgttc aaattggact ggactttgat gagatataat 3781 ctcattattt gaatgggtag aaaatgaatt tgctagaaca cacatttta atgaaaagaa 3841 gtaataaatg taactattaa gctaaaatgc aaatgtcagt actgaattcc tgcttgttaa 3901 ttacataata tgtgatgctc tagaaaatag tcacaagtat taataatgcc ttagatgata 3961 gtcttaaata ttaggttgag gtctacctaa cctaagctgc ttcctggaaa gcttcatgtt 4021 gaaagaacct atgggtggca ccatgtggac ttttctgtcc ctactgtgat aatagcccc 4081 acccttcttg ctgtccccaa cacacctgat gtcactttga gccatatagt tgaagtacaa 4141 attaataggc cttatgatat gcacgaattt tactatagat aatatatgtt gtttctggtt 4201 ttgtttgcca atgagcataa taaatgtaaa acctatatag tatccctgtg attattgtat 4261 gagcctttgt ttgagatttg aaaacaacat ggctccatca catattccct tttttctttt 4321 gatgtctact caaatcatga attaatcaca tacctcatca ttaatctttt caaggtcctt 4381 ctattgtttt gtctgatttt ctccatcatc ctgattagca tgtttattcc ctcactaccc 4441 ccaggagata ttcactgtaa tgaatatgtc tttggctatg tatgtgtcct tgtgttatgt 4501 tgtacagtgt tgtttttgagt ctgttattat ttacacagat gttattatgc tatagcttct 4561 atttctgttt ttgcttctta tttctcttat aattctcact tatttcctat tttttctact

Figure 17 (Continued)

```
4621 catttctatt tgttactcct ttttactgga catgatgttt acaagataca actgtgttac
4681 tgtattccat ctagtacggg gcctttggtg tggcttacta tttcattgtg tgcacccacc
4741 cacccaccac actggacttt tctagagatg gacagcttgg ttacctccac cttcctgcac
4801 tcattctcaa acatactgat gttcatacaa accagcagag tgctgaggga cgatatgtac
4861 tattacaaaa ccagacactt ttacattcat ggtccaacag atcacatggc ctagaggcaa
4921 tgttgcatat accttaatct ttgatatgaa taatatcttt gttctttata tttcttaaaa
4981 cagaaagggt ggaaaatcac tatacagaag caatatccaa agatctcctg atcataaaga
5041 caagggggtct tttcagtctt ccctctcctc aaaccttgtg tagcattgca caatatagat
5101 ctcagtcaac attcactgag tgccaagaat gtgagaaaca ctgtaccatg cctgtcatgc
5161 gaaatattta aataaacaga ttgtcttaca
```

Figure 22
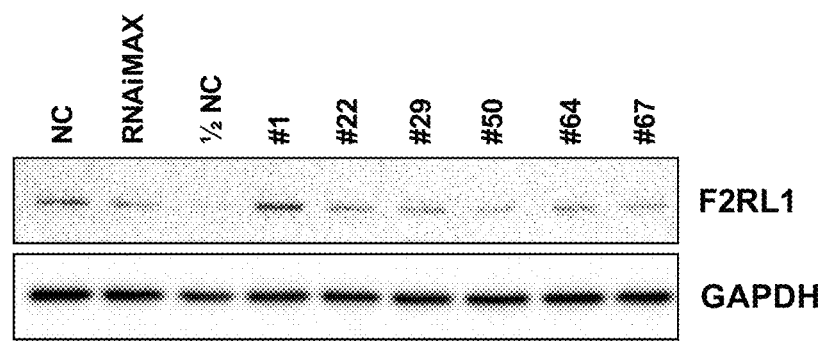
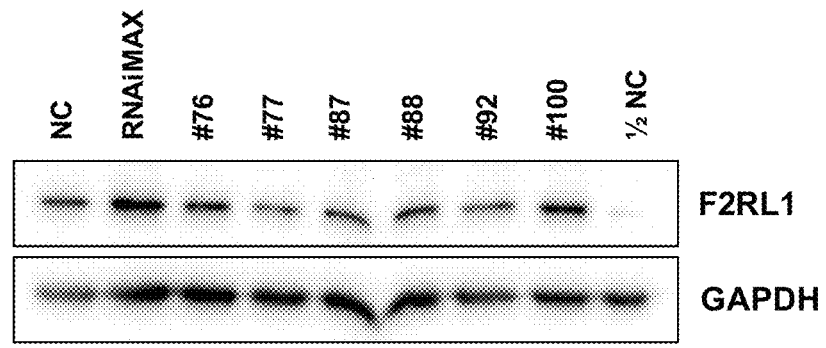

Figure 24
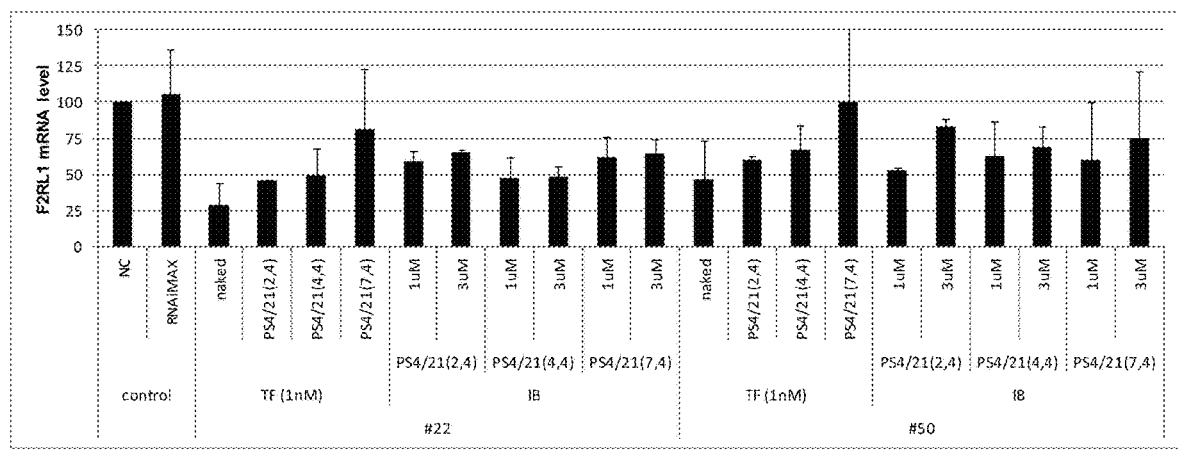
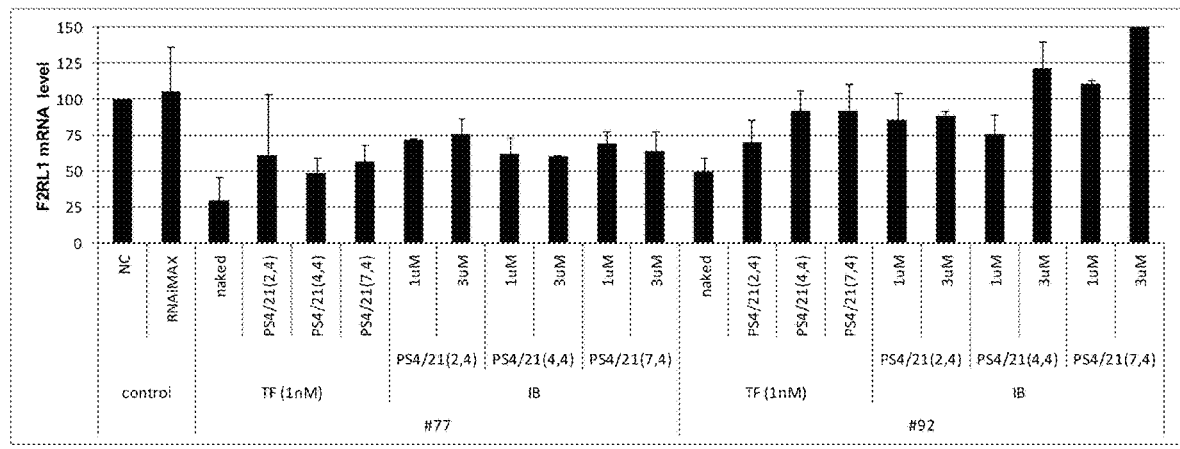

Figure 28

Human F2RL1 mRNA sequence. (NM_005242)

```
   1 acgctgctcc ttcggtttcc ctgaaaccta acccgccctg gggaggcgcg cagcagaggc
  61 tccgattcgg ggcaggtgag aggctgactt tctctcggtg cgtccagtgg agctctgagt
 121 ttcgaatcgg cggcggcgga ttccccgcgc gcccggcgtc ggggcttcca ggaggatgcg
 181 gagccccagc gcggcgtggc tgctgggggc cgccatcctg ctagcagcct ctctctcctg
 241 cagtggcacc atccaaggaa ccaatagatc tctaaagga agaagcctta ttggtaaggt
 301 tgatggcaca tcccacgtca ctggaaaagg agttacagtt gaaacagtct tttctgtgga
 361 tgagttttct gcatctgtcc tcactggaaa actgaccact gtcttcttc caattgtcta
 421 cacaattgtg tttgtggtgg gtttgccaag taacggcatg gccctgtggg tctttctttt
 481 ccgaactaag aagaagcacc ctgctgtgat ttacatggcc aatctggcct tggctgacct
 541 cctctctgtc atctggttcc ccttgaagat tgcctatcac atacatggca acaactggat
 601 ttatggggaa gctctttgta atgtgcttat tggcttttc tatggcaaca tgtactgttc
 661 cattctcttc atgacctgcc tcagtgtgca gaggtattgg gtcatcgtga accccatggg
 721 gcactccagg aagaaggcaa acattgccat tggcatctcc ctggcaatat ggctgctgat
 781 tctgctggtc accatcccct tgtatgtcgt gaagcagacc atcttcattc ctgccctgaa
 841 catcacgacc tgtcatgatg ttttgcctga gcagctcttg gtgggagaca tgttcaatta
 901 cttcctctct ctggccattg gggtcttct gttcccagcc ttcctcacag cctctgccta
 961 tgtgctgatg atcagaatgc tgcgatcttc tgccatggat gaaaactcag agaagaaaag
1021 gaagagggcc atcaaactca ttgtcactgt cctggccatg tacctgatct gcttcactcc
1081 tagtaacctt ctgcttgtgg tgcattattt tctgattaag agccagggcc agagccatgt
1141 ctatgccctg tacattgtag ccctctgcct ctctacccct aacagctgca tcgacccctt
1201 tgtctattac tttgtttcac atgatttcag ggatcatgca aagaacgctc tcctttgccg
1261 aagtgtccgc actgtaaagc agatgcaagt atccctcacc tcaaagaaac actccaggaa
1321 atccagctct tactcttcaa gttcaaccac tgttaagacc tcctattgag ttttccaggt
1381 cctcagatgg gaattgcaca gtaggatgtg gaacctgttt aatgttatga ggacgtgtct
1441 gttatttcct aatcaaaaag gtctcaccac ataccatgtg gatgcagcac ctctcaggat
1501 tgctaggagc tccctgtttt gcatgagaaa agtagtcccc caaattaaca tcagtgtctg
1561 tttcagaatc tctctactca gatgacccca gaaactgaac caacagaagc agacttttca
1621 gaagatggtg aagacagaaa cccagtaact tgcaaaaagt agacttggtg tgaagactca
1681 cttctcagct gaaattatat atatacacat atatatattt tacatctggg atcatgatag
```

Figure 28 (Continued)

1741 acttgttagg gcttcaaggc cctcagagat gatcagtcca actgaacgac cttacaaatg 1801 aggaaaccaa gataaatgag ctgccagaat caggtttcca atcaacagca gtgagttggg 1861 attggacagt agaatttcaa tgtccagtga gtgaggttct tgtaccactt catcaaaatc 1921 atggatcttg gctgggtgcg gtgcctcatg cctgtaatcc tagcactttg ggaggctgag 1981 gcaggcaatc acttgaggtc aggagttcga gaccagcctg gccatcatgg cgaaacctca 2041 tctctactaa aaatacaaaa gttaaccagg tgtgtggtgc acgtttgtaa tcccagttac 2101 tcaggaggct gaggcacaag aattgagtat cactttaact caggaggcag aggttgcagt 2161 gagccgagat tgcaccactg cactccagct tgggtgataa aataaaataa aatagtcgtg 2221 aatcttgttc aaaatgcaga ttcctcagat tcaataatga gagctcagac tgggaacagg 2281 gcccaggaat ctgtgtggta caaacctgca tggtgtttat gcacacagag atttgagaac 2341 cattgttctg aatgctgctt ccatttgaca aagtgccgtg ataattttg aaaagagaag 2401 caaacaatgg tgtctctttt atgttcagct tataatgaaa tctgtttgtt gacttattag 2461 gactttgaat tatttcttta ttaaccctct gagttttgt atgtattatt attaaagaaa 2521 aatgcaatca ggattttaaa catgtaaata caaattttgt ataacttttg atgacttcag 2581 tgaaattttc aggtagtctg agtaatagat tgttttgcca cttagaatag catttgccac 2641 ttagtatttt aaaaaataat tgttggagta tttattgtca gttttgttca cttgttatct 2701 aatacaaaat tataaagcct tcagagggtt tggaccacat ctctttggaa aatagtttgc 2761 aacatattta agagatactt gatgccaaaa tgactttata caacgattgt atttgtgact 2821 tttaaaaata attattttat tgtgtaattg atttataaat aacaaaattt tttttacaac 2881 tta Figure 30
A. Intradermal injection
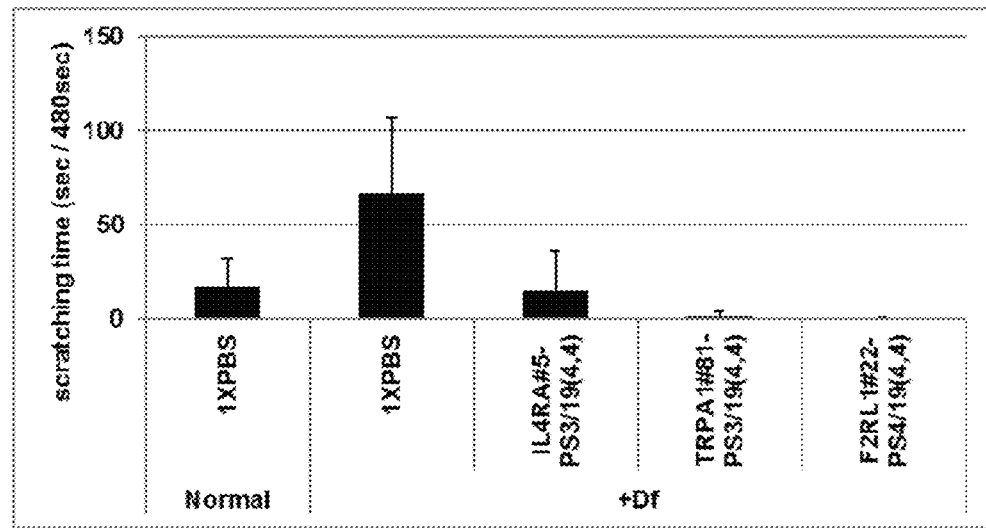
B. Cream emulsified cp-asiRNA application
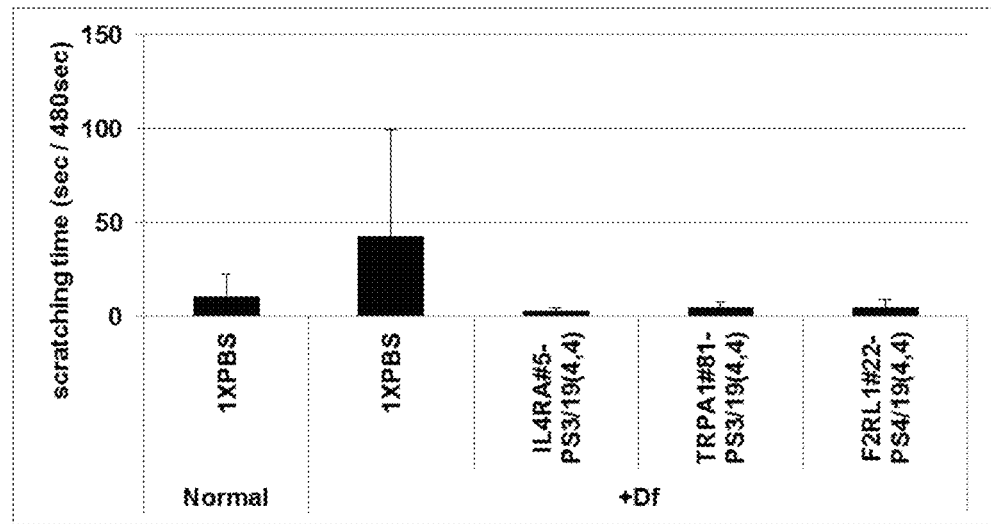

Figure 31
A. Intradermal injection
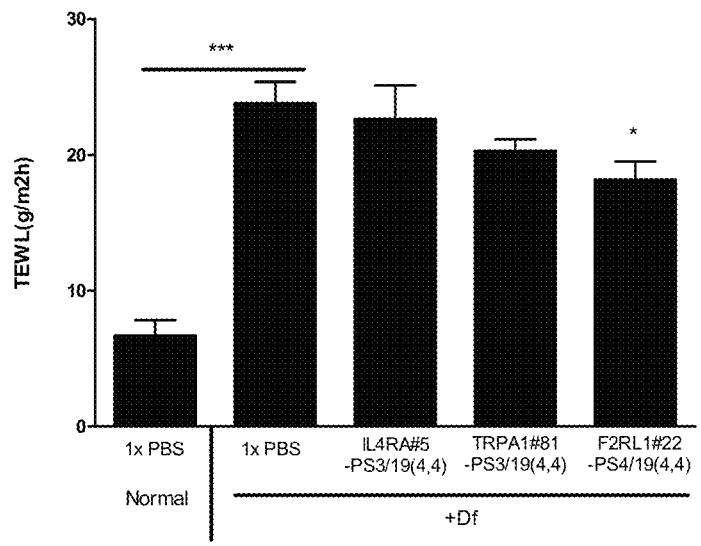
B. Cream emulsified cp-asiRNA application
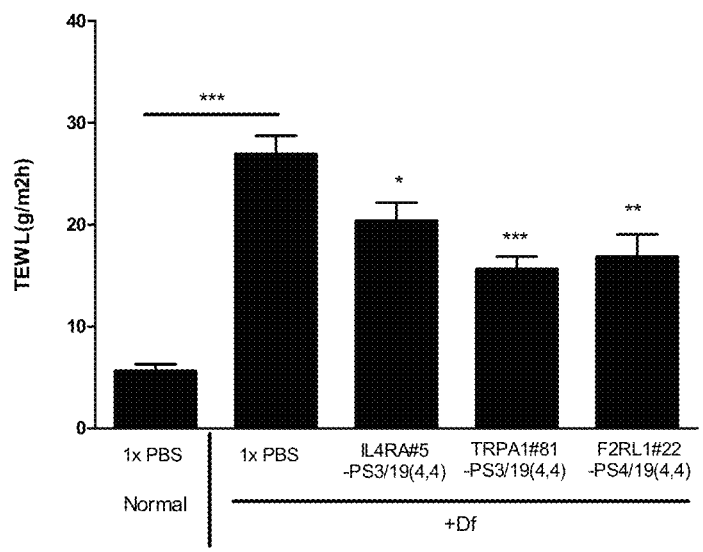

Figure 33
A. Intradermal injection
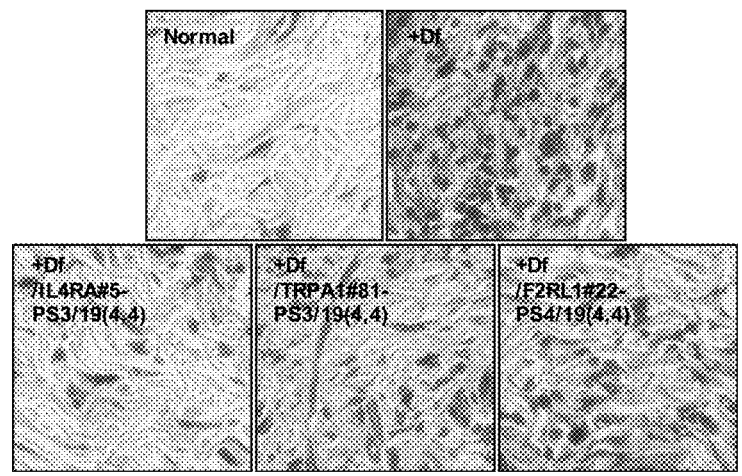
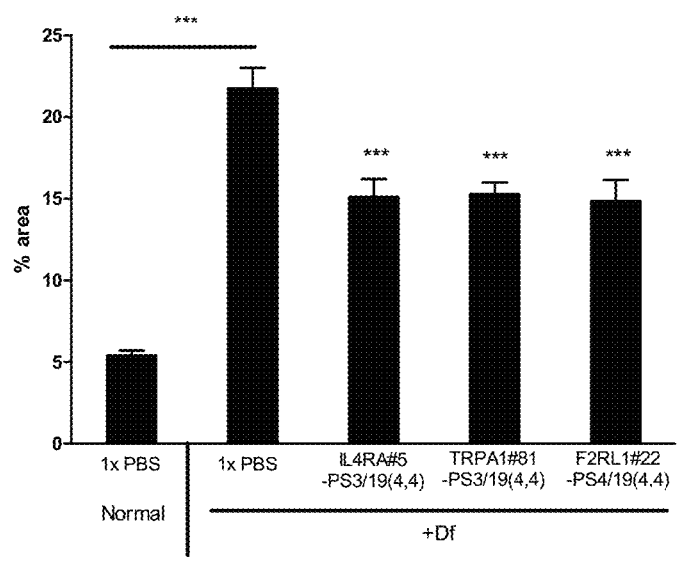

Figure 33 (Cont.)
B. Cream emulsified cp-asiRNA application
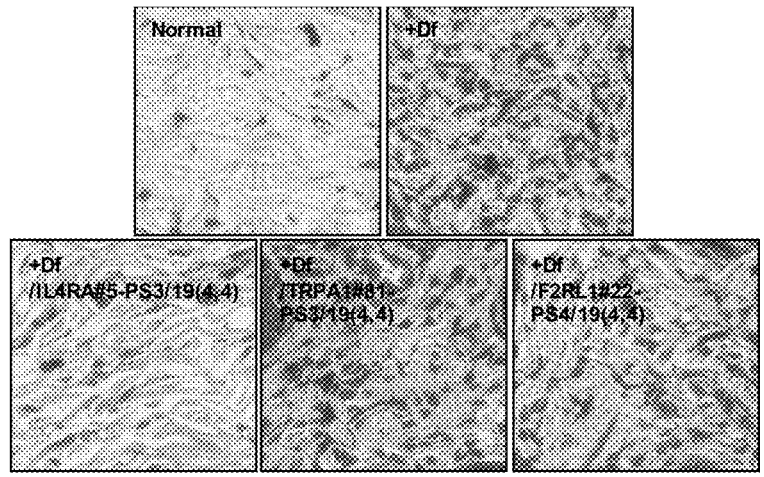
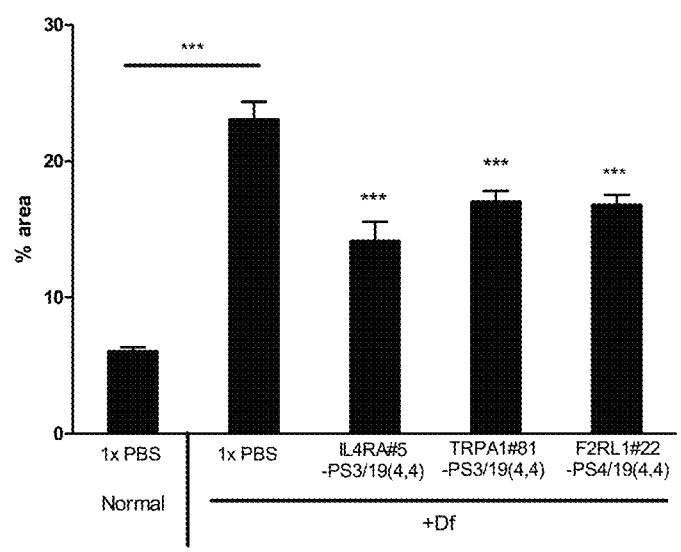

TREATMENT OF ATOPIC DERMATITIS AND ASTHMA USING RNA COMPLEXES THAT TARGET IL4Rα, TRPA1, OR F2RL1

RELATED APPLICATIONS

This application is a continuation of U.S. patent application Ser. No. 16/352,417, filed Mar. 13, 2019, which is a continuation of U.S. patent application Ser. No. 15/422,186, filed Feb. 1, 2017 (now U.S. Pat. No. 10,358,648), which claims the benefit of priority to U.S. Provisional Patent Application Ser. No. 62/290,298, filed Feb. 2, 2016, the content of each of which is hereby incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 5, 2019, is named OLX-009C2_ST25.txt and is 176,350 bytes in size.

BACKGROUND

Dysregulation of the immune system can result in auto-immune diseases such as atopic dermatitis and asthma. Atopic dermatitis, also referred to as eczema, is an inflammatory disease characterized by the presence of itchy and tender skin, edema, and erythema. Atopic dermatitis is common in children and infants, although the disease can occur at any age.

About 70% of atopic dermatitis patients develop asthma by "atopic march," characterized by the progression of atopic dermatitis to asthma and allergic rhinitis. Asthma is a respiratory disorder also associated with dysregulation of the immune system. More specifically, it is a chronic respiratory disease marked by respiratory spasms and obstruction due to allergic inflammation of the bronchi, causing repetitive breathing shortness, wheezing and coughing. Asthma prevalence is estimated to be as high as 300 million individuals worldwide, and about 8% of the population of major developed countries are afflicted with asthma.

IL4Rα, F2RL1 and TRPA1 genes play a key role in the onset and progression of symptoms of atopic dermatitis and/or asthma. When exposed to foreign antigens, dendritic cells in atopic dermatitis patients activate Th2 cells, leading to the secretion of cytokines (e.g., IL-4, IL-5, IL-10, and IL-13) by the activated Th2 cells. Among the cytokines, IL-4 and IL-13 are known to play an important role in the onset of atopic dermatitis, while IL-4 and IL-13 have been reported to worsen atopic dermatitis symptoms of through the inhibition of human beta defensin-3 and filaggrin, both of which maintain the skin barrier. The receptors for IL-4 and IL-13 are heterodimers and contain IL4Rα (interleukin 4 receptor, alpha, also known as IL4Rα). Therefore, down-regulation of the IL4Rα can block out the signals of IL-4 and IL-13.

The main cause of the itching symptom experienced by atopic dermatitis patients is the overexpression of thymic stromal lymphopoietin (TSLP) in keratinocytes, which elevates the transient receptor potential (TRP) of TRP ion channels, including TRPV1 and TRPA1. Thus, the symptoms of atopic dermatitis can be treated by the inhibition of TRPA1.

Coagulation factor II (thrombin) receptor-like 1 (F2RL1, also known as protease-activated receptor 2, PAR2) is expressed by keratinocytes, activated endothelial cells, and sensory nerves in the skin and is involved in various inflammation reactions, pigmentation production, and the skin barrier function. F2RL1 plays a pivotal role in the activation of proteinases, which induce inflammation reactions and the aggravated skin conditions seen in atopic dermatitis patients.

Thus, there is a need for new and improved therapeutics targeting IL4Rα, TRPA1 and F2RL1 for the treatment or atopic dermatitis or asthma.

SUMMARY

In certain aspects, provided herein are RNA complexes that target IL4Rα, TRPA1, or F2RL1 and are useful for treating and/or preventing atopic dermatitis and/or asthma. In certain aspects, provided herein are pharmaceutical compositions comprising such RNA complexes and methods of using such RNA complexes and pharmaceutical compositions.

In certain aspects, provided herein is an RNA complex comprising an antisense strand having sequence complementarity to an IL4Rα, TRPA1, or F2RL1 mRNA sequence and a sense strand having sequence complementarity to the antisense strand. In some embodiments, the RNA complex is capable of inhibiting IL4Rα, TRPA1, or F2RL1 expression by a cell (e.g., a keratinocyte). In some embodiments, the RNA complex is an asymmetric shorter-duplex small interfering RNA (an asiRNA). In some embodiments, the RNA complex is an RNA complex listed in Table 1, Table 2, Table 3, Table 4, Table 5, Table 6, Table 7, Table 8, Table 9, or Table 10. In some embodiments, the RNA complex comprises the antisense and sense strand of IL4RA #5. In some embodiments, the RNA complex comprises the antisense and sense strand of TRPA1 #81. In some embodiments, the RNA complex comprises the antisense and sense strand of F2RL1 #22.

In some embodiments, the RNA complex provided herein comprises a chemical modification, wherein the modification facilitates the penetration of a cellular membrane in the absence of a delivery vehicle. In some embodiments, the modification is a 2'-O-methylated nucleoside, a phosphorothioate bond or a hydrophobic moiety. In some embodiments, the RNA complexes provided herein comprise a hydrophobic moiety. In some embodiments, the hydrophobic moiety can be any chemical structure having hydrophobic character. For example, in some embodiments the hydrophobic moiety is a lipid, a lipophilic peptide and/or a lipophilic protein. In some embodiments, the hydrophobic moiety is a lipid, such as cholesterol, tocopherol, or a long-chain fatty acid having 10 or more carbon atoms (e.g., stearic acid or palmitic acid). In some embodiments, the hydrophobic moiety is cholesterol. In some embodiments, the RNA complex is a modified RNA complex listed in Table 2, Table 3, Table 5, Table 6, Table 8, Table 9, or Table 10. In certain embodiments, the RNA complex is not cytotoxic.

In certain aspects, provided herein is a pharmaceutical composition comprising an RNA complex provided herein and a pharmaceutically acceptable carrier. In certain embodiments, the pharmaceutical composition is formulated for topical delivery. In some embodiments, the pharmaceutical composition is a cream or a lotion. In some embodiments, the pharmaceutical composition is formulated for parenteral, intravenous, or oral delivery. In other embodiments, the pharmaceutical composition is formulated for inhalation.

In certain aspects, provided herein is a method of inhibiting IL4Rα, TRPA1, or F2RL1 expression by a cell, comprising contacting the cell with an RNA complex provided herein.

In certain aspects, provided herein is a method of inhibiting gene expression IL4Rα, TRPA1, or F2RL1 in a human subject comprising administering to the subject an RNA complex or pharmaceutical composition provided herein. In certain aspects, provided herein is a method of treating a human subject for atopic dermatitis and/or asthma comprising administering to the subject an RNA complex or pharmaceutical composition provided herein.

BRIEF DESCRIPTION OF THE DRAWINGS

FIG. 1 shows the gene silencing efficiency of 73 exemplary asiRNAs that target IL4Rα.

FIG. 8 provides the human IL4Rα mRNA sequence. Figure discloses SEQ ID NO: 678.

FIG. 9 shows the gene silencing efficiency of 102 exemplary asiRNAs that target TRPA1.

FIG. 15 shows the inhibition of TRPA1 protein expression by 8 exemplary cp-asiRNAs.

FIG. 17 provides the human TRPA1 mRNA sequence. Figure discloses SEQ ID NO: 679.

FIG. 22 shows the inhibition of F2RL1 protein expression by 12 exemplary asiRNAs that target F2RL1.

FIG. 24 shows the inhibition of F2RL1 mRNA expression by exemplary cp-asiRNAs.

FIG. 28 shows the mRNA sequence of human F2RL1. Figure discloses SEQ ID NO: 680.

FIG. 30 shows scratching time observed in Dermatophagoides farinae body extract (Df) cream treated samples.

FIG. 31 shows intradermal injection versus cream cp-asiRNA application in rodents of atopic dermatitis.

FIG. 33 shows mast cell infiltration analysis of treated skin region.

DETAILED DESCRIPTION

General

Figure 2:
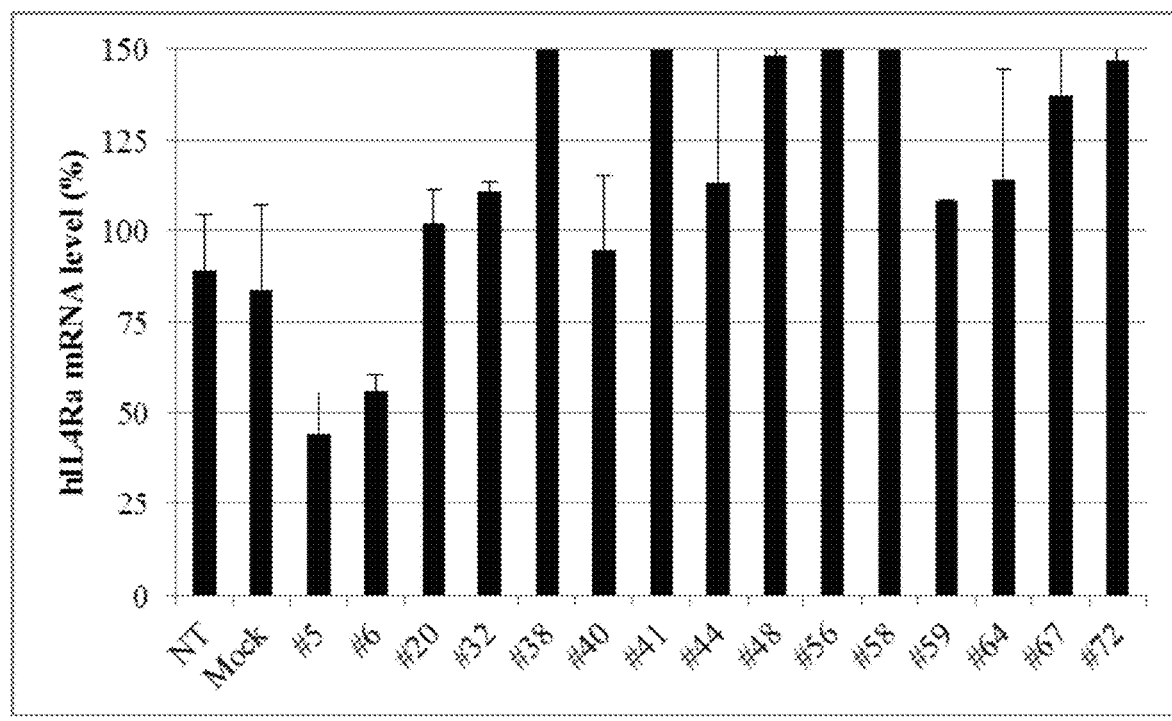
FIG. 2 shows the gene silencing efficiency of 15 exemplary asiRNAs that target IL4Rα.

In certain aspects, provided herein are asymmetric RNA complexes (e.g., asiRNAs or cp-asiRNAs) that inhibit IL4Rα, TRPA1, and/or F2RL1 and are therefore useful for the treatment of atopic dermatitis and/or asthma. In some embodiments, the RNA complexes are chemically modified to be capable of penetrating a cell without need for a transfection vehicle. In some embodiments, the RNA complex is an RNA complex listed in Table 1, Table 2, Table 3, Table 4, Table 5, Table 6, Table 7, Table 8, Table 9, or Table 10. In certain aspects, provided herein are pharmaceutical compositions comprising such RNA complexes and methods of using such RNA complexes and pharmaceutical compositions.

In some embodiments, the RNA complexes described herein are asiRNAs or cp-asiRNAs. As used herein, the term asiRNA refers to double-stranded asymmetrical short interfering RNA molecules that have a 19-21 nt antisense strand and a 13-17 nt sense strand. Additional information on asiRNAs can be found in U.S. Pat. Pub. No. 2012/0238017 and in Chang et al., Mol. Ther. 17:725-732 (2009), each of which is hereby incorporated by reference in its entirety.

In some embodiments, the RNA complexes described herein are delivered to cells using a delivery vehicle, such as liposomes, cationic polymers, cell penetrating peptides (CPPs), protein transduction domains (PTDs), antibodies and/or aptamers. In some embodiments, the RNA complex described herein is chemically modified so as to not require the use of such delivery vehicles to mediate IL4Rα, TRPA1, and/or F2RL1 inhibition in a cell. Such RNA complexes are referred to herein as cell-penetrating asiRNAs (cp-asiRNAs).

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering.

As used herein, the term "immunomodulator" refers to a compound or composition which weakens, stimulate, or otherwise modulates the immune system. Examples include, by are not limited to leukotriene receptor agonists, immunosuppressants (e.g., FK-506), or cytokines.

As used herein, the terms "interfering nucleic acid" and "inhibiting nucleic acid" are used interchangeably. Interfering nucleic acids generally include a sequence of cyclic subunits, each bearing a base-pairing moiety, linked by intersubunit linkages that allow the base-pairing moieties to hybridize to a target sequence in a nucleic acid (typically RNA) by Watson-Crick base pairing, to form a nucleic acid: oligomer heteroduplex within the target sequence. Interfering RNA molecules include, but are not limited to, antisense molecules, siRNA molecules, asiRNA molecules, cp-asiRNA molecules, single-stranded siRNA molecules, miRNA molecules and shRNA molecules. Such an interfering nucleic acids can be designed to block or inhibit translation of mRNA or to inhibit natural pre-mRNA splice processing, or induce degradation of targeted mRNAs, and may be said to be "directed to" or "targeted against" a target sequence with which it hybridizes. Interfering nucleic acids may include, for example, peptide nucleic acids (PNAs), locked nucleic acids (LNAs), 2'-O-Methyl oligonucleotides and RNA interference agents (siRNA agents). RNAi molecules generally act by forming a heteroduplex with the target molecule, which is selectively degraded or "knocked down," hence inactivating the target RNA. Under some conditions, an interfering RNA molecule can also inactivate a target transcript by repressing transcript translation and/or inhibiting transcription of the transcript. An interfering nucleic acid is more generally said to be "targeted against" a biologically relevant target, such as a protein, when it is targeted against the nucleic acid of the target in the manner described above.

The terms "polynucleotide", and "nucleic acid" are used interchangeably. They refer to a polymeric form of nucleotides, whether deoxyribonucleotides, ribonucleotides, or analogs thereof, in any combination and of any length. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, Unucleobases are interchangeable with T nucleobases.

The phrase "pharmaceutically-acceptable carrier" as used herein means a pharmaceutically-acceptable material, composition or vehicle, such as a liquid or solid filler, diluent, excipient, or solvent encapsulating material.

An oligonucleotide "specifically hybridizes" to a target polynucleotide if the oligomer hybridizes to the target under physiological conditions, with a Tm substantially greater than 45° C., or at least 50° C., or at least 60° C.-80° C. or higher. Such hybridization corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

As used herein, a therapeutic that "prevents" a disorder or condition refers to a compound that, when administered to a statistical sample prior to the onset of the disorder or condition, reduces the occurrence of the disorder or condition in the treated sample relative to an untreated control sample, or delays the onset or reduces the severity of one or more symptoms of the disorder or condition relative to the untreated control sample.

RNA Complexes

In certain aspects, provided herein are RNA complexes that target IL4Rα, TRPA1, and/or F2RL1 mRNA and inhibit IL4Rα, TRPA1, and/or F2RL1 expression by a cell, respectively. The nucleic acid sequence of human IL4Rα, TRPA1, and F2RL1 mRNA is provided in FIG. 8, FIG. 17, and FIG. 28, respectively.

In certain aspects, provided herein is an RNA complex comprising an antisense strand having sequence complementarity to an IL4Rα, TRPA1, or F2RL1 mRNA sequence (e.g., a human IL4Rα, TRPA1, or F2RL1 mRNA sequence) and a sense strand having sequence complementarity to the antisense strand. In some embodiments, the RNA complex is capable of inhibiting IL4Rα, TRPA1, or F2RL1 expression by a cell. In some embodiments, the RNA complex is an asymmetric shorter-duplex small interfering RNA (an asiRNA). In some embodiments, the RNA complex is an RNA complex listed in Table 1, Table 2, Table 3, Table 4, Table 5, Table 6, Table 8 or Table 10. The RNA complexes described herein can contain RNA bases, non-RNA bases or a mixture of RNA bases and non-RNA bases. For example, certain RNA complexes provided herein can be primarily composed of RNA bases but also contain DNA bases or non-naturally occurring nucleotides.

In some embodiments, the antisense strand is at least 19 nucleotides (nt) in length. In some embodiments, the antisense strand is 19 to 21 nt in length (i.e., 19, 20 or 21 nt in length). In some embodiments, at least 13, 14, 15, 16, 17, 18, 19, 20 or 21 nt of the antisense strand are complementary to the IL4Rα, TRPA1, or F2RL1 mRNA sequence. Perfect complementarity is not necessary. In some embodiments, the antisense strand is perfectly complementary to the IL4Rα, TRPA1, or F2RL1 mRNA sequence.

In some embodiments, the antisense strand is at least 24 nt in length (e.g., at least 25 nt in length, at least 26 nt in length, at least 27 nt in length, at least 28 nt in length, at least 29 nt in length, at least 30 nt in length or at least 31 nt in length). In some embodiments, the antisense strand is no greater than 124 nt in length (e.g., no greater than 100 nt in length, no greater than 90 nt in length, no greater than 80 nt in length, no greater than 70 nt in length, no greater than 60 nt in length, no greater than 50 nt in length or no greater than 40 nt in length. In some embodiments, the antisense strand is 31 nt in length. In some embodiments, at least 16, 17, 18, 19, 20, 21, 22, 23, 24, 25, 26, 27, 29, 29, 30 or 31 nt of the antisense strand are complementary to the IL4Rα, TRPA1, or F2RL1 mRNA sequence. Perfect complementarity is not necessary. In some embodiments, the antisense strand is perfectly complementary to the IL4Rα, TRPA1, or F2RL1 mRNA sequence.

In some embodiments, the sense strand is 15 to 17 nt in length (i.e., 15 nt in length, 16 nt in length or 17 nt in length). In some embodiments, at least 15 nt, at least 16 nt or at least 17 nt of the sense strand are complementary to the sequence of the antisense strand. In some embodiments the sense strand is perfectly complementary to the sequence of the antisense strand.

In some embodiments, the antisense strand and the sense strand form a complex in which the 5' end of the antisense strand and the 3' end of the sense strand form a blunt end. In some embodiments, the antisense strand and the sense strand form a complex in which the 5' end of the antisense strand overhangs the 3' end of the sense strand (e.g., by 1, 2, 3, 4 or 5 nt). In some embodiments, the antisense strand and the sense strand form a complex in which the 5' end of the sense strand overhangs the 3' end of the antisense strand (e.g., by 1, 2, 3, 4 or 5 nt).

In some embodiments, the antisense strand and/or the sense strand of the RNA complex has a sense strand sequence and/or an antisense strand sequence selected from the sequences listed in Table 1, Table 2, Table 3, Table 4, Table 5, Table 6, Table 8 or Table 10.

In some embodiments, the RNA complex provided herein comprises a chemical modification, wherein the modification facilitates the penetration of a cellular membrane in the absence of a delivery vehicle. In some embodiments, the modification is a 2'-O-methylated nucleoside, a phosphorothioate bond or a hydrophobic moiety. In some embodiments, the chemical modification is a hydrophobic moiety. In some embodiments, the hydrophobic moiety is a cholesterol moiety. In some embodiments, the RNA complex is a modified RNA complex listed in Table 2, table 3, Table 5, Table 6, Table 8, Table 9, or Table 10. In certain embodiments, the RNA complex is not cytotoxic.

The RNA complexes described herein can employ a variety of oligonucleotide chemistries. Examples of oligonucleotide chemistries include, without limitation, peptide nucleic acid (PNA), linked nucleic acid (LNA), phosphorothioate, 2'O-Me-modified oligonucleotides, and morpholino chemistries, including combinations of any of the foregoing. In general, PNA chemistries can utilize shorter targeting sequences because of their relatively high target binding strength relative to 2'O-Me oligonucleotides. Phosphorothioate and 2'O-Me-modified chemistries are often combined to generate 2'O-Me-modified oligonucleotides having a phosphorothioate backbone. See, e.g., PCT Publication Nos. WO/2013/112053 and WO/2009/008725, each of which is hereby incorporated by reference in its entirety.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition. The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969, 766, 7,211,668, 7,022,851, 7,125,994, 7,145,006 and 7,179, 896. See also U.S. Pat. Nos. 5,539,082; 5,714,331; and 5,719,262 for the preparation of PNAs. Further teaching of PNA compounds can be found in Nielsen et al., *Science*, 254:1497-1500, 1991. Each of the foregoing is incorporated by reference in its entirety.

Interfering nucleic acids may also contain "locked nucleic acid" subunits (LNAs). "LNAs" are a member of a class of modifications called bridged nucleic acid (BNA). BNA is characterized by a covalent linkage that locks the conformation of the ribose ring in a C3-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., *Chemical Communications* (1998) 455; *Tetrahedron* (1998) 54:3607, and *Accounts of Chem. Research* (1999) 32:301); Obika, et al., *Tetrahedron Letters* (1997) 38:8735; (1998) 39:5401, and *Bioorganic Medicinal Chemistry* (2008) 16:9230. Compounds provided herein may incorporate one or more LNAs; in some cases, the compounds may be entirely composed of LNAs. Methods for the synthesis of individual LNA nucleoside subunits and their incorporation into oligonucleotides are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. One embodiment is an LNA-containing compound where each LNA subunit is separated by a DNA subunit. Certain compounds are composed of alternating LNA and DNA subunits where the intersubunit linker is phosphorothioate.

In certain embodiments, the RNA complex is linked to a cholesterol moiety. In some embodiments, the cholesterol moiety is attached to the 3' terminus of the sense strand. In some embodiments, the cholesterol moiety is attached to the 3' terminus of the antisense strand. In some embodiments, the cholesterol moiety is attached to the 5' terminus of the sense strand. In some embodiments, the cholesterol moiety is attached to the 5' terminus of the antisense strand.

In some embodiments, the RNA complex comprises a 2'-O-methylated nucleoside. 2'-O-methylated nucleosides carry a methyl group at the 2'-OH residue of the ribose molecule. 2'-O-Me-RNAs show the same (or similar) behavior as RNA, but are protected against nuclease degradation. 2'-O-Me-RNAs can also be combined with phosphothioate oligonucleotides (PTOs) for further stabilization. 2'-O-Me-RNAs (phosphodiester or phosphothioate) can be synthesized according to routine techniques in the art (see, e.g., Yoo et al., *Nucleic Acids Res.* 32:2008-16, 2004, which is hereby incorporated by reference).

In some embodiments, the 2'-O-methyl nucleoside is positioned at the 3' terminus of the sense strand. In some embodiments, 3' terminal region of the sense strand comprises a plurality of 2'-O-methylated nucleosides (e.g., 2, 3, 4, 5 or 6 2'-O-methylated nucleosides within 6 nucleosides of the 3' terminus). In some embodiments, the 2'-O-methyl nucleoside is positioned at the 3' terminus of the antisense strand. In some embodiments, 3' terminal region of the antisense strand comprises a plurality of 2'-O-methylated nucleosides (e.g., 2, 3, 4, 5 or 6 2'-0-methylated nucleosides within 6 nucleosides of the 3' terminus). In some embodiments, both the 3' terminal region of the sense strand and the 3' terminal region of the antisense strand comprise a plurality of 2'-O-methylated nucleosides. In some embodiments, the sense strand comprises 2'-O-methylated nucleosides that alternate with unmodified nucleosides. In some embodiments, the sense strand comprises a contiguous sequence of 2, 3, 4, 5, 6, 7 or 8 2'-O-methylated nucleosides that alternate with unmodified nucleosides. In some embodiments, the anti-sense strand comprises 2'-O-methylated nucleosides that alternate with unmodified nucleosides. In some embodiments, the anti-sense strand comprises a contiguous sequence of 2, 3, 4, 5, 6, 7 or 8 2'-O-methylated nucleosides that alternate with unmodified nucleosides.

In some embodiments, the RNA complex comprises a phosphorothioate bond. "Phosphorothioates" (or S-oligos) are a variant of normal DNA in which one of the non-bridging oxygens is replaced by a sulfur. The sulfurization of the internucleotide bond reduces the action of endo- and exonucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1,2-benzodithiol-3-one 1,1-dioxide (BDTD) (see, e.g., Iyer et al., *J. Org. Chem.* 55, 4693-4699, 1990). The latter methods avoid the problem of elemental sulfur's insolubility in most organic solvents and the toxicity of carbon disulfide. The TETD and BDTD methods also yield higher purity phosphorothioates.

In some embodiments, at least 25%, 30%, 35%, 40%, 45%, 50%, 55%, 60%, 65%, 70%, 75%, 80%, 85%, 90% or 95% of the bonds between the ribonucleotides in the sense strand of the RNA complex are phosphorothioate bonds. In some embodiments, all of the bonds between the ribonucleotides in the sense strand of the RNA complex are phosphorothioate bonds.

In some embodiments, at least 25%, 30%, 35%, 40%, 45%, 50%, 55%, 60%, 65%, 70%, 75%, 80%, 85%, 90% or 95% of the bonds between the ribonucleotides in the anti-sense strand of the RNA complex are phosphorothioate bonds. In some embodiments, all of the bonds between the ribonucleotides in the antisense strand of the RNA complex are phosphorothioate bonds.

The RNA complexes described herein may be contacted with a cell or administered to an organism (e.g., a human). Alternatively, constructs and/or vectors encoding the RNA complexes may be contacted with or introduced into a cell or organism. In certain embodiments, a viral, retroviral or lentiviral vector is used.

The RNA complexes described herein can be prepared by any appropriate method known in the art. For example, in some embodiments, the RNA complexes described herein are prepared by chemical synthesis or in vitro transcription.

In certain aspects, provided herein is a pharmaceutical composition comprising an RNA complex provided herein and a pharmaceutically acceptable carrier. In certain embodiments, the pharmaceutical composition is formulated for delivery to the skin (e.g., as a cream or lotion). In certain embodiments, the pharmaceutical composition is formulated for delivery to the lungs (e.g., as an inhaler). In some embodiments, the pharmaceutical composition is formulated for oral or parenteral delivery. In some embodiments, the pharmaceutical composition further comprises a second agent for treatment of atopic dermatitis or asthma. In some embodiments, the second agent is a steroid (e.g., a corticosteroid), a long acting beta agonist (e.g., salmenterol or formoterol), or an immunomodulator. Examples of steroids include hydrocortisone, fluticasone, mudesonide, mometasone, beclomethasone, ciclesonide or flunisolide. Examples of immunomodulators include montelukast, zafirlukast, or zileuton. Two or more steroids, long acting beta agonists, and immunomodulators may be taken in with the pharmaceutical composition.

In some embodiments, the pharmaceutical composition is formulated for delivery to the skin. In some embodiments, the composition is an emulsion, cream, lotion, gel, oil, ointment, aerosol spray, or semi-solid formulation. In some embodiments, the topical formulation comprises a carrier selected from trehalose, malto-dextrin, rice flour, microcrystalline cellulose, magnesium stearate, inositol, fructo-oligosaccharide, gluco-oligosaccharide, dextrose, sucrose, talc, water, physiological salt solution, urea, methanol, ethanol, propanol, butanol, ethylene glycol, propylene glycol, white pertrolatum, isopropyl myristate, lanolin, lanolin alcohol, mineral oil, lavender oil, nasturtium extract oil, sorbitan mono-oleate, cetylstearyl alcohol, hydroxypropyl cellulose, detergent, sucrose stearate, sucrose cocoate, sucrose distearate, 2-ethyl-1,3-hexanediol, polyoxypropylene-15-stearyl ether, glycerol stearate, glycerin, synthetic spermaceti, cetyl alcohol, butylparaben, propylparaben, and methylparaben.

In certain embodiments, the pharmaceutical composition does not comprise a transfection vehicle. In some embodiments, the pharmaceutical composition comprises a delivery vehicle (e.g., liposomes, cationic polymers, cell penetrating peptides (CPPs), protein transduction domains (PTDs), antibodies and/or aptamers). In some embodiments, the composition includes a combination of multiple (e.g., two or more) of the RNA complexes described herein.

Methods of preparing these formulations or compositions include the step of bringing into association an RNA complex described herein with the carrier and, optionally, one or more accessory ingredients. In general, the formulations are prepared by uniformly and intimately bringing into association an agent described herein with liquid carriers.

Therapeutic Methods

In certain aspects, provided herein is a method of inhibiting IL4Rα, TRPA1, or F2RL1 expression by a cell, comprising contacting the cell with an RNA complex provided herein. In some embodiments, the RNA complex is a modified RNA complex and the cell is contacted with the RNA complex in the absence of a transfection vehicle. In some embodiments, the cell is contacted with the RNA complex in the presence of a delivery vehicle (e.g., a liposome, cationic polymer, cell penetrating peptide (CPP), protein transduction domain (PTD), antibody and/or aptamer). In some embodiments, the cell is present in the respiratory tract of a human subject. In some embodiments, the cell is present in the skin of a human subject. In some embodiments, the subject has atopic dermatitis. In some embodiments, the subject has asthma. In some embodiments, the subject is female. In some embodiments, the subject is male.

In certain aspects, provided herein is a method of treating a human subject for atopic dermatitis and/or asthma comprising administering to the subject an RNA complex or pharmaceutical composition provided herein. In certain embodiments, the RNA complex or pharmaceutical composition is administered to the respiratory tract of the subject. In certain embodiments, the RNA complex or pharmaceutical composition is administered to the skin of the subject. In some embodiments, the RNA complex or pharmaceutical composition self-administered by the subject.

In the present methods, an RNA complex described herein can be administered to the subject, for example, as nucleic acid without delivery vehicle (e.g., for cp-asiRNAs), in combination with a delivery reagent, and/or as a nucleic acid comprising sequences that express the RNA complex described herein. In some embodiments, any nucleic acid delivery method known in the art can be used in the methods described herein. Suitable delivery reagents include, but are not limited to, e.g., the Mirus Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. *Nucleic Acids Res.*, 32(13):e109 (2004); Hanai et al. *Ann NY Acad Sci.*, 1082:9-17 (2006); and Kawata et al. *Mol Cancer Ther* 7(9):2904-12 (2008); each of which is incorporated herein in their entirety. Exemplary interfering nucleic acid delivery systems are provided in U.S. Pat. Nos. 8,283,461, 8,313,772, 8,501,930. 8,426,554, 8,268,798 and 8,324,366, each of which is hereby incorporated by reference in its entirety.

In some embodiments of the methods described herein, liposomes are used to deliver an RNA complex described herein to a subject. Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are herein incorporated by reference.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

Opsonization-inhibiting moieties for use in preparing the liposomes described herein are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference.

In some embodiments, opsonization inhibiting moieties suitable for modifying liposomes are water-soluble polymers with a number-average molecular weight from about 500 to about 40,000 daltons, or from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. In some embodiments, the opsonization-inhibiting moiety is a PEG, PPG, or derivatives thereof. Liposomes modified with PEG or PEG-derivatives are sometimes called "PEGylated liposomes."

The pharmaceutical compositions disclosed herein may be delivered by any suitable route of administration, including topically, through inhalation, orally, and parenterally. In certain embodiments, the pharmaceutical compositions are delivered systemically (e.g., via oral or parenteral administration). In certain other embodiments, the pharmaceutical compositions are delivered locally through inhalation into the lungs or topically onto the skin. In some embodiments, the pharmaceutical composition is administered via intradermal injection.

Actual dosage levels of the RNA complexes in the pharmaceutical compositions may be varied so as to obtain an amount of RNA complex that is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician or veterinarian could prescribe and/or administer doses of the agents employed in the pharmaceutical composition at levels lower than that required in order to achieve the desired therapeutic effect and gradually increase the dosage until the desired effect is achieved.

In general, a suitable daily dose of an RNA complex described herein will be that amount of the RNA complex which is the lowest dose effective to produce a therapeutic effect. Such an effective dose will generally depend upon the factors described above.

EXEMPLIFICATION

Example 1: Screening for IL4Rα-Specific Asymmetric Shorter-Duplex Small Interfering RNAs To identify asymmetric shorter-duplex small interfering RNAs (asiRNAs) that inhibit IL4Rα with high efficiency, 73 asiRNAs were synthesized and screened. The nucleic acid sequences of the screened asiRNAs are provided in Table 1.

TABLE 1

Nucleic acid sequences for exemplary IL4Rα-targeting asiRNA.

| SEQ ID NO: | SEQUENCE |
|---|---|
| 1 | IL4Rα #1(S): 5' AUCACCAAGAUUAAGA 3' |
| 2 | IL4Rα #1(AS): 5' UCUUAAUCUUGGUGAUGCUGA 3' |
| 3 | IL4Rα #2(S): 5' UCACCAAGAUUAAGAA 3' |
| 4 | IL4Rα #2(AS): 5' UUCUUAAUCUUGGUGAUGCUG 3' |
| 5 | IL4Rα #3(S): 5' GCCUUCUCAAGCCUGC 3' |
| 6 | IL4Rα #3(AS): 5' GCAGGCUUGAGAAGGCCUUGU 3' |
| 7 | IL4Rα #4(S): 5' CCUUCUCAAGCCUGCU 3' |
| 8 | IL4Rα #4(AS): 5' AGCAGGCUUGAGAAGGCCUUG 3' |
| 9 | IL4Rα #5(S): 5' UGCGUCUCCGACUACA 3' |
| 10 | IL4Rα #5(AS): 5' UGUAGUCGGAGACGCAGGUGG 3' |
| 11 | IL4Rα #6(S): 5' GCGUCUCCGACUACAU 3' |
| 12 | IL4Rα #6(AS): 5' AUGUAGUCGGAGACGCAGGUG 3' |
| 13 | IL4Rα #7(S): 5' GUGGAAGGGCUCCUUC 3' |
| 14 | IL4Rα #7(AS): 5' GAAGGAGCCCUUCCACAGCAG 3' |
| 15 | IL4Rα #8(S): 5' UGGAAGGGCUCCUUCA 3' |
| 16 | IL4Rα #8(AS): 5' UGAAGGAGCCCUUCCACAGCA 3' |
| 17 | IL4Rα #9(S): 5' CAUCACCAAGAUUAAG 3' |
| 18 | IL4Rα #9(AS): 5' CUUAAUCUUGGUGAUGCUGAC 3' |
| 19 | IL4Rα #10(S): 5' CACCAAGAUUAAGAAA 3' |
| 20 | IL4Rα #10(AS): 5' UUUCUUAAUCUUGGUGAUGCU 3' |
| 21 | IL4Rα #11(S): 5' UGGGAUCAGAUUCCCA 3' |
| 22 | IL4Rα #11(AS): 5' UGGGAAUCUGAUCCCACCAUU 3' |
| 23 | IL4Rα #12(S): 5' GGGAUCAGAUUCCCAA 3' |
| 24 | IL4Rα #12(AS): 5' UUGGGAAUCUGAUCCCACCAU 3' |

TABLE 1-continued

Nucleic acid sequences for exemplary IL4Rα-targeting asiRNA.

| SEQ ID NO: | SEQUENCE |
|---|---|
| 25 | IL4Rα #13(S): 5' AAGACAGUCCUCUGGC 3' |
| 26 | IL4Rα #13(AS): 5' GCCAGAGGACUGUCUUGCUGA 3' |
| 27 | IL4Rα #14(S): 5' AGACAGUCCUCUGGCC 3' |
| 28 | IL4Rα #14(AS): 5' GGCCAGAGGACUGUCUUGCUG 3' |
| 29 | IL4Rα #15(S): 5' GACAGUCCUCUGGCCA 3' |
| 30 | IL4Rα #15(AS): 5' UGGCCAGAGGACUGUCUUGCU 3' |
| 31 | IL4Rα #16(S): 5' ACAGUCCUCUGGCCAG 3' |
| 32 | IL4Rα #16(AS): 5' CUGGCCAGAGGACUGUCUUGC 3' |
| 33 | IL4Rα #17(S): 5' CAGUCCUCUGGCCAGA 3' |
| 34 | IL4Rα #17(AS): 5' UCUGGCCAGAGGACUGUCUUG 3' |
| 35 | IL4Rα #18(S): 5' AGUCCUCUGGCCAGAG 3' |
| 36 | IL4Rα #18(AS): 5' CUCUGGCCAGAGGACUGUCUU 3' |
| 37 | IL4Rα #19(S): 5' GUCCUCUGGCCAGAGA 3' |
| 38 | IL4Rα #19(AS): 5' UCUCUGGCCAGAGGACUGUCU 3' |
| 39 | IL4Rα #20(S): 5' CUCCAGCAUGGGGCAG 3' |
| 40 | IL4Rα #20(AS): 5' CUGCCCCAUGCUGGAGGACAU 3' |
| 41 | IL4Rα #21(S): 5' GGCUAUCAGGAGUUUG 3' |
| 42 | IL4Rα #21(AS): 5' CAAACUCCUGAUAGCCACUGG 3' |
| 43 | IL4Rα #22(S): 5' GCUAUCAGGAGUUUGU 3' |
| 44 | IL4Rα #22(AS): 5' ACAAACUCCUGAUAGCCACUG 3' |
| 45 | IL4Rα #23(S): 5' CUUCUCAAGCCUGCUU 3' |
| 46 | IL4Rα #23(AS): 5' AAGCAGGCUUGAGAAGGCCUU 3' |
| 47 | IL4Rα #24(S): 5' AAUGGGGUGGCUUUGC 3' |
| 48 | IL4Rα #24(AS): 5' GCAAAGCCACCCCAUUGGGAG 3' |
| 49 | IL4Rα #25(S): 5' AUGGGGUGGCUUUGCU 3' |
| 50 | IL4Rα #25(AS): 5' AGCAAAGCCACCCCAUUGGGA 3' |
| 51 | IL4Rα #26(S): 5' CGUCUCCGACUACAUG 3' |
| 52 | IL4Rα #26(AS): 5' CAUGUAGUCGGAGACGCAGGU 3' |
| 53 | IL4Rα #27(S): 5' GACAGUUCACACCAAU 3' |
| 54 | IL4Rα #27(AS): 5' AUUGGUGUGAACUGUCAGGUU 3' |
| 55 | IL4Rα #28(S): 5' ACAGUUCACACCAAUG 3' |
| 56 | IL4Rα #28(AS): 5' CAUUGGUGUGAACUGUCAGGU 3' |
| 57 | IL4Rα #29(S): 5' CAGUUCACACCAAUGU 3' |
| 58 | IL4Rα #29(AS): 5' ACAUUGGUGUGAACUGUCAGG 3' |
| 59 | IL4Rα #30(S): 5' AGUUCACACCAAUGUC 3' |
| 60 | IL4Rα #30(AS): 5' GACAUUGGUGUGAACUGUCAG 3' |
| 61 | IL4Rα #31(S): 5' CUGGAGUGAGUGGAGC 3' |

TABLE 1-continued

Nucleic acid sequences for exemplary IL4Rα-targeting asiRNA.

| SEQ ID NO: | SEQUENCE |
|---|---|
| 62 | IL4Rα #31(AS): 5' GCUCCACUCACUCCAGGUGGU 3' |
| 63 | IL4Rα #32(S): 5' CAGCAUCACCAAGAUU 3' |
| 64 | IL4Rα #32(AS): 5' AAUCUUGGUGAUGCUGACAUA 3' |
| 65 | IL4Rα #33(S): 5' AGCAUCACCAAGAUUA 3' |
| 66 | IL4Rα #33(AS): 5' UAAUCUUGGUGAUGCUGACAU 3' |
| 67 | IL4Rα #34(S): 5' GCAUCACCAAGAUUAA 3' |
| 68 | IL4Rα #34(AS): 5' UUAAUCUUGGUGAUGCUGACA 3' |
| 69 | IL4Rα #35(S): 5' UAAGAAAGAAUGGUGG 3' |
| 70 | IL4Rα #35(AS): 5' CCACCAUUCUUUCUUAAUCUU 3' |
| 71 | IL4Rα #36(S): 5' AAGAAAGAAUGGUGGG 3' |
| 72 | IL4Rα #36(AS): 5' CCCACCAUUCUUUCUUAAUCU 3' |
| 73 | IL4Rα #37(S): 5' AGAAAGAAUGGUGGGA 3' |
| 74 | IL4Rα #37(AS): 5' UCCCACCAUUCUUUCUUAAUC 3' |
| 75 | IL4Rα #38(S): 5' GAUUCCCAACCCAGCC 3' |
| 76 | IL4Rα #38(AS): 5' GGCUGGGUUGGGAAUCUGAUC 3' |
| 77 | IL4Rα #39(S): 5' AGCAAGACAGUCCUCU 3' |
| 78 | IL4Rα #39(AS): 5' AGAGGACUGUCUUGCUGAUCU 3' |
| 79 | IL4Rα #40(S): 5' GCAAGACAGUCCUCUG 3' |
| 80 | IL4Rα #40(AS): 5' CAGAGGACUGUCUUGCUGAUC 3' |
| 81 | IL4Rα #41(S): 5' CAAGACAGUCCUCUGG 3' |
| 82 | IL4Rα #41(AS): 5' CCAGAGGACUGUCUUGCUGAU 3' |
| 83 | IL4Rα #42(S): 5' GUUGUUUGAGGCCCCG 3' |
| 84 | IL4Rα #42(AS): 5' CGGGGCCUCAAACAACUCCAC 3' |
| 85 | IL4Rα #43(S): 5' AACAGAGAGCCUGUUC 3' |
| 86 | IL4Rα #43(AS): 5' GAACAGGCUCUCUGUUAGCCG 3' |
| 87 | IL4Rα #44(S): 5' CUGGGAGCAGAUCCUC 3' |
| 88 | IL4Rα #44(AS): 5' GAGGAUCUGCUCCCAGGUUUC 3' |
| 89 | IL4Rα #45(S): 5' CUAUCAGGAGUUUGUA 3' |
| 90 | IL4Rα #45(AS): 5' UACAAACUCCUGAUAGCCACU 3' |
| 91 | IL4Rα #46(S): 5' GGCUGGUUACAAGGCC 3' |
| 92 | IL4Rα #46(AS): 5' GGCCUUGUAACCAGCCUCUCC 3' |
| 93 | IL4Rα #47(S): 5' GCUGGUUACAAGGCCU 3' |
| 94 | IL4Rα #47(AS): 5' AGGCCUUGUAACCAGCCUCUC 3' |
| 95 | IL4Rα #48(S): 5' CUGGUUACAAGGCCUU 3' |
| 96 | IL4Rα #48(AS): 5' AAGGCCUUGUAACCAGCCUCU 3' |
| 97 | IL4Rα #49(S): 5' UGGUUACAAGGCCUUC 3' |

TABLE 1-continued

Nucleic acid sequences for exemplary IL4Rα-targeting asiRNA.

| SEQ ID NO: | SEQUENCE |
|---|---|
| 98 | IL4Rα #49(AS): 5' GAAGGCCUUGUAACCAGCCUC 3' |
| 99 | IL4Rα #50(S): 5' GGUUACAAGGCCUUCU 3' |
| 100 | IL4Rα #50(AS): 5' AGAAGGCCUUGUAACCAGCCU 3' |
| 101 | IL4Rα #51(S): 5' GUUACAAGGCCUUCUC 3' |
| 102 | IL4Rα #51(AS): 5' GAGAAGGCCUUGUAACCAGCC 3' |
| 103 | IL4Rα #52(S): 5' UUACAAGGCCUUCUCA 3' |
| 104 | IL4Rα #52(AS): 5' UGAGAAGGCCUUGUAACCAGC 3' |
| 105 | IL4Rα #53(S): 5' GUGCGGCCACCUGAAA 3' |
| 106 | IL4Rα #53(AS): 5' UUUCAGGUGGCCGCACAGGUG 3' |
| 107 | IL4Rα #54(S): 5' GCUGUGGCUGCUGCUG 3' |
| 108 | IL4Rα #54(AS): 5' CAGCAGCAGCCACAGCAAGGA 3' |
| 109 | IL4Rα #55(S): 5' AGCCGAGCCUAGAAAC 3' |
| 110 | IL4Rα #55(AS): 5' GUUUCUAGGCUCGGCUUCUAG 3' |
| 111 | IL4Rα #56(S): 5' GGGAACAUGAAGGUCU 3' |
| 112 | IL4Rα #56(AS): 5' AGACCUUCAUGUUCCCAGAGC 3' |
| 113 | IL4Rα #57(S): 5' CUUGCAGGAGCCCACC 3' |
| 114 | IL4Rα #57(AS): 5' GGUGGGCUCCUGCAAGACCUU 3' |
| 115 | IL4Rα #58(S): 5' UUGCAGGAGCCCACCU 3' |
| 116 | IL4Rα #58(AS): 5' AGGUGGGCUCCUGCAAGACCU 3' |
| 117 | IL4Rα #59(S): 5' AGUUCACACCAAUGUC 3' |
| 118 | IL4Rα #59(AS): 5' GACAUUGGUGUGAACUGUCAG 3' |
| 119 | IL4Rα #60(S): 5' UUUCAGAAUCUAUAAC 3' |
| 120 | IL4Rα #60(AS): 5' GUUAUAGAUUCUGAAAUCGC 3' |
| 121 | IL4Rα #61(S): 5' UAUAACGUGACCUACC 3' |
| 122 | IL4Rα #61(AS): 5' GGUAGGUCACGUUAUAGAUUC 3' |
| 123 | IL4Rα #62(S): 5' CACCUGGAGUGAGUGG 3' |
| 124 | IL4Rα #62(AS): 5' CCACUCACUCCAGGUGGUGUU 3' |
| 125 | IL4Rα #63(S): 5' ACCUGGAGUGAGUGGA 3' |
| 126 | IL4Rα #63(AS): 5' UCCACUCACUCCAGGUGGUGU 3' |
| 127 | IL4Rα #64(S): 5' UGUGCUAUGUCAGCAU 3' |
| 128 | IL4Rα #64(AS): 5' AUGCUGACAUAGCACAACAGG 3' |
| 129 | IL4Rα #65(S): 5' GUCAGCAUCACCAAGA 3' |
| 130 | IL4Rα #65(AS): 5' UCUGGUGAUGCUGACAUAGC 3' |
| 131 | IL4Rα #66(S): 5' UCAGCAUCACCAAGAU 3' |
| 132 | IL4Rα #66(AS): 5' AUCUUGGUGAUGCUGACAUAG 3' |
| 133 | IL4Rα #67(S): 5' UGGUGGGAUCAGAUUC 3' |
| 134 | IL4Rα #67(AS): 5' GAAUCUGAUCCCACCAUUCUU 3' |

TABLE 1-continued

Nucleic acid sequences for exemplary IL4Rα-targeting asiRNA.

| SEQ ID NO: | SEQUENCE |
|---|---|
| 135 | IL4Rα #68(S): 5' GGUGGGAUCAGAUUCC 3' |
| 136 | IL4Rα #68(AS): 5' GGAAUCUGAUCCCACCAUUCU 3' |
| 137 | IL4Rα #69(S): 5' GUGCCCACACUGGAAG 3' |
| 138 | IL4Rα #69(AS): 5' CUUCCAGUGUGGGCACUUGGC 3' |
| 139 | IL4Rα #70(S): 5' CUGGAAGAAUUGUCUU 3' |
| 140 | IL4Rα #70(AS): 5' AAGACAAUUCUUCCAGUGUGG 3' |
| 141 | IL4Rα #71(S): 5' GUCCUCCAGCAUGGGG 3' |
| 142 | IL4Rα #71(AS): 5' CCCCAUGCUGGAGGACAUUUC 3' |
| 143 | IL4Rα #72(S): 5' AGUGGCUAUCAGGAGU 3' |
| 144 | IL4Rα #72(AS): 5' ACUCCUGAUAGCCACUGGUGG 3' |
| 145 | IL4Rα #73(S): 5' GUGGCUAUCAGGAGUU 3' |
| 146 | IL4Rα #73(AS): 5' AACUCCUGAUAGCCACUGGUG 3' |

The asiRNAs listed in Table 1 were incubated at 95° C. for 5 minutes and at 37° C. for 1 hour in annealing buffer (Bioneer Inc. Korea). Proper strand annealing was confirmed via gel electrophoresis using a UV transilluminator. For the screen, A549 cells (ATCC) that had been cultured in Dulbecco's modified Eagle's medium (DMEM, Gibco) containing 10% fetal bovine serum (FBS, Gibco), 100 units/ml Penicillin and 100 μg/ml Streptomycin in a 100 mm cell culture dish. One day prior to transfection, 5×10³ A549 cells were seeded in 96-well plates. The A549 cells were transfected with 0.1 nM of the asiRNAs using RNAiMAX (Invitrogen Inc.) according to the manufacturer's instructions.

The IL4Rα mRNA levels in the transfected cells were measured 24 hours after transfection using qRT-PCR. Specifically, total RNA was extracted and synthesized into cDNA using Super Prep Cell Lysis & RT kit for qPCR (TOYOBO) according to manufacturer's instructions. Amplification of the IL4Rα gene was detected using IL4Rα TaqMan® Probe (Hs00166237_m1). 18S was amplified as an internal control using 18S TaqMan® Probe (Hs03928985_g1).

The level of IL4Rα inhibition by each of the 73 asiRNAs is depicted in FIG. 1. Fifteen of the asiRNA sequences, #5, #6, #20, #32, #38, #40, #41, #44, #48, #56, #58, #59, #64, #67 and #72, were selected for use in follow-up studies.

Example 2: Inhibition of IL4Rα mRNA Expression Using IL4Rα-Targeting asiRNAs

The asiRNA sequences selected in Example 1 were tested for their ability to inhibit IL4Rα mRNA expression.

The asiRNAs were incubated at 95° C. for 5 minutes and at 37° C. for 1 hour in annealing buffer (Bioneer Inc. Korea). Proper strand annealing was confirmed via gel electrophoresis using a UV transilluminator. For the screen, A549 cells (ATCC) that had been cultured in Dulbecco's modified Eagle's medium (Gibco) containing 10% fetal bovine serum (Gibco) and 100 units/ml Penicillin and 100 μg/ml Streptomycin in a 100 mm cell culture dish. One day prior to transfection, 2.5×10⁴ A549 cells were seeded in 24-well plates. The A549 cells were transfected with asiRNAs using RNAiMAX (Invitrogen Inc.) according to the manufacturer's instructions.

IL4Rα mRNA levels in A549 cells were determined using qRT-PCR 24 hours after asiRNA transfection. Specifically, total RNA was extracted using RNAiPlus® (TaKaRa) and then 500 ng of the extracted RNA was used for cDNA synthesis using the High-capacity cDNA reverse transcription kit (Applied Biosystems), according to the manufacturer's instructions. Amplification of the IL4Rα was detected using IL4Rα TaqMan® Probe (Hs00166237_m1). 18S RNA was amplified as an internal control using 18S TaqMan® Probe (Hs03928985_g1).

The level of IL4Rα inhibition of the 15 asiRNAs is provided in FIG. 2. AsiRNAs #5 and #6, which exhibited 40-50% inhibition of IL4Rα mRNA, were selected for use in follow-up studies.

Example 3: Inhibition of IL4Rα Protein Expression Using IL4Rα-Targeting asiRNAs

The two asiRNAs selected in Example 2 were tested for their ability to inhibit IL4Rα protein expression.

The asiRNAs were incubated at 95° C. for 5 minutes and at 37° C. for 1 hour in annealing buffer (Bioneer Inc. Korea). Proper strand annealing was confirmed via gel electrophoresis using a UV transilluminator. For the screen, A549 cells (ATCC) that had been cultured in Dulbecco's modified Eagle's medium (Gibco) containing 10% fetal bovine serum (Gibco), 100 units/ml Penicillin and 100 μg/ml Streptomycin in a 100 mm cell culture dish. One day prior to transfection, 2.5×10⁴ A549 cells were seeded in 24-well plates. The A549 cells were transfected with 1 nM of the asiRNAs using RNAiMAX (Invitrogen Inc.) according to the manufacturer's instructions.

Figure 3:
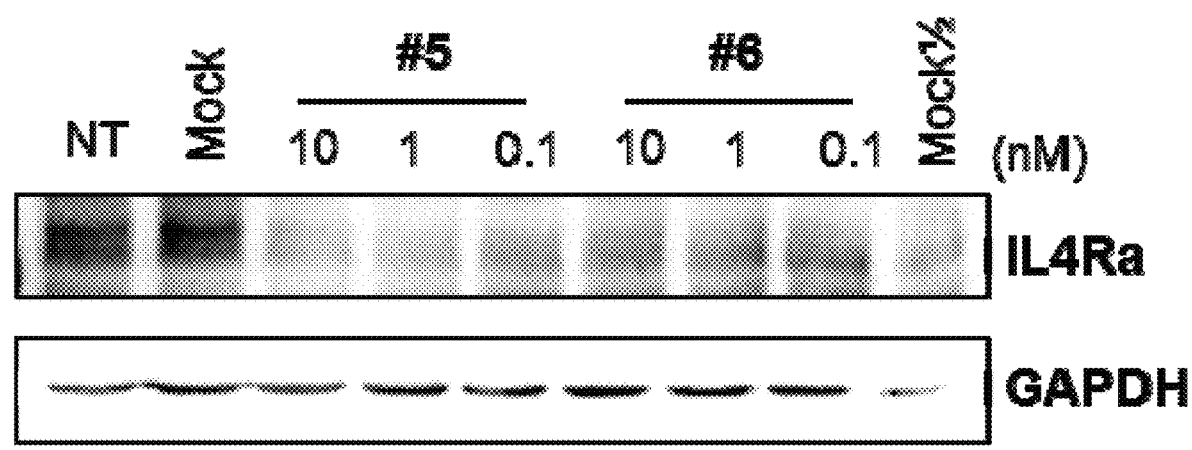
FIG. 3 shows the gene silencing effects of 2 exemplary asiRNAs that target IL4Rα.

IL4Rα protein levels were determined via western blot 48 hours after asiRNA transfection. Briefly, the transfected A549 cells were lysed with 1% SDS lysis buffer (1% SDS, 100 mM Tris pH 8.0). 15 μg of the total protein extract was loaded onto an 8% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 3% BSA (Bioworld) and then incubated overnight at 4° C. in 3% BSA containing anti-IL4Rα antibody (Acris) and anti-GAPDH antibody (Santa Cruz). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL substrate (Thermo scientific) for 1 minute. The IL4Rα and GAPDH bands were then imaged using a Chemidoc instrument (Bio-rad). The results of the western blot are depicted in FIG. 3.

Example 4: Chemical Modification of asiRNAs for Self-Delivery

Chemical modifications were applied to the asiRNAs and the cellular delivery of the modified asiRNAs was tested in the absence of other delivery reagent. As described below, certain of the modifications improved endocytosis and stability of asiRNAs. Such cell penetrating asiRNAs (cp-asiRNAs) are able to be delivered into the cell in the absence of a delivery reagent.

Potential cp-asiRNA (Table 2) were screened for IL4Rα mRNA and protein inhibition in A549 cells. Each potential cp-asiRNA was incubated with A549 cells at 1 μM and 3 μM without a delivery reagent and IL4Rα expression levels were measured by qRT-PCR and western blot.

TaqMan® Probe (Hs00166237_m1). 18S was amplified as an internal control using 18S TaqMan® Probe (Hs03928985_g1).

IL4Rα protein levels were determined via western blot 72 hours after cp-asiRNA treatment. Briefly, the transfected A549 cells were lysed with 1% SDS lysis buffer (1% SDS, 100 mM Tris pH 8.0). 15 μg of the total protein extract of A549 cells were loaded onto an 8% SDS-PAGE gel and electrophoresed at 120 V. After electrophoresis, the proteins were transferred to PVDF membrane (Bio-rad) already activated by methanol (Merck) for 1 hour at 300 mA. The

TABLE 2

Modified asiRNA sequences tested for self-delivery and IL4Rα inhibition.
(m = 2'-O-Methyl RNA. * = phosphorothioate bond.)

| Name | SEQ ID NO: | SEQUENCE |
|---|---|---|
| IL4Rα cp-asiRNA #5(s) | 147 | 5' mUGmCGmUCmUCmCGmACmUA*mC*A*Cholesterol 3' |
| IL4Rα cp-asiRNA #5 21(2,4)(AS) | 148 | 5' UGUAGUCGGAGACGmCmAG*G*U*G*G 3' |
| IL4Rα cp-asiRNA #6(s) | 149 | 5' mGCmGUmCUmCCmGAmCUmAC*mA*U*Cholesterol 3' |
| IL4Rα cp-asiRNA #6 21(2,4)(AS) | 150 | 5' AUGUAGUCGGAGACmGmCA*G*G*U*G 3' |
| IL4Rα cp-asiRNA #6 21(7,4)(AS) | 151 | 5' AUGUAGUCGGAGACmGmCmA*mG*mG*mU*mG 3' |

A549 cells (ATCC) that had been cultured in Dulbecco's modified Eagle's medium (DMEM, Gibco) containing 10% fetal bovine serum (FBS, Gibco) and 100 units/ml Penicillin and 100 μg/ml Streptomycin in a 100 mm cell culture dish.

The potential cp-asiRNAs listed in Table 2 were incubated at 95° C. for 5 minutes and at 37° C. for 1 hour in Opti-MEM (Gibco). Proper strand annealing of the potential cp-asiRNAs was confirmed by gel electrophoresis using a UV transilluminator.

One day prior to treatment, $2.5 \times 10^4$ A549 cells were seeded in 24-well plates. Immediately before treatment, the A549 cells were washed with Dulbecco's modified Eagle's medium (DMEM, Gibco) then cultured in the presence of the potential cp-asiRNAs in OPTI-MEM buffer for 24 hours, at each point the cp-asiRNA containing OPTI-MEM media was replaced with a serum containing media.

Total RNA was extracted 48 hours after cp-asiRNA treatment, using RNAiPlus® (TaKaRa) and then 500 ng of the extracted RNA was used for cDNA synthesis using the High-capacity cDNA reverse transcription kit (Applied Biosystems), according to the manufacturer's instructions. Amplification of the IL4Rα was detected using IL4Rα membrane was blocked for 1 hour at the room temperature with 3% BSA (Bioworld) and then incubated overnight at 4° C. in 3% BSA containing anti-IL4Rα antibody (Acris) and anti-GAPDH antibody (Santa Cruz). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1× ECL substrate (Thermo scientific) for 1 minute. The IL4Rα and GAPDH bands were then imaged using a Chemidoc instrument (Bio-rad).

Figure 4:
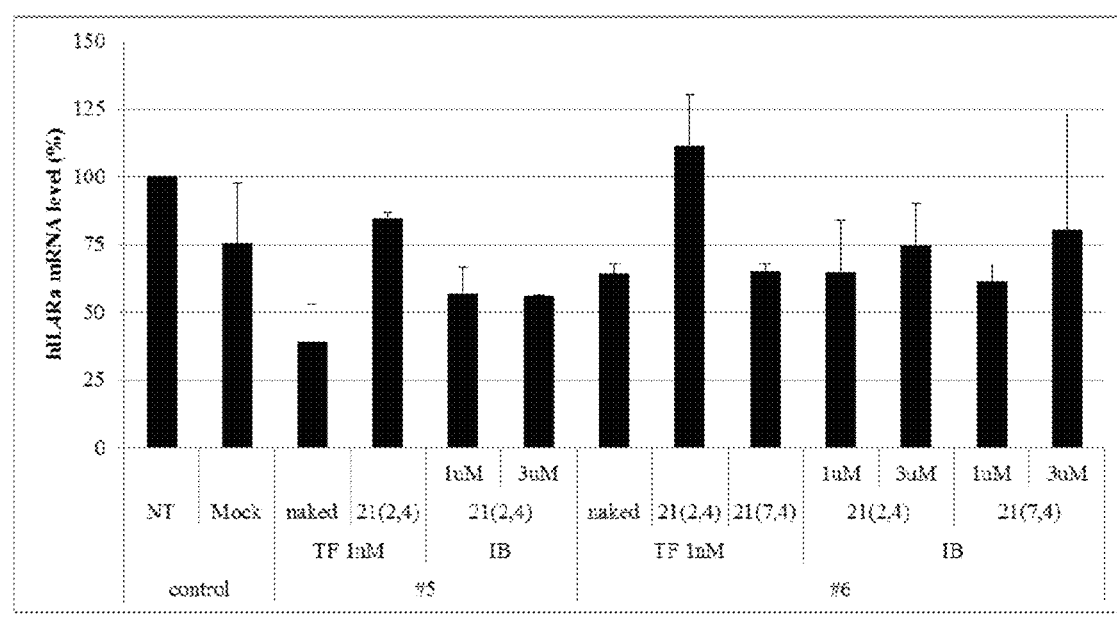
FIG. 4 shows the gene silencing efficiency of exemplary IL4Rα-targeting cell-penetrating asiRNAs (IL4Rα cp-asiRNAs) to which various chemical modifications have been applied.
Figure 5:
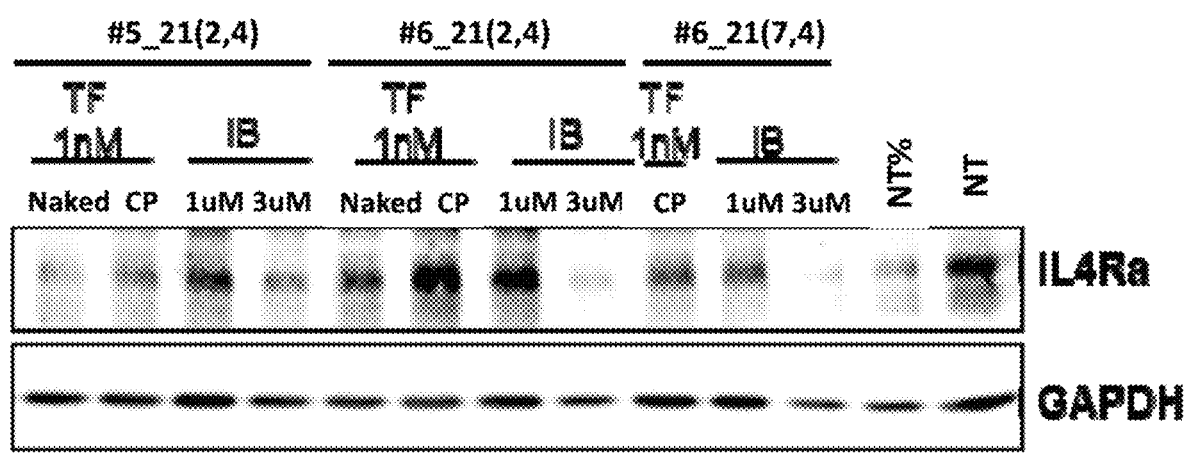
FIG. 5 shows the inhibition of IL4Rα protein expression by exemplary cp-asiRNAs.

The levels of IL4Rα inhibition of three potential cp-asiRNAs is provided in FIG. 4 and FIG. 5. As the result, cp-asiRNA #5_21(2, 4) and cp-asiRNA #6_21(2, 4) were selected for further studies.

Example 5: Additional Chemical Modification of cp-asiRNA Structures

Other potential IL4Rα cp-asiRNA structures having different strand length was synthesized and tested for its ability to inhibit IL4Rα expression (Table 3).

TABLE 3

Additional cp-asiRNA sequence.
(m = 2'-O-Methyl RNA. * = phosphorothioate bond.)

| Name | SEQ ID NO: | SEQUENCE |
|---|---|---|
| IL4Rα cp-asiRNA #5(s) | 152 | 5' mUGmCGmUCmUCmCGmACmUA*mC*A*Cholesterol 3' |
| IL4Rα cp-asiRNA #5 19(2,4)(AS) | 153 | 5' UGUAGUCGGAGACGmC*mA*G*G*U 3' |
| IL4Rα cp-asiRNA #5 21(2,4)(AS) | 154 | 5' UGUAGUCGGAGACGmCmAG*G*U*G*G 3' |
| IL4Rα cp-asiRNA #6(s) | 155 | 5' mGCmGUmCUmCCmGAmCUmAC*mA*U*Cholesterol 3' |

TABLE 3-continued

Additional cp-asiRNA sequence.
(m = 2'-O-Methyl RNA. * = phosphorothioate bond.)

| Name | SEQ ID NO: | SEQUENCE |
|---|---|---|
| IL4Rα cp-asiRNA #6 19(2,4)(AS) | 156 | 5' AUGUAGUCGGAGACmG*mC*A*G*G 3' |
| IL4Rα cp-asiRNA #6 21(2,4)(AS) | 157 | 5' AUGUAGUCGGAGACmGmCA*G*G*U*G 3' |

A549 cells (ATCC) that had been cultured in Dulbecco's modified Eagle's medium (DMEM, Gibco) containing 10% fetal bovine serum (FBS, Gibco) and 100 units/ml Penicillin and 100 µg/ml Streptomycin in a 100 mm cell culture dish.

The potential cp-asiRNAs listed in Table 3 were incubated at 95° C. for 5 minutes and at 37° C. for 1 hour in Opti-MEM (Gibco). Proper strand annealing of the potential cp-asiRNAs was confirmed by gel electrophoresis using a UV transilluminator.

One day prior to treatment, $2.5 \times 10^4$ A549 cells were seeded in 24-well plates. Immediately before treatment, the A549 cells were washed with Dulbecco's modified Eagle's medium (DMEM, Gibco) then cultured in the presence of the potential cp-asiRNAs in OPTI-MEM buffer for 24 hours, at each point the cp-asiRNA containing OPTI-MEM media was replaced with a serum containing media.

Total RNA was extracted 48 hours after cp-asiRNA treatment, using RNAiPlus® (TaKaRa) and then 500 ng of the extracted RNA was used for cDNA synthesis using the High-capacity cDNA reverse transcription kit (Applied Biosystems), according to the manufacturer's instructions. Amplification of the IL4Rα was detected using IL4Rα TaqMan® Probe (Hs00166237_m1). 18S was amplified as an internal control using 18S TaqMan® Probe (Hs03928985_g1).

IL4Rα protein levels were determined via western blot 72 hours after cp-asiRNA treatment. Briefly, the transfected A549 cells were lysed with 1% SDS lysis buffer (1% SDS, 100 mM Tris pH 8.0). 15 µg of the total protein extract of A549 cells were loaded onto an 8% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 3% BSA (Bioworld) and then incubated overnight at 4° C. in 3% BSA containing anti-IL4Rα antibody (Acris) and anti-GAPDH antibody (Santa Cruz). The membrane was then washed with 1xTBST for 10 minutes three times and was incubated for 1 hour at the room temperature in 5% skim milk with HRP-conjugated secondary antibody. The membrane was washed with 1xTBST for 10 minutes and treated with 1x ECL substrate (Thermo scientific) for 1 minute. The IL4Rα and GAPDH bands were then imaged using a Chemidoc instrument (Bio-rad).

Figure 6:
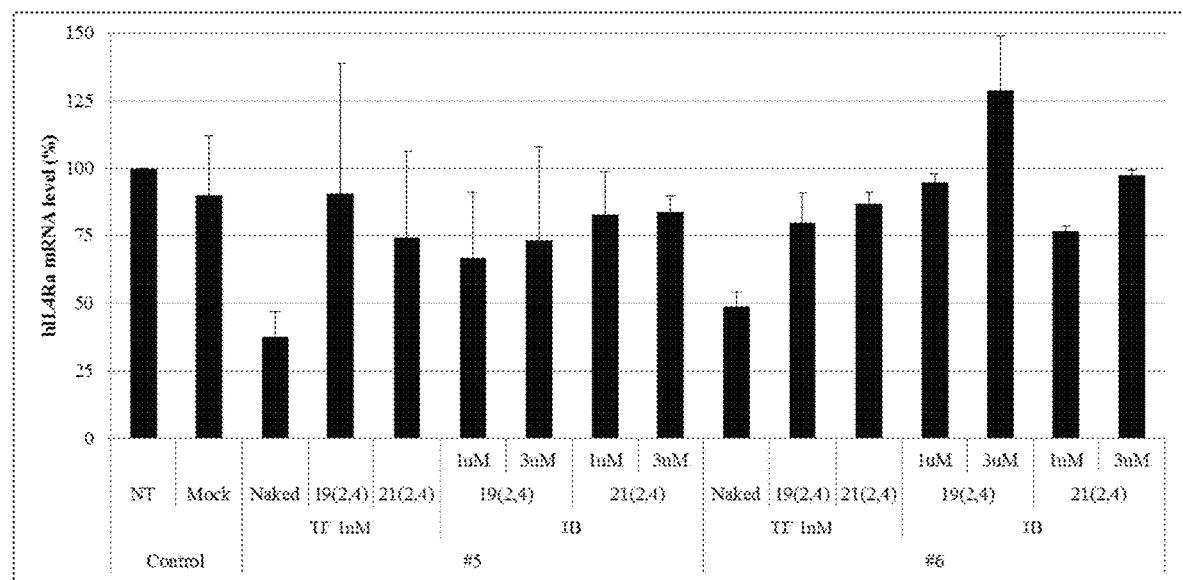
FIG. 6 shows the gene silencing efficiency of 4 cp-asiRNAs of different antisense strand lengths (19 or 21 nucleotides).
Figure 7:
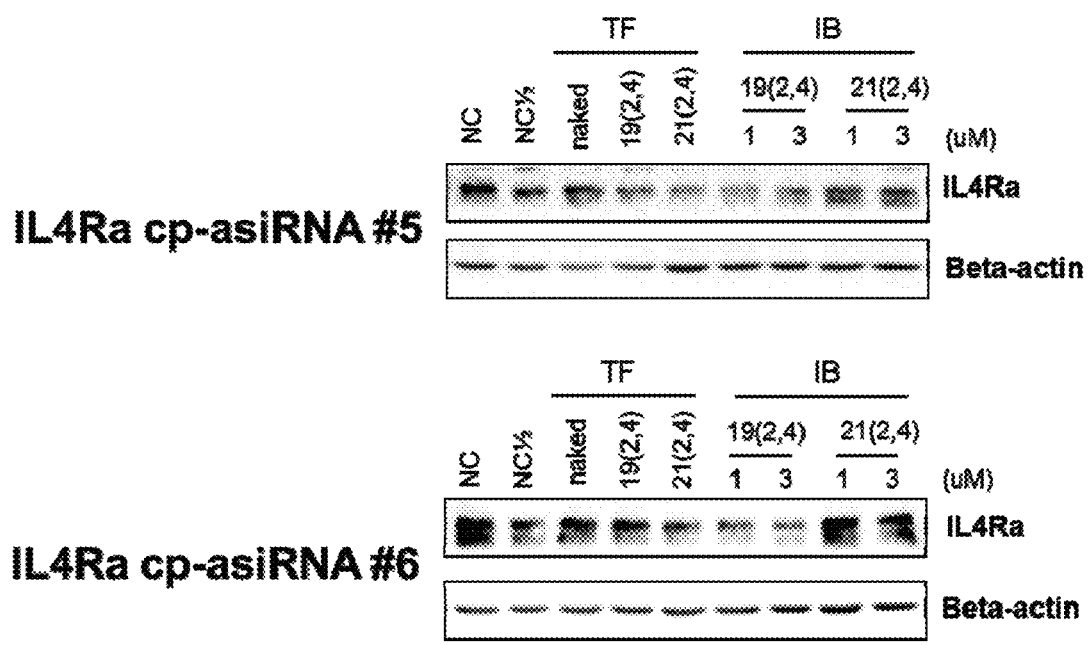
FIG. 7 shows the inhibition of IL4Rα protein expression by 4 exemplary cp-asiRNAs.

As shown the FIG. 6 and FIG. 7, cp-asiRNAs with different antisense strand lengths (21 or 19 nucleotides) exhibited the similar mRNA levels of IL4Rα inhibition.

Example 6: Screening for TRPA1-Specific Asymmetric Shorter-Duplex Small Interfering RNAs To identify asymmetric shorter-duplex small interfering RNAs (asiRNAs) that inhibit TRPA1 with high efficiency, 102 asiRNAs were synthesized and screened. The nucleic acid sequences of the screened asiRNAs are provided in Table 4.

TABLE 4

Nucleic acid sequences for exemplary TRPA1-targeting asiRNA.

| SEQ ID NO: | SEQUENCE |
|---|---|
| 158 | TRPA1#1(S): 5' UGAAGGACGCUCUCCA 3' |
| 159 | TRPA1#1(AS): 5' UGGAGAGCGUCCUUCAGAAUC 3' |
| 160 | TRPA1#2(S): 5' GAAGGACGCUCUCCAC 3' |
| 161 | TRPA1#2(AS): 5' GUGGAGAGCGUCCUUCAGAAU 3' |
| 162 | TRPA1#3(S): 5' UGAAGGACGCUCUCCA 3' |
| 163 | TRPA1#3(AS): 5' UGGAGAGCGUCCUUCAGAAUC 3' |
| 164 | TRPA1#4(S): 5' AGGACGCUCUCCACUU 3' |
| 165 | TRPA1#4(AS): 5' AAGUGGAGAGCGUCCUUCAGA 3' |
| 166 | TRPA1#5(S): 5' GGACGCUCUCCACUUA 3' |
| 167 | TRPA1#5(AS): 5' UAAGUGGAGAGCGUCCUUCAG 3' |
| 168 | TRPA1#6(S): 5' GACGCUCUCCACUUAU 3' |
| 169 | TRPA1#6(AS): 5' AUAAGUGGAGAGCGUCCUUCA 3' |
| 170 | TRPA1#7(S): 5' UUUUGCAGCCAGUUAU 3' |
| 171 | TRPA1#7(AS): 5' AUAACUGGCUGCAAAAUGCAG 3' |
| 172 | TRPA1#8(S): 5' UUUGCAGCCAGUUAUG 3' |
| 173 | TRPA1#8(AS): 5' CAUAACUGGCUGCAAAAUGCA 3' |
| 174 | TRPA1#9(S): 5' UUGCAGCCAGUUAUGG 3' |
| 175 | TRPA1#9(AS): 5' CCAUAACUGGCUGCAAAAUGC 3' |
| 176 | TRPA1#10(S): 5' UGCAGCCAGUUAUGGG 3' |
| 177 | TRPA1#10(AS): 5' CCCAUAACUGGCUGCAAAAUG 3' |
| 178 | TRPA1#11(S): 5' GCAGCCAGUUAUGGGC 3' |
| 179 | TRPA1#11(AS): 5' GCCCAUAACUGGCUGCAAAAU 3' |
| 180 | TRPA1#12(S): 5' CAGCCAGUUAUGGGCG 3' |
| 181 | TRPA1#12(AS): 5' CGCCCAUAACUGGCUGCAAAA 3' |
| 182 | TRPA1#13(S): 5' CAUAAGUGAUACGAGG 3' |
| 183 | TRPA1#13(AS): 5' CCUCGUAUCACUUAUGUCUUG 3' |
| 184 | TRPA1#14(S): 5' AUAAGUGAUACGAGGC 3' |

TABLE 4-continued

Nucleic acid sequences for exemplary TRPA1-targeting asiRNA.

| SEQ ID NO: | SEQUENCE |
|---|---|
| 185 | TRPA1#14(AS): 5' AAGACAUAAGUGAUACGAGGC 3' |
| 186 | TRPA1#15(S): 5' UAAGUGAUACGAGGCU 3' |
| 187 | TRPA1#15(AS): 5' AGCCUCGUAUCACUUAUGUCU 3' |
| 188 | TRPA1#16(S): 5' AAGUGAUACGAGGCUU 3' |
| 189 | TRPA1#16(AS): 5' AAGCCUCGUAUCACUUAUGUC 3' |
| 190 | TRPA1#17(S): 5' CAGUGACCACAAUGGC 3' |
| 191 | TRPA1#17(AS): 5' GCCAUUGUGGUCACUGAGAAA 3' |
| 192 | TRPA1#18(S): 5' AGUGACCACAAUGGCU 3' |
| 193 | TRPA1#18(AS): 5' AGCCAUUGUGGUCACUGAGAA 3' |
| 194 | TRPA1#19(S): 5' GUGACCACAAUGGCUG 3' |
| 195 | TRPA1#19(AS): 5' CAGCCAUUGUGGUCACUGAGA 3' |
| 196 | TRPA1#20(S): 5' UGACCACAAUGGCUGG 3' |
| 197 | TRPA1#20(AS): 5' CCAGCCAUUGUGGUCACUGAG 3' |
| 198 | TRPA1#21(S): 5' GACCACAAUGGCUGGA 3' |
| 199 | TRPA1#21(AS): 5' UCCAGCCAUUGUGGUCACUGA 3' |
| 200 | TRPA1#22(S): 5' ACCACAAUGGCUGGAC 3' |
| 201 | TRPA1#22(AS): 5' GUCCAGCCAUUGUGGUCACUG 3' |
| 202 | TRPA1#23(S): 5' CACUCAGACCAUGAAG 3' |
| 203 | TRPA1#23(AS): 5' CUUCAUGGUCUGAGUGUACCC 3' |
| 204 | TRPA1#24(S): 5' ACUCAGACCAUGAAGG 3' |
| 205 | TRPA1#24(AS): 5' CCUUCAUGGUCUGAGUGUACC 3' |
| 206 | TRPA1#25(S): 5' CUCAGACCAUGAAGGU 3' |
| 207 | TRPA1#25(AS): 5' ACCUUCAUGGUCUGAGUGUAC 3' |
| 208 | TRPA1#26(S): 5' UCAGACCAUGAAGGUC 3' |
| 209 | TRPA1#26(AS): 5' GACCUUCAUGGUCUGAGUGUA 3' |
| 210 | TRPA1#27(S): 5' CAGACCAUGAAGGUCA 3' |
| 211 | TRPA1#27(AS): 5' UGACCUUCAUGGUCUGAGUGU 3' |
| 212 | TRPA1#28(S): 5' AGACCAUGAAGGUCAU 3' |
| 213 | TRPA1#28(AS): 5' AUGACCUUCAUGGUCUGAGUG 3' |
| 214 | TRPA1#29(S): 5' GACCAUGAAGGUCAUU 3' |
| 215 | TRPA1#29(AS): 5' AAUGACCUUCAUGGUCUGAGU 3' |
| 216 | TRPA1#30(S): 5' ACCAUGAAGGUCAUUC 3' |
| 217 | TRPA1#30(AS): 5' GAAUGACCUUCAUGGUCUGAG 3' |
| 218 | TRPA1#31(S): 5' CCAUGAAGGUCAUUCU 3' |
| 219 | TRPA1#31(AS): 5' AGAAUGACCUUCAUGGUCUGA 3' |
| 220 | TRPA1#32(S): 5' CAUGAAGGUCAUUCUU 3' |
| 221 | TRPA1#32(AS): 5' AAGAAUGACCUUCAUGGUCUG 3' |
| 222 | TRPA1#33(S): 5' AUGAAGGUCAUUCUUG 3' |
| 223 | TRPA1#33(AS): 5' CAAGAAUGACCUUCAUGGUCU 3' |
| 224 | TRPA1#34(S): 5' UGAAGGUCAUUCUUGA 3' |
| 225 | TRPA1#34(AS): 5' UCAAGAAUGACCUUCAUGGUC 3' |
| 226 | TRPA1#35(S): 5' GAAGGUCAUUCUUGAU 3' |
| 227 | TRPA1#35(AS): 5' AUCAAGAAUGACCUUCAUGGU 3' |
| 228 | TRPA1#36(S): 5' AAGGUCAUUCUUGAUA 3' |
| 229 | TRPA1#36(AS): 5' UAUCAAGAAUGACCUUCAUGG 3' |
| 230 | TRPA1#37(S): 5' AGGUCAUUCUUGAUAC 3' |
| 231 | TRPA1#37(AS): 5' GUAUCAAGAAUGACCUUCAUG 3' |
| 232 | TRPA1#38(S): 5' GGUCAUUCUUGAUACU 3' |
| 233 | TRPA1#38(AS): 5' AGUAUCAAGAAUGACCUUCAU 3' |
| 234 | TRPA1#39(S): 5' GUCAUUCUUGAUACUA 3' |
| 235 | TRPA1#39(AS): 5' UAGUAUCAAGAAUGACCUUCA 3' |
| 236 | TRPA1#40(S): 5' UCAUUCUUGAUACUAA 3' |
| 237 | TRPA1#40(AS): 5' UUAGUAUCAAGAAUGACCUUC 3' |
| 238 | TRPA1#41(S): 5' CAGAAGACAAGUCCUG 3' |
| 239 | TRPA1#41(AS): 5' CAGGACUUGUCUUCUGUGGAA 3' |
| 240 | TRPA1#42(S): 5' UUUCCAACAGAAAAGG 3' |
| 241 | TRPA1#42(AS): 5' CCUUUUCUGUUGGAAAUUUG 3' |
| 242 | TRPA1#43(S): 5' GGCAAUGUGGAGCAAU 3' |
| 243 | TRPA1#43(AS): 5' AUUGCUCCACAUUGCCACUGC 3' |
| 244 | TRPA1#44(S): 5' GCAGGUGGAACUUCAU 3' |
| 245 | TRPA1#44(AS): 5' AUGAAGUUCCACCUGCAUAGC 3' |
| 246 | TRPA1#45(S): 5' CAGGUGGAACUUCAUA 3' |
| 247 | TRPA1#45(AS): 5' UAUGAAGUUCCACCUGCAUAG 3' |
| 248 | TRPA1#46(S): 5' AGGUGGAACUUCAUAC 3' |
| 249 | TRPA1#46(AS): 5' GUAUGAAGUUCCACCUGCAUA 3' |
| 250 | TRPA1#47(S): 5' GGUGGAACUUCAUACC 3' |
| 251 | TRPA1#47(AS): 5' GGUAUGAAGUUCCACCUGCAU 3' |
| 252 | TRPA1#48(S): 5' GUGGAACUUCAUACCA 3' |
| 253 | TRPA1#48(AS): 5' UGGUAUGAAGUUCCACCUGCA 3' |
| 254 | TRPA1#49(S): 5' UGAUUAUGGAAAUACC 3' |
| 255 | TRPA1#49(AS): 5' GGUAUUUCCAUAAUCAUCCAU 3' |
| 256 | TRPA1#50(S): 5' AAUACCCCUCUGCAUU 3' |
| 257 | TRPA1#50(AS): 5' AAUGCAGAGGGGUAUUUCCAU 3' |

TABLE 4-continued

Nucleic acid sequences for exemplary TRPA1-targeting asiRNA.

| SEQ ID NO: | SEQUENCE |
|---|---|
| 258 | TRPA1#51(S): 5' UACCCCUCUGCAUUGU 3' |
| 259 | TRPA1#51(AS): 5' ACAAUGCAGAGGGGUAUUUCC 3' |
| 260 | TRPA1#52(S): 5' ACCCCUCUGCAUUGUG 3' |
| 261 | TRPA1#52(AS): 5' CACAAUGCAGAGGGGUAUUUC 3' |
| 262 | TRPA1#53(S): 5' UUGUGCUGUAGAAAAA 3' |
| 263 | TRPA1#53(AS): 5' UUUUUCUACAGCACAAUGCAG 3' |
| 264 | TRPA1#54(S): 5' ACGCUCUCCACUUAUA 3' |
| 265 | TRPA1#54(AS): 5' UAUAAGUGGAGAGCGUCCUUC 3' |
| 266 | TRPA1#55(S): 5' CCACUUAUAUUAGCAA 3' |
| 267 | TRPA1#55(AS): 5' UUGCUAAUAUAAGUGGAGAGC 3' |
| 268 | TRPA1#56(S): 5' GUGCCCAAGUAGACAU 3' |
| 269 | TRPA1#56(AS): 5' AUGUCUACUUGGGCACCUUUA 3' |
| 270 | TRPA1#57(S): 5' UGCCCAAGUAGACAUA 3' |
| 271 | TRPA1#57(AS): 5' UAUGUCUACUUGGGCACCUUU 3' |
| 272 | TRPA1#58(S): 5' GCCCAAGUAGACAUAA 3' |
| 273 | TRPA1#58(AS): 5' UUAUGUCUACUUGGGCACCUU 3' |
| 274 | TRPA1#59(S): 5' CCCAAGUAGACAUAAA 3' |
| 275 | TRPA1#59(AS): 5' UUUAUGUCUACUUGGGCACCU 3' |
| 276 | TRPA1#60(S): 5' CAAGUAGACAUAAAAG 3' |
| 277 | TRPA1#60(AS): 5' CUUUUAUGUCUACUUGGGCAC 3' |
| 278 | TRPA1#61(S): 5' AAGUAGACAUAAAAGA 3' |
| 279 | TRPA1#61(AS): 5' UCUUUUAUGUCUACUUGGGCA 3' |
| 280 | TRPA1#62(S): 5' AGUAGACAUAAAAGAU 3' |
| 281 | TRPA1#62(AS): 5' AUCUUUUAUGUCUACUUGGGC 3' |
| 282 | TRPA1#63(S): 5' AUUUAUGCAGAUGCAA 3' |
| 283 | TRPA1#63(AS): 5' UUGCAUCUGCAUAAAUUCAGG 3' |
| 284 | TRPA1#64(S): 5' UAUGGGCGUAUCAAUA 3' |
| 285 | TRPA1#64(AS): 5' UAUUGAUACGCCCAUAACUGG 3' |
| 286 | TRPA1#65(S): 5' AUGGGCGUAUCAAUAC 3' |
| 287 | TRPA1#65(AS): 5' GUAUUGAUACGCCCAUAACUG 3' |
| 288 | TRPA1#66(S): 5' CGAGGCUUCUGAAUGA 3' |
| 289 | TRPA1#66(AS): 5' UCAUUCAGAAGCCUCGUAUCA 3' |
| 290 | TRPA1#67(S): 5' GAGGCUUCUGAAUGAA 3' |
| 291 | TRPA1#67(AS): 5' UUCAUUCAGAAGCCUCGUAUC 3' |
| 292 | TRPA1#68(S): 5' AGGCUUCUGAAUGAAG 3' |
| 293 | TRPA1#68(AS): 5' CUUCAUUCAGAAGCCUCGUAU 3' |
| 294 | TRPA1#69(S): 5' UCUCAGUGACCACAAU 3' |
| 295 | TRPA1#69(AS): 5' AUUGUGGUCACUGAGAAACAA 3' |
| 296 | TRPA1#70(S): 5' CUCAGUGACCACAAUG 3' |
| 297 | TRPA1#70(AS): 5' CAUUGUGGUCACUGAGAAACA 3' |
| 298 | TRPA1#71(S): 5' ACACUCAGACCAUGAA 3' |
| 299 | TRPA1#71(AS): 5' UUCAUGGUCUGAGUGUACCCG 3' |
| 300 | TRPA1#72(S): 5' ACUGUCUUGGUCUCAU 3' |
| 301 | TRPA1#72(AS): 5' AUGAGACCAAGACAGUAAGAU 3' |
| 302 | TRPA1#73(S): 5' CUGUCUUGGUCUCAUA 3' |
| 303 | TRPA1#73(AS): 5' UAUGAGACCAAGACAGUAAGA 3' |
| 304 | TRPA1#74(S): 5' UGUCUUGGUCUCAUAC 3' |
| 305 | TRPA1#74(AS): 5' GUAUGAGACCAAGACAGUAAG 3' |
| 306 | TRPA1#75(S): 5' AUAUUUGGGUAUUGCA 3' |
| 307 | TRPA1#75(AS): 5' UGCAAUACCCAAAUAUACUUG 3' |
| 308 | TRPA1#76(S): 5' GGGUAUUGCAAAGAAG 3' |
| 309 | TRPA1#76(AS): 5' CUUCUUUGCAAUACCCAAAUA 3' |
| 310 | TRPA1#77(S): 5' UUUUCCAACAGAAAAG 3' |
| 311 | TRPA1#77(AS): 5' CUUUUCUGUUGGAAAAUUUGC 3' |
| 312 | TRPA1#78(S): 5' GCAAUGUGGAGCAAUU 3' |
| 313 | TRPA1#78(AS): 5' AAUUGCUCCACAUUGCCACUG 3' |
| 314 | TRPA1#79(S): 5' UUUUGGACUCAGCUUU 3' |
| 315 | TRPA1#79(AS): 5' AAAGCUGAGUCCAAAAGCCAG 3' |
| 316 | TRPA1#80(S): 5' UUUGGACUCAGCUUUU 3' |
| 317 | TRPA1#80(AS): 5' AAAAGCUGAGUCCAAAAGCCA 3' |
| 318 | TRPA1#81(S): 5' UUGGACUCAGCUUUUA 3' |
| 319 | TRPA1#81(AS): 5' UAAAAGCUGAGUCCAAAAGCC 3' |
| 320 | TRPA1#82(S): 5' CUAGGAGAUAUCAAUU 3' |
| 321 | TRPA1#82(AS): 5' AAUUGAUAUCUCCUAGCAUCA 3' |
| 322 | TRPA1#83(S): 5' UAGGAGAUAUCAAUUA 3' |
| 323 | TRPA1#83(AS): 5' UAAUUGAUAUCUCCUAGCAUC 3' |
| 324 | TRPA1#84(S): 5' GGAGAUAUCAAUUAUC 3' |
| 325 | TRPA1#84(AS): 5' GAUAAUUGAUAUCUCCUAGCA 3' |
| 326 | TRPA1#85(S): 5' GAGAUAUCAAUUAUCG 3' |
| 327 | TRPA1#85(AS): 5' CGAUAAUUGAUAUCUCCUAGC 3' |
| 328 | TRPA1#86(S): 5' AGAUAUCAAUUAUCGA 3' |
| 329 | TRPA1#86(AS): 5' UCGAUAAUUGAUAUCUCCUAG 3' |
| 330 | TRPA1#87(S): 5' AUAUUUGUCCCAAUUG 3' |

TABLE 4-continued

Nucleic acid sequences for exemplary TRPA1-targeting asiRNA.

| SEQ ID NO: | SEQUENCE |
|---|---|
| 331 | TRPA1#87(AS): 5' CAAUUGGGACAAAUAUUGUGA 3' |
| 332 | TRPA1#88(S):  5' UAUUUGUCCCAAUUGU 3' |
| 333 | TRPA1#88(AS): 5' ACAAUUGGGACAAAUAUUGUG 3' |
| 334 | TRPA1#89(S):  5' CCAAUUGUCCUCAUGA 3' |
| 335 | TRPA1#89(AS): 5' UCAUGAGGACAAUUGGGACAA 3' |
| 336 | TRPA1#90(S):  5' CAAUUGUCCUCAUGAA 3' |
| 337 | TRPA1#90(AS): 5' UUCAUGAGGACAAUUGGGACA 3' |
| 338 | TRPA1#91(S):  5' UGCUGAGGUCCAGAAA 3' |
| 339 | TRPA1#91(AS): 5' UUUCUGGACCUCAGCAAUGUC 3' |
| 340 | TRPA1#92(S):  5' AGAGGAUAGCUAUGCA 3' |
| 341 | TRPA1#92(AS): 5' UGCAUAGCUAUCCUCUUCAAU 3' |
| 342 | TRPA1#93(S):  5' GAGGAUAGCUAUGCAG 3' |
| 343 | TRPA1#93(AS): 5' CUGCAUAGCUAUCCUCUUCAA 3' |
| 344 | TRPA1#94(S):  5' UAUGCAGGUGGAACUU 3' |
| 345 | TRPA1#94(AS): 5' AAGUUCCACCUGCAUAGCUAU 3' |
| 346 | TRPA1#95(S):  5' AUGCAGGUGGAACUUC 3' |
| 347 | TRPA1#95(AS): 5' GAAGUUCCACCUGCAUAGCUA 3' |
| 348 | TRPA1#96(S):  5' UGCAGGUGGAACUUCA 3' |
| 349 | TRPA1#96(AS): 5' UGAAGUUCCACCUGCAUAGCU 3' |
| 350 | TRPA1#97(S):  5' AACAGCAUGAGCUCAU 3' |
| 351 | TRPA1#97(AS): 5' AUGAGCUCAUGCUGUUUUUCC 3' |
| 352 | TRPA1#98(S):  5' CAGAAGAUGGAGAUCA 3' |
| 353 | TRPA1#98(AS): 5' UGAUCUCCAUCUUCUGAAUGA 3' |
| 354 | TRPA1#99(S):  5' AGAAGAUGGAGAUCAU 3' |
| 355 | TRPA1#99(AS): 5' AUGAUCUCCAUCUUCUGAAUG 3' |
| 356 | TRPA1#100(S):  5' GAAGAUGGAGAUCAUC 3' |
| 357 | TRPA1#100(AS): 5' GAUGAUCUCCAUCUUCUGAAU 3' |
| 358 | TRPA1#101(S):  5' AAGAUGGAGAUCAUCU 3' |
| 359 | TRPA1#101(AS): 5' AGAUGAUCUCCAUCUUCUGAA 3' |
| 360 | TRPA1#102(S):  5' GAUGGAGAUCAUCUCU 3' |
| 361 | TRPA1#102(AS): 5' AGAGAUGAUCUCCAUCUUCUG 3' |

The asiRNAs listed in Table 4 were incubated at 95° C. for 5 minutes and at 37° C. for 1 hour in annealing buffer (Bioneer Inc. Korea). Proper strand annealing was confirmed via gel electrophoresis using a UV transilluminator. For the screen, 5×10³ A549 cells (ATCC) that had been cultured in Dulbecco's modified Eagle's medium (DMEM, Gibco) containing 10% fetal bovine serum (FBS, Gibco) and 100 units/ml Penicillin and 100 µg/ml Streptomycin in a 100 mm cell culture dish were seed 96 well plates. The A549 cells were transfected with 0.1 nM of the asiRNAs using RNAiMAX (Invitrogen Inc.) according to the manufacturer's instructions.

The TRPA1 mRNA levels in the transfected cells were measured 24 hours after transfection using qRT-PCR. Specifically, total RNA was extracted and synthesized the cDNA using SuperPrep Cell Lysis & RT kit for qPCR (TOYOBO) according to manufacturer's instructions. qRT-PCR was performed using THUNDERBIRD® Probe qPCR Mix (TOYOBO) according to manufacturer's instructions. Amplification of the TRPA1 was detected using TRPA1 TaqMan® Probe (Hs00175798_m1). 18S was amplified as an internal control using 18S TaqMan® Probe (Hs03928985_g1).

The level of TRPA1 inhibition by each of the 102 asiRNAs is provided in FIG. 9. 14 of the asiRNA sequences, asiRNA (#32), asiRNA (#34), asiRNA (#35), asiRNA (#38), asiRNA (#40), asiRNA (#41), asiRNA (#50), asiRNA (#64), asiRNA (#66), asiRNA (#69), asiRNA (#71), asiRNA (#72), asiRNA (#78) and asiRNA (#81), were selected for use in follow-up studies.

Example 7: Inhibition of TRPA1 mRNA and Protein Expression Using TRPA1-Targeting asiRNAs The asiRNAs selected in Example 6, asiRNA (#32), asiRNA (#34), asiRNA (#35), asiRNA (#38), asiRNA (#40), asiRNA (#41), asiRNA (#50), asiRNA (#64), asiRNA (#66), asiRNA (#69), asiRNA (#71), asiRNA (#72), asiRNA (#78) and asiRNA (#81), were tested for their ability to inhibit TRPA1 mRNA and protein expression.

The asiRNAs were incubated at 95° C. for 5 minutes and at 37° C. for 1 hour in annealing buffer (Bioneer Inc. Korea). Proper strand annealing was confirmed via gel electrophoresis using a UV transilluminator. For the screen, A549 cells (ATCC) that had been cultured in Dulbecco's modified Eagle's medium (Gibco) containing 10% fetal bovine serum (Gibco) and 100 units/ml Penicillin and 100 µg/ml Streptomycin in a 100 mm cell culture dish. One day prior to transfection, 2.5×10⁴ A549 cells were seeded in 24-well plates. The A549 cells were transfected with 1 nM of the asiRNAs using RNAiMAX (Invitrogen Inc.) according to the manufacturer's instructions.

24 hours after asiRNA transfection, total RNA was extracted using RNAiPlus® (TaKaRa) and then 500 ng of the extracted RNA was used for cDNA synthesis using the High-capacity cDNA reverse transcription kit (Applied Biosystems), according to the manufacturer's instructions. Amplification of the TRPA1 was detected using TRPA1 TaqMan® Probe (Hs00175798_m1). 18S was amplified as an internal control using 18S TaqMan® Probe (Hs03928985_g1).

48 hours after asiRNA transfection, TRPA1 protein levels were determined via western blot. Briefly, the transfected A549 cells were lysed with 1% SDS lysis buffer (1% SDS, 100 mM Tris pH 8.0). 30 µg of the total protein extract of A549 cells were loaded onto an 8% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and 1% BSA (Bioworld) and then incubated overnight at 4° C. in 5% skim milk and 1% BSA containing anti-TRPA1 antibody (Novus) and anti-β-actin antibody (Santa Cruz). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL substrate (Thermo scientific) for 1 minute. The TRPA1 and β-actin bands were then imaged using a Chemidoc instrument (Bio-rad).

Figure 10:
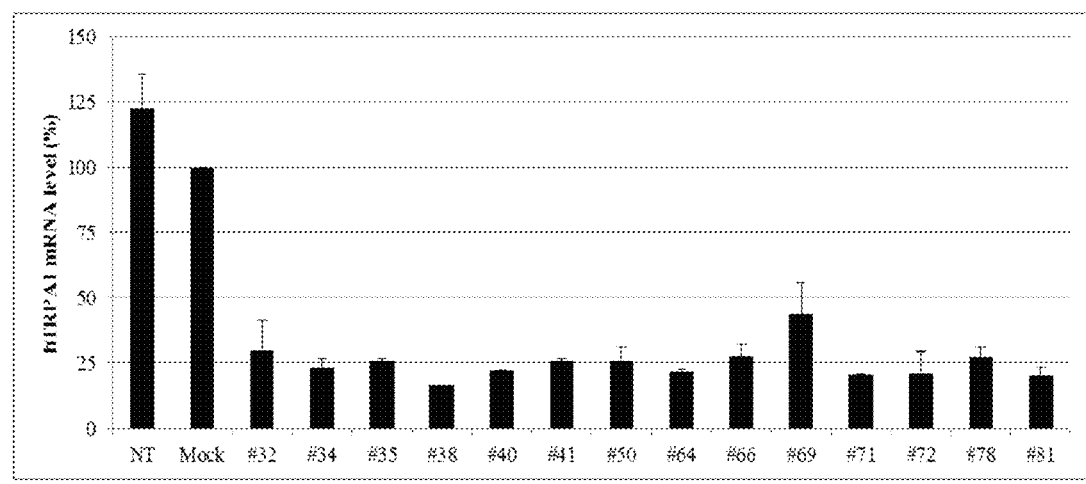
FIG. 10 shows the gene silencing effects of 14 exemplary asiRNAs that target TRPA1.
Figure 11:
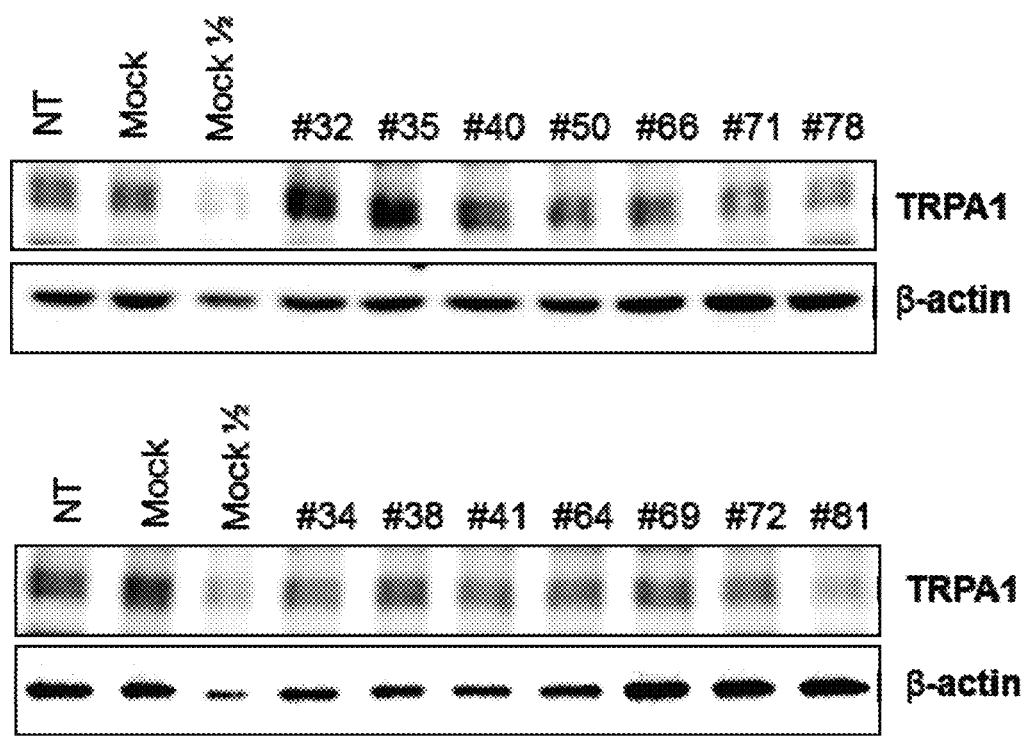
FIG. 11 shows the inhibition of TRPA1 protein expression by 14 exemplary asiRNAs that target TRPA1.

The level of TRPA1 inhibition of 14 asiRNAs is provided in FIG. 10. The results of western blot are depicted in FIG. 11. asiRNA (#71) and asiRNA (#81) were selected for use in follow-up studies.

Example 8: Chemical Modification of asiRNAs for Self-Delivery

Chemical modifications were applied to the asiRNAs and the cellular delivery of the modified asiRNAs was tested in the absence of other delivery reagents. As described below, certain of the modifications improved endocytosis and stability of asiRNAs. Such cell penetrating asiRNAs (cp-asiRNAs) are able to be delivered into the cell in the absence of a delivery reagent.

Potential cp-asiRNA (Table 5) screened for TRPA1 mRNA and protein inhibition in A549 cells. Each potential cp-asiRNA was incubated with A549 cells at 1 μM and 3 μM without a delivery reagent and TRPA1 expression levels were measured by qRT-PCR and western blot.

the potential cp-asiRNAs in OPTI-MEM buffer for 24 hours, at each point the cp-asiRNA containing OPTI-MEM media was replaced with a serum containing media.

Total RNA was extracted 48 hours after asiRNA transfection, using RNAiPlus® (TaKaRa) and then 500 ng of the extracted RNA was used for cDNA synthesis using the High-capacity cDNA reverse transcription kit (Applied Biosystems), according to the manufacturer's instructions. Amplification of the TRPA1 was detected using TRPA1 TaqMan® Probe (Hs00175798_m1). 18S was amplified as an internal control using 18S TaqMan® Probe (Hs03928985_g1).

TRPA1 protein levels were determined via western blot 72 hours after asiRNA transfection. Briefly, the transfected A549 cells were lysed with 1% SDS lysis buffer (1% SDS, 100 mM Tris pH8.0). 30 μg of the total protein extract of A549 cells were loaded onto an 8% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and 1% BSA (Bioworld) and then incubated overnight at 4° C. in 5% skim milk and 1% BSA containing anti-TRPA1 antibody (Novus) and

TABLE 5

Modified asiRNA sequences tested for self-delivery and TRPA1 inhibition.
(m = 2'-O-Methyl RNA. * = phosphorothioate bond.)

| Name | SEQ ID NO: | SEQUENCE |
|---|---|---|
| TRPA1 cp-asiRNA #71 PS4 (s) | 362 | 5' mACmACmUCmAGmACmCAmU*G*mA*A*Cholesterol 3' |
| TRPA1 cp-asiRNA #71 21(2,4)(AS) | 363 | 5' UUCAUGGUCUGAGUmGmUA*C*C*C*G 3' |
| TRPA1 cp-asiRNA #71 21(4,4)(AS) | 364 | 5' UUCAUGGUCUGAGUmGmUmA*mC*C*C*G 3' |
| TRPA1 cp-asiRNA #71 21(7,4)(AS) | 365 | 5' UUCAUGGUCUGAGUmGmUmA*mC*mC*mC*mG 3' |
| TRPA1 cp-asiRNA #81 PS4(s) | 366 | 5' mUUmGGmACmUCmAGmCUmU*U*mU*A*Cholesterol 3' |
| TRPA1 cp-asiRNA #81 21(2,4)(AS) | 367 | 5' UAAAAGCUGAGUCCmAmAA*A*G*C*C 3' |
| TRPA1 cp-asiRNA #81 21(4,4)(AS) | 368 | 5' UAAAAGCUGAGUCCmAmAmA*mA*G*C*C 3' |
| TRPA1 cp-asiRNA #81 21(7,4)(AS) | 369 | 5' UAAAAGCUGAGUCCmAmAmA*mA*mG*mC*mC 3' |

A549 cells (ATCC) that had been cultured in Dulbecco's modified Eagle's medium (DMEM, Gibco) containing 10% fetal bovine serum (FBS, Gibco), 100 units/ml Penicillin and 100 μg/ml Streptomycin in a 100 mm cell culture dish.

The potential cp-asiRNAs listed in Table 2 were incubated at 95° C. for 5 minutes and at 37° C. for 1 hour in Opti-MEM (Gibco). Proper strand annealing of the potential cp-asiRNAs was confirmed by gel electrophoresis using a UV transilluminator.

One day prior to treatment, 2.5×10⁴ A549 cells were seeded in 24-well plates. Immediately before treatment, the A549 cells were washed with Dulbecco's modified Eagle's medium (DMEM, Gibco) then cultured in the presence of anti-β-actin antibody (Santa Cruz). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL substrate (Thermo scientific) for 1 minute. The TRPA1 and β-actin bands were then imaged using a Chemidoc instrument (Bio-rad).

Figure 12:
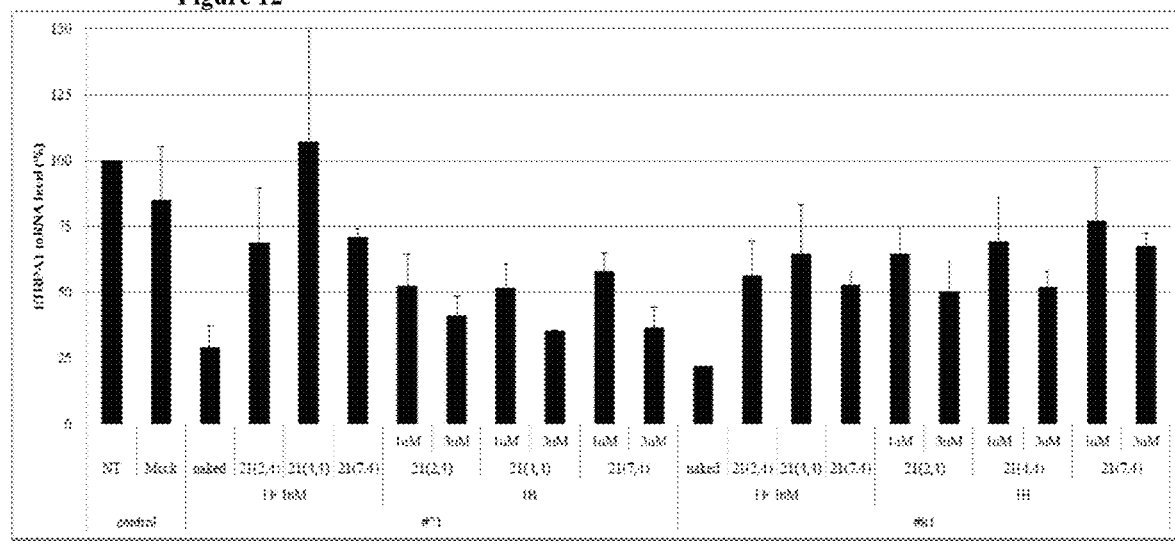
FIG. 12 shows the gene silencing efficiency of exemplary TRPA1-targeting cell-penetrating asiRNAs (TRPA1 cp-asiRNAs) to which various chemical modifications have been applied.
Figure 13:
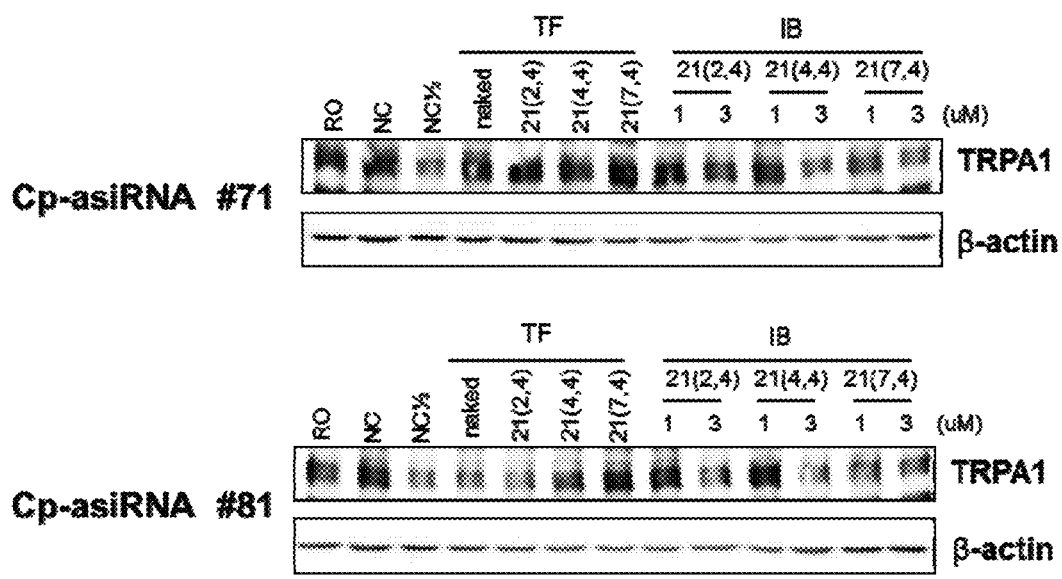
FIG. 13 shows the inhibition of TRPA1 protein expression by exemplary cp-asiRNAs.

The level of TRPA1 inhibition of 6 potential cp-asiRNAs is provided in FIG. 12 and FIG. 13. cp-asiRNA #71_21(4, 4) and cp-asiRNA #81_21(4, 4) was selected for further studies.

Example 9: Additional Chemical Modification of cp-asiRNA Structures

A variety of potential TRPA1 cp-asiRNA structures having different strand length and number of phosphorothioate bond and 2'-O-methylation modifications were synthesized and tested for its ability to inhibit TRPA1 expression (Table 6).

TABLE 6

Additional cp-asiRNA sequence.
(m = 2'-O-Methyl RNA. * = phosphorothioate bond.)

| Name | SEQ ID NO: | SEQUENCE |
|---|---|---|
| TRPA1 cp-asiRNA #71_PS3 (s) | 370 | 5' mACmACmUCmAGmACmCAmUG*mA*A*Cholesterol 3' |
| TRPA1 cp-asiRNA #71_PS4 (s) | 371 | 5' mACmACmUCmAGmACmCAmU*G*mA*A*Cholesterol 3' |
| TRPA1 cp-asiRNA #71_19(4,4)(AS) | 372 | 5' UUCAUGGUCUGAGUmG*mU*mA*mC*C 3' |
| TRPA1 cp-asiRNA #71_21(4,4)(AS) | 373 | 5' UUCAUGGUCUGAGUmGmUmA*mC*C*C*G 3' |
| TRPA1 cp-asiRNA #81_PS3 (s) | 374 | 5' mUUmGGmACmUCmAGmCUmUU*mU*A*Cholesterol 3' |
| TRPA1 cp-asiRNA #81_PS4 (s) | 375 | 5' mUUmGGmACmUCmAGmCUmU*U*mU*A*Cholesterol 3' |
| TRPA1 cp-asiRNA #81_19(4,4)(AS) | 376 | 5' UAAAAGCUGAGUCCmA*mA*mA*mA*G 3' |
| TRPA1 cp-asiRNA #81_21(4,4)(AS) | 377 | 5' UAAAAGCUGAGUCCmAmAmA*mA*G*C*C 3' |

The ability of 1 μM or 3 μM of each of the potential cp-asiRNAs listed in Table 6 to inhibit TRPA1 mRNA and protein expression in A549 cells was tested.

A549 cells (ATCC) that had been cultured in Dulbecco's modified Eagle's medium (DMEM, Gibco) containing 10% fetal bovine serum (FBS, Gibco), 100 units/ml Penicillin and 100 μg/ml Streptomycin. The potential cp-asiRNAs listed in Table 3 were incubated at 95° C. for 5 minutes and at 37° C. for 1 hour in Opti-MEM (Gibco). Proper strand annealing was confirmed by gel electrophoresis using a UV transilluminator.

One day prior to treatment, $2.5 \times 10^4$ A549 cells were seeded in 24-well plates. Immediately before treatment, the A549 cells were washed with DMEM (Gibco) then cultured in the presence of the potential cp-asiRNAs in Opti-MEM media for 24 hours, at which point the cp-asiRNA-containing Opti-MEM media was replaced with a serum-containing media.

Total RNA was extracted 48 hours after asiRNA transfection using RNAiPlus® (TaKaRa) and then 500 ng of the extracted RNA was used for cDNA synthesis using the High-capacity cDNA reverse transcription kit (Applied Biosystems), according to the manufacturer's instructions. Amplification of the TRPA1 was detected using TRPA1 TaqMan® Probe (Hs00175798_m1). 18S was amplified as an internal control using 18S TaqMan® Probe (Hs03928985_g1).

TRPA1 protein levels were determined via western blot 72 hours after asiRNA transfection. Briefly, the transfected A549 cells were lysed with 1% SDS lysis buffer (1% SDS, 100 mM Tris pH 8.0). 30 μg of the total protein extract of A549 cells were loaded onto an 8% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and 1% BSA (Bioworld) and then incubated overnight at 4° C. in 5% skim milk and 1% BSA containing anti-TRPA1 antibody (Novus) and anti-β-actin antibody (Santa Cruz). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL substrate (Thermo scientific) for 1 minute. The TRPA1 and β-actin bands were then imaged using a Chemi-doc instrument (Bio-rad).

Figure 14:
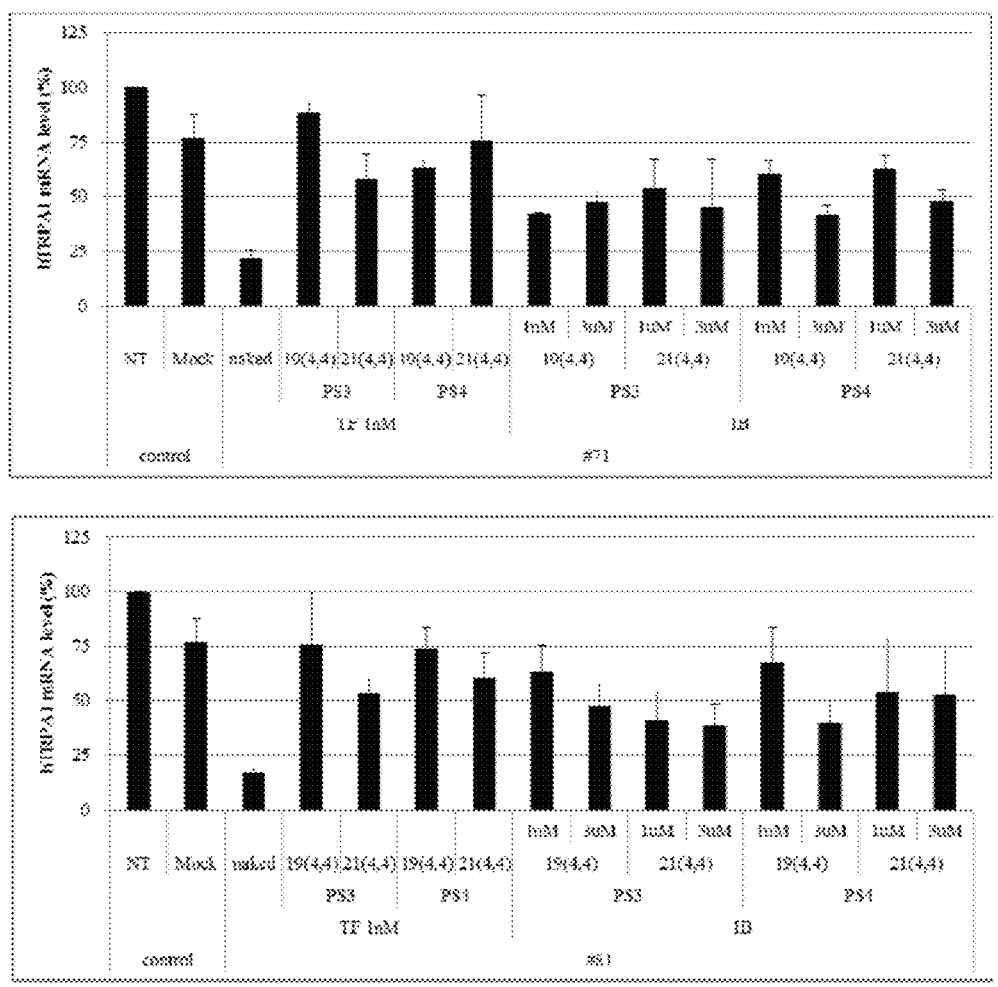
FIG. 14 shows the gene silencing efficiency of 8 cp-asiRNAs of different antisense strand lengths (19 or 21 nucleotides) and different sense strand chemical modifications (3 or 4 phosphorothioate bond).

As shown the FIG. 14 and FIG. 15, the indicated TRPA1 cp-asiRNA exhibited the similar mRNA levels of TRPA1 inhibition.

Example 10: Inhibition of TRPA1 Protein Expression Using TRPA1-Specific cp-asiRNAs The efficacy of cp-asiRNAs for the inhibition of TRPA1 protein level was tested.

Each potential cp-asiRNA was incubated with A549 cells at 1 µM and 3 µM without a delivery reagent and TRPA1 protein levels were measured by western blot.

A549 cells (ATCC) that had been cultured in Dulbecco's modified Eagle's medium (DMEM, Gibco) containing 10% fetal bovine serum (FBS, Gibco) and 100 units/ml Penicillin and 100 µg/ml Streptomycin. The potential cp-asiRNAs were incubated at 95° C. for 5 minutes and at 37° C. for 1 hour in Opti-MEM (Gibco). Proper strand annealing was confirmed by gel electrophoresis using a UV transilluminator.

One day prior to treatment, $2.5 \times 10^4$ A549 cells were seeded in 24-well plates. Immediately before treatment, the A549 cells were washed with DMEM (Gibco) then cultured in the presence of the potential cp-asiRNAs in Opti-MEM media for 24 hours, at which point the cp-asiRNA-containing Opti-MEM media was replaced with a serum-containing media.

TRPA1 protein levels were determined via western blot 72 hours after asiRNA transfection. Briefly, the transfected A549 cells were lysed with 1% SDS lysis buffer (1% SDS, 100 mM Tris pH 8.0). 30 µg of the total protein extract of A549 cells were loaded onto an 8% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and 1% BSA (Bioworld) and then incubated overnight at 4° C. in 5% skim milk and 1% BSA containing anti-TRPA1 antibody (Novus) and anti-GAPDH antibody (Santa Cruz). The membrane was then washed with 1×TBST for 10 minutes three times and was incubated for 1 hour at the room temperature in 5% skim milk with HRP-conjugated secondary antibody. The membrane was washed with 1× TBST for 10 minutes and treated with 1×ECL substrate (Thermo scientific) for 1 minute. The TRPA1 and GAPDH bands were then imaged using a Chemidoc instrument (Bio-rad).

Figure 16:
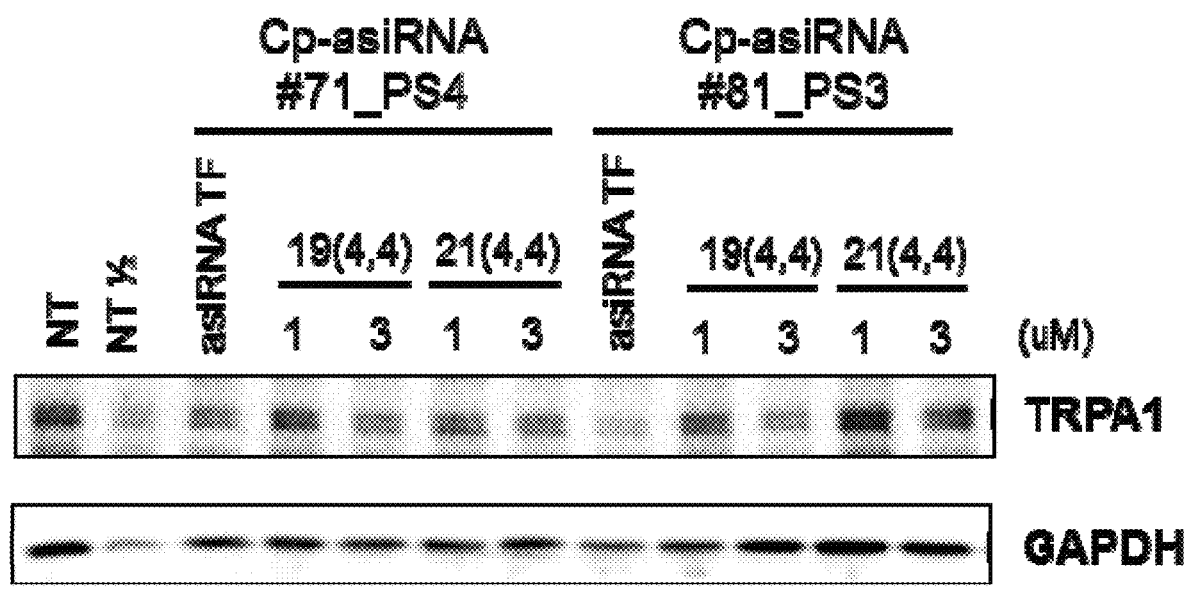
FIG. 16 shows the inhibition of TRPA1 protein expression by 4 exemplary cp-asiRNAs. A549 cells were incubated with 1 μM and 3 μM cp-asiRNAs in the absence of transfection reagent.

The results of the western blot assay are depicted in FIG. 16. As a result, TRPA1 cp-asiRNA #81 containing 3 phosphorothioate bond on sense strand and 19 nucleotides antisense strand with 4 phosphorothioate bond and four 2'-O-Methylation (TRPA1 cp-asiRNA #81 PS3/19(4,4)) exhibited the highest levels of TRPA1 inhibition.

Example 11: Screening for F2RL1-Targeting Asymmetric Shorter-Duplex Small Interfering RNAs To identify asymmetric shorter-duplex small interfering RNAs (asiRNAs) that inhibit F2RL1 with high efficiency, 100 asiRNAs were synthesized and screened. The nucleic acid sequences of the screened asiRNAs are provided in Table 7.

TABLE 7

Nucleic acid sequences for exemplary F2RL1-targeting asiRNA.

| SEQ ID NO: | SEQUENCE |
| --- | --- |
| 378 | F2RL1#1(S): 5'CCUCUCUGUCAUCUGG 3' |
| 379 | F2RL1#1(AS): 5'CCAGAUGACAGAGAGGAGGUC 3' |
| 380 | F2RL1#2(S): 5'CUCUCUGUCAUCUGGU 3' |
| 381 | F2RL1#2(AS): 5'ACCAGAUGACAGAGAGGAGGU 3' |
| 382 | F2RL1#3(S): 5'UCUCUGUCAUCUGGUU 3' |
| 383 | F2RL1#3(AS): 5'AACCAGAUGACAGAGAGGAGG 3' |
| 384 | F2RL1#4(S): 5'CUCUGUCAUCUGGUUC 3' |
| 385 | F2RL1#4(AS): 5'GAACCAGAUGACAGAGAGGAG 3' |
| 386 | F2RL1#5(S): 5'UCUGUCAUCUGGUUCC 3' |
| 387 | F2RL1#5(AS): 5'GGAACCAGAUGACAGAGAGGA 3' |
| 388 | F2RL1#6(S): 5'CUGUCAUCUGGUUCCC 3' |
| 389 | F2RL1#6(AS): 5'GGGAACCAGAUGACAGAGAGG 3' |
| 390 | F2RL1#7(S): 5'UGUCAUCUGGUUCCCC 3' |
| 391 | F2RL1#7(AS): 5'GGGGAACCAGAUGACAGAGAG 3' |
| 392 | F2RL1#8(S): 5'CACCAUCCCUUUGUAU 3' |
| 393 | F2RL1#8(AS): 5'AUACAAAGGGAUGGUGACCAG 3' |
| 394 | F2RL1#9(S): 5'ACCAUCCCUUUGUAUG 3' |
| 395 | F2RL1#9(AS): 5'CAUACAAAGGGAUGGUGACCA 3' |
| 396 | F2RL1#10(S): 5'CCAUCCCUUUGUAUGU 3' |
| 397 | F2RL1#10(AS): 5'ACAUACAAAGGGAUGGUGACC 3' |
| 398 | F2RL1#11(S): 5'CAUCCCUUUGUAUGUC 3' |
| 399 | F2RL1#11(AS): 5'GACAUACAAAGGGAUGGUGAC 3' |
| 400 | F2RL1#12(S): 5'ACAAAGGGAUGGUGAC 3' |
| 401 | F2RL1#12(AS): 5'GUCACCAUCCCUUUGUAUGUC 3' |
| 402 | F2RL1#13(S): 5'UUCAUUACUUCCUCU 3' |
| 403 | F2RL1#13(AS): 5'AGAGGAAGUAAUUGAACAUGU 3' |
| 404 | F2RL1#14(S): 5'UCAAUUACUUCCUCUC 3' |
| 405 | F2RL1#14(AS): 5'GAGAGGAAGUAAUUGAACAUG 3' |
| 406 | F2RL1#15(S): 5'CUUUGUCUAUUACUUU 3' |
| 407 | F2RL1#15(AS): 5'AAAGUAAUAGACAAAGGGGUC 3' |
| 408 | F2RL1#16(S): 5'UUUGUCUAUUACUUUG 3' |
| 409 | F2RL1#16(AS): 5'CAAAGUAAUAGACAAAGGGGU 3' |
| 410 | F2RL1#17(S): 5'UUGUCUAUUACUUUGU 3' |
| 411 | F2RL1#17(AS): 5'ACAAAGUAAUAGACAAAGGGG 3' |
| 412 | F2RL1#18(S): 5'AUGGCCAAUCUGGCCU 3' |
| 413 | F2RL1#18(AS): 5'AGGCCAGAUUGGCCAUGUAAA 3' |
| 414 | F2RL1#19(S): 5'UUGGCUGACCUCCUCU 3' |
| 415 | F2RL1#19(AS): 5'AGAGGAGGUCAGCCAAGGCCA 3' |
| 416 | F2RL1#20(S): 5'GGCUGACCUCCUCUCU 3' |

TABLE 7-continued

Nucleic acid sequences for exemplary F2RL1-targeting asiRNA.

| SEQ ID NO: | SEQUENCE |
|---|---|
| 417 | F2RL1#20(AS): 5'AGAGAGGAGGUCAGCCAAGGC 3' |
| 418 | F2RL1#21(S): 5'GCUGACCUCCUCUCUG 3' |
| 419 | F2RL1#21(AS): 5'CAGAGAGGAGGUCAGCCAAGG 3' |
| 420 | F2RL1#22(S): 5'CUGACCUCCUCUCUGU 3' |
| 421 | F2RL1#22(AS): 5'ACAGAGAGGAGGUCAGCCAAG 3' |
| 422 | F2RL1#23(S): 5'UGACCUCCUCUCUGUC 3' |
| 423 | F2RL1#23(AS): 5'GACAGAGAGGAGGUCAGCCAA 3' |
| 424 | F2RL1#24(S): 5'GACCUCCUCUCUGUCA 3' |
| 425 | F2RL1#24(AS): 5'UGACAGAGAGGAGGUCAGCCA 3' |
| 426 | F2RL1#25(S): 5'ACCUCCUCUCUGUCAU 3' |
| 427 | F2RL1#25(AS): 5'AUGACAGAGAGGAGGUCAGCC 3' |
| 428 | F2RL1#26(S): 5'CCUCCUCUCUGUCAUC 3' |
| 429 | F2RL1#26(AS): 5'GAUGACAGAGAGGAGGUCAGC 3' |
| 430 | F2RL1#27(S): 5'CUCCUCUCUGUCAUCU 3' |
| 431 | F2RL1#27(AS): 5'AGAUGACAGAGAGGAGGUCAG 3' |
| 432 | F2RL1#28(S): 5'UCCUCUCUGUCAUCUG 3' |
| 433 | F2RL1#28(AS): 5'CAGAUGACAGAGAGGAGGUCA 3' |
| 434 | F2RL1#29(S): 5'GUCAUCUGGUUCCCCU 3' |
| 435 | F2RL1#29(AS): 5'AGGGGAACCAGAUGACAGAGA 3' |
| 436 | F2RL1#30(S): 5'ACAUGGCAACAACUGG 3' |
| 437 | F2RL1#30(AS): 5'CCAGUUGUUGCCAUGUAUGUG 3' |
| 438 | F2RL1#31(S): 5'UAUUGGCUUUUUCUAU 3' |
| 439 | F2RL1#31(AS): 5'AUAGAAAAAGCCAAUAAGCAC 3' |
| 440 | F2RL1#32(S): 5'AUUGGCUUUUUCUAUG 3' |
| 441 | F2RL1#32(AS): 5'CAUAGAAAAAGCCAAUAAGCA 3' |
| 442 | F2RL1#33(S): 5'UUGGCUUUUUCUAUGG 3' |
| 443 | F2RL1#33(AS): 5'CCAUAGAAAAAGCCAAUAAGC 3' |
| 444 | F2RL1#34(S): 5'UUCUAUGGCAACAUGU 3' |
| 445 | F2RL1#34(AS): 5'ACAUGUUGCCAUAGAAAAAGC 3' |
| 446 | F2RL1#35(S): 5'UCUAUGGCAACAUGUA 3' |
| 447 | F2RL1#35(AS): 5'UACAUGUUGCCAUAGAAAAAG 3' |
| 448 | F2RL1#36(S): 5'CUCUUCAUGACCUGCC 3' |
| 449 | F2RL1#36(AS): 5'GGCAGGUCAUGAAGAGAAUGG 3' |
| 450 | F2RL1#37(S): 5'UCUUCAUGACCUGCCU 3' |
| 451 | F2RL1#37(AS): 5'AGGCAGGUCAUGAAGAGAAUG 3' |
| 452 | F2RL1#38(S): 5'CUUCAUGACCUGCCUC 3' |
| 453 | F2RL1#38(AS): 5'GAGGCAGGUCAUGAAGAGAAU 3' |
| 454 | F2RL1#39(S): 5'UUCAUGACCUGCCUCA 3' |
| 455 | F2RL1#39(AS): 5'UGAGGCAGGUCAUGAAGAGAA 3' |
| 456 | F2RL1#40(S): 5'UCAUGACCUGCCUCAG 3' |
| 457 | F2RL1#40(AS): 5'CUGAGGCAGGUCAUGAAGAGA 3' |
| 458 | F2RL1#41(S): 5'CAUGACCUGCCUCAGU 3' |
| 459 | F2RL1#41(AS): 5'ACUGAGGCAGGUCAUGAAGAG 3' |
| 460 | F2RL1#42(S): 5'UGCCUCAGUGUGCAGA 3' |
| 461 | F2RL1#42(AS): 5'UCUGCACACUGAGGCAGGUCA 3' |
| 462 | F2RL1#43(S): 5'GCCUCAGUGUGCAGAG 3' |
| 463 | F2RL1#43(AS): 5'CUCUGCACACUGAGGCAGGUC 3' |
| 464 | F2RL1#44(S): 5'CUCAGUGUGCAGAGGU 3' |
| 465 | F2RL1#44(AS): 5'ACCUCUGCACACUGAGGCAGG 3' |
| 466 | F2RL1#45(S): 5'UCAGUGUGCAGAGGUA 3' |
| 467 | F2RL1#45(AS): 5'UACCUCUGCACACUGAGGCAG 3' |
| 468 | F2RL1#46(S): 5'CAUCGUGAACCCCAUG 3' |
| 469 | F2RL1#46(AS): 5'CAUGGGGUUCACGAUGACCCA 3' |
| 470 | F2RL1#47(S): 5'AUCGUGAACCCCAUGG 3' |
| 471 | F2RL1#47(AS): 5'CCAUGGGGUUCACGAUGACCC 3' |
| 472 | F2RL1#48(S): 5'UCGUGAACCCCAUGGG 3' |
| 473 | F2RL1#48(AS): 5'CCCAUGGGGUUCACGAUGACC 3' |
| 474 | F2RL1#49(S): 5'CAGGAAGAAGGCAAAC 3' |
| 475 | F2RL1#49(AS): 5'GUUUGCCUUCUUCCUGGAGUG 3' |
| 476 | F2RL1#50(S): 5'AGGAAGAAGGCAAACA 3' |
| 477 | F2RL1#50(AS): 5'UGUUUGCCUUCUUCCUGGAGU 3' |
| 478 | F2RL1#51(S): 5'GGAAGAAGGCAAACAU 3' |
| 479 | F2RL1#51(AS): 5'AUGUUUGCCUUCUUCCUGGAG 3' |
| 480 | F2RL1#52(S): 5'GUCACCAUCCCUUUGU 3' |
| 481 | F2RL1#52(AS): 5'ACAAAGGGAUGGUGACCAGCA 3' |
| 482 | F2RL1#53(S): 5'UCACCAUCCCUUUGUA 3' |
| 483 | F2RL1#53(AS): 5'UACAAAGGGAUGGUGACCAGC 3' |
| 484 | F2RL1#54(S): 5'AUCCCUUUGUAUGUCG 3' |
| 485 | F2RL1#54(AS): 5'CGACAUACAAAGGGAUGGUGA 3' |
| 486 | F2RL1#55(S): 5'UGUAUGUCGUGAAGCA 3' |
| 487 | F2RL1#55(AS): 5'UGCUUCACGACAUACAAAGGG 3' |
| 488 | F2RL1#56(S): 5'GUAUGUCGUGAAGCAG 3' |
| 489 | F2RL1#56(AS): 5'CUGCUUCACGACAUACAAAGG 3' |

TABLE 7-continued

Nucleic acid sequences for exemplary F2RL1-targeting asiRNA.

| SEQ ID NO: | SEQUENCE |
|---|---|
| 490 | F2RL1#57(S): 5'UAUGUCGUGAAGCAGA 3' |
| 491 | F2RL1#57(AS): 5'UCUGCUUCACGACAUACAAAG 3' |
| 492 | F2RL1#58(S): 5'GUCGUGAAGCAGACCA 3' |
| 493 | F2RL1#58(AS): 5'UGGUCUGCUUCACGACAUACA 3' |
| 494 | F2RL1#59(S): 5'UCGUGAAGCAGACCAU 3' |
| 495 | F2RL1#59(AS): 5'AUGGUCUGCUUCACGACAUAC 3' |
| 496 | F2RL1#60(S): 5'CGUGAAGCAGACCAUC 3' |
| 497 | F2RL1#60(AS): 5'GAUGGUCUGCUUCACGACAUA 3' |
| 498 | F2RL1#61(S): 5'GUGAAGCAGACCAUCU 3' |
| 499 | F2RL1#61(AS): 5'AGAUGGUCUGCUUCACGACAU 3' |
| 500 | F2RL1#62(S): 5'GGGAGACAUGUUCAAU 3' |
| 501 | F2RL1#62(AS): 5'AUUGAACAUGUCUCCCACCAA 3' |
| 502 | F2RL1#63(S): 5'GGAGACAUGUUCAAUU 3' |
| 503 | F2RL1#63(AS): 5'AAUUGAACAUGUCUCCCACCA 3' |
| 504 | F2RL1#64(S): 5'GAGACAUGUUCAAUUA 3' |
| 505 | F2RL1#64(AS): 5'UAAUUGAACAUGUCUCCCACC 3' |
| 506 | F2RL1#65(S): 5'AGACAUGUUCAAUUAC 3' |
| 507 | F2RL1#65(AS): 5'GUAAUUGAACAUGUCUCCCAC 3' |
| 508 | F2RL1#66(S): 5'GACAUGUUCAAUUACU 3' |
| 509 | F2RL1#66(AS): 5'AGUAAUUGAACAUGUCUCCCA 3' |
| 510 | F2RL1#67(S): 5'ACAUGUUCAAUUACUU 3' |
| 511 | F2RL1#67(AS): 5'AAGUAAUUGAACAUGUCUCCC 3' |
| 512 | F2RL1#68(S): 5'CAUGUUCAAUUACUUC 3' |
| 513 | F2RL1#68(AS): 5'GAAGUAAUUGAACAUGUCUCC 3' |
| 514 | F2RL1#69(S): 5'AUGUUCAAUUACUUCC 3' |
| 515 | F2RL1#69(AS): 5'GGAAGUAAUUGAACAUGUCUC 3' |
| 516 | F2RL1#70(S): 5'UGUUCAAUUACUUCCU 3' |
| 517 | F2RL1#70(AS): 5'AGGAAGUAAUUGAACAUGUCU 3' |
| 518 | F2RL1#71(S): 5'CAAUUACUUCCUCUCU 3' |
| 519 | F2RL1#71(AS): 5'AGAGAGGAAGUAAUUGAACAU 3' |
| 520 | F2RL1#72(S): 5'UUCCUCUCUCUGGCCA 3' |
| 521 | F2RL1#72(AS): 5'UGGCCAGAGAGAGGAAGUAAU 3' |
| 522 | F2RL1#73(S): 5'CCUCUCUCUGGCCAUU 3' |
| 523 | F2RL1#73(AS): 5'AAUGGCCAGAGAGAGGAAGUA 3' |
| 524 | F2RL1#74(S): 5'CUCUCUCUGGCCAUUG 3' |
| 525 | F2RL1#74(AS): 5'CAAUGGCCAGAGAGAGGAAGU 3' |
| 526 | F2RL1#75(S): 5'UCUCUCUGGCCAUUGG 3' |
| 527 | F2RL1#75(AS): 5'CCAAUGGCCAGAGAGAGGAAG 3' |
| 528 | F2RL1#76(S): 5'UGAAAACUCAGAGAAG 3' |
| 529 | F2RL1#76(AS): 5'CUUCUCUGAGUUUUCAUCCAU 3' |
| 530 | F2RL1#77(S): 5'GAAAACUCAGAGAAGA 3' |
| 531 | F2RL1#77(AS): 5'UCUUCUCUGAGUUUUCAUCCA 3' |
| 532 | F2RL1#78(S): 5'AAAACUCAGAGAAGAA 3' |
| 533 | F2RL1#78(AS): 5'UUCUUCUCUGAGUUUUCAUCC 3' |
| 534 | F2RL1#79(S): 5'AAACUCAGAGAAGAAA 3' |
| 535 | F2RL1#79(AS): 5'UUUCUUCUCUGAGUUUUCAUC 3' |
| 536 | F2RL1#80(S): 5'ACUCAGAGAAGAAAG 3' |
| 537 | F2RL1#80(AS): 5'CUUUUCUUCUCUGAGUUUUCA 3' |
| 538 | F2RL1#81(S): 5'CUCAGAGAAGAAAGG 3' |
| 539 | F2RL1#81(AS): 5'CCUUUUCUUCUCUGAGUUUUC 3' |
| 540 | F2RL1#82(S): 5'CUGCAUCGACCCCUUU 3' |
| 541 | F2RL1#82(AS): 5'AAAGGGGUCGAUGCAGCUGUU 3' |
| 542 | F2RL1#83(S): 5'UGCAUCGACCCCUUUG 3' |
| 543 | F2RL1#83(AS): 5'CAAAGGGGUCGAUGCAGCUGU 3' |
| 544 | F2RL1#84(S): 5'GCAUCGACCCCUUUGU 3' |
| 545 | F2RL1#84(AS): 5'ACAAAGGGGUCGAUGCAGCUG 3' |
| 546 | F2RL1#85(S): 5'CAUCGACCCCUUUGUC 3' |
| 547 | F2RL1#85(AS): 5'GACAAAGGGGUCGAUGCAGCU 3' |
| 548 | F2RL1#86(S): 5'AUCGACCCCUUUGUCU 3' |
| 549 | F2RL1#86(AS): 5'AGACAAAGGGGUCGAUGCAGC 3' |
| 550 | F2RL1#87(S): 5'UCGACCCCUUUGUCUA 3' |
| 551 | F2RL1#87(AS): 5'UAGACAAAGGGGUCGAUGCAG 3' |
| 552 | F2RL1#88(S): 5'CGACCCCUUUGUCUAU 3' |
| 553 | F2RL1#88(AS): 5'AUAGACAAAGGGGUCGAUGCA 3' |
| 554 | F2RL1#89(S): 5'GACCCCUUUGUCUAUU 3' |
| 555 | F2RL1#89(AS): 5'AAUAGACAAAGGGGUCGAUGC 3' |
| 556 | F2RL1#90(S): 5'ACCCCUUUGUCUAUUA 3' |
| 557 | F2RL1#90(AS): 5'UAAUAGACAAAGGGGUCGAUG 3' |
| 558 | F2RL1#91(S): 5'CCCCUUUGUCUAUUAC 3' |
| 559 | F2RL1#91(AS): 5'GUAAUAGACAAAGGGGUCGAU 3' |
| 560 | F2RL1#92(S): 5'CCCUUUGUCUAUUACU 3' |
| 561 | F2RL1#92(AS): 5'AGUAAUAGACAAAGGGGUCGA 3' |
| 562 | F2RL1#93(S): 5'CCUUUGUCUAUUACUU 3' |

TABLE 7-continued

Nucleic acid sequences for exemplary F2RL1-targeting asiRNA.

| SEQ ID NO: | SEQUENCE |
|---|---|
| 563 | F2RL1#93(AS): 5'AAGUAAUAGACAAAGGGGUCG 3' |
| 564 | F2RL1#94(S): 5'UGUCUAUUACUUUGUU 3' |
| 565 | F2RL1#94(AS): 5'AACAAAGUAAUAGACAAAGGG 3' |
| 566 | F2RL1#95(S): 5'UGCCGAAGUGUCCGCA 3' |
| 567 | F2RL1#95(AS): 5'UGCGGACACUUCGGCAAAGGA 3' |
| 568 | F2RL1#96(S): 5'GCCGAAGUGUCCGCAC 3' |
| 569 | F2RL1#96(AS): 5'GUGCGGACACUUCGGCAAAGG 3' |
| 570 | F2RL1#97(S): 5'CCGAAGUGUCCGCACU 3' |
| 571 | F2RL1#97(AS): 5'AGUGCGGACACUUCGGCAAAG 3' |
| 572 | F2RL1#98(S): 5'CGAAGUGUCCGCACUG 3' |
| 573 | F2RL1#98(AS): 5'CAGUGCGGACACUUCGGCAAA 3' |
| 574 | F2RL1#99(S): 5'GAAGUGUCCGCACUGU 3' |
| 575 | F2RL1#99(AS): 5'ACAGUGCGGACACUUCGGCAA 3' |
| 576 | F2RL1#100(S): 5'AAGUGUCCGCACUGUA 3' |
| 577 | F2RL1#100(AS): 5'UACAGUGCGGACACUUCGGCA 3' |

The asiRNAs listed in Table 7 were incubated at 95° C. for 5 minutes and at 37° C. for 1 hour in 1× siRNA duplex buffer (Bioneer). Proper strand annealing was confirmed via gel electrophoresis.

For the screen, A549 cells (ATCC) that had been cultured in Dulbecco's modified Eagle's medium (Gibco) containing 10% fetal bovine serum (Gibco), 100 µg/ml penicillin/streptomycin in a 100 mm cell culture dish. One day prior to transfection, 5×10³ A549 cells were seeded in 96-well plates. The A549 cells were transfected with 0.1 nM of the asiRNAs using RNAiMAX (Invitrogen) according to the manufacturer's instructions.

The F2RL1 mRNA levels in the transfected cells were measured 24 hours after transfection using real-time PCR. Specifically, total RNA was extracted and synthesized the cDNA using SuperPrep Cell Lysis & RT Kit for qPCR (TOYOBO), according to the manufacturer's instructions. Real-time PCR was performed using THUNDERBIRD® Probe qPCR Mix (TOYOBO) according to manufacturer's instructions. Amplification of the F2RL1 was detected using F2RL1 TaqMan® Probe (Hs00608346_m1). 18S was amplified as an internal control using 18S TaqMan® Probe (Hs03928985_g1).

Figure 18:
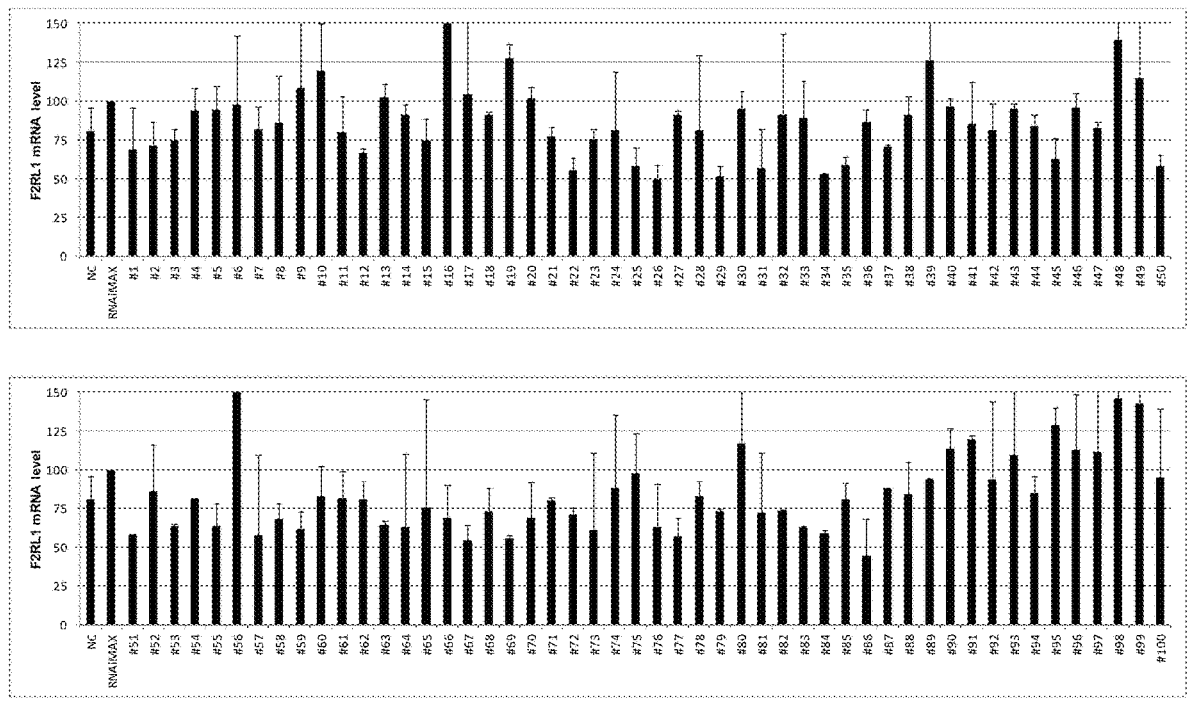
FIG. 18 shows the gene silencing efficiency of 100 exemplary asiRNAs that target F2RL1.

The level of F2RL1 inhibition by each of the 100 asiRNAs is provided in FIG. 18. 29 of the asiRNA sequences, asiF2RL1 #1, #22, #25, #26, #28, #29, #31, #34, #35, #45, #50, #51, #55, #57, #59, #64, #65, #67, #69, #73, #76, #77, #81, #84, #86, #87, #88, #92, and #100 were selected for use in follow-up studies.

Example 12: Inhibition of F2RL1 mRNA Expression Using F2RL1-Targeting asiRNAs

The 29 asiRNAs selected in Example 12, asiF2RL1 #1, #22, #25, #26, #28, #29, #31, #34, #35, #45, #50, #51, #55, #57, #59, #64, #65, #67, #69, #73, #76, #77, #81, #84, #86, #87, #88, #92, and #100, were tested for their ability to inhibit F2RL1 expression.

The asiRNAs were incubated at 95° C. for 5 minutes and at 37° C. for 1 hour in 1× siRNA duplex buffer (Bioneer). Proper strand annealing was confirmed via gel electrophoresis. For the screen, A549 cells (ATCC) that had been cultured in Dulbecco's modified Eagle's medium (Gibco) containing 10% fetal bovine serum (Gibco), 100 µg/ml penicillin/streptomycin in a 100 mm cell culture dish. One day prior to transfection, 2.5×10⁴ A549 cells were seeded in 24-well plates. The A549 cells were transfected with asiRNAs using RNAiMAX (Invitrogen) according to the manufacturer's instructions.

Specifically, total RNA was extracted using RNAiso Plus (TaKaRa), and then 500 ng of the extracted RNA was used for cDNA synthesis using the High-capacity cDNA reverse transcription kit (Applied Biosystems), according to the manufacturer's instructions. Amplification of the F2RL1 was detected using F2RL1 TaqMan® Probe (Hs00608346_m1). 18S was amplified as an internal control using 18S TaqMan® Probe (Hs03928985_g1).

Figure 19:
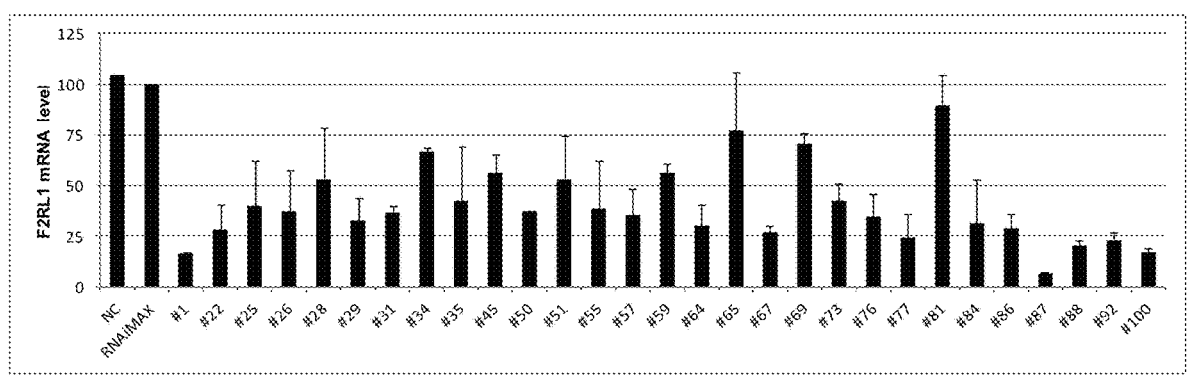
FIG. 19 shows the gene silencing efficiency of 29 exemplary asiRNAs that target F2RL1.

The level of F2RL1 inhibition of 29 asiRNAs is provided in FIG. 19. Twelve asiRNAs; asiF2RL1 #1, #22, #29, #50, #64, #67, #76, #77, #87, #88, #92, and #100 were selected for use in follow-up studies.

Example 13: Chemical Modification of asiRNAs

Chemical modifications were applied to 32 asiRNAs. As described below, certain of the modifications improved endocytosis and stability of the asiRNAs.

32 asiRNAs (Table 2) were tested for F2RL1 mRNA inhibition in A549 cells.

TABLE 8

Modified asiRNA sequences. m = 2'-O-Methyl RNA

| SEQ ID NO: | |
|---|---|
| 578 | F2RL1#29-1: (S) 5' mGUmCAmUCmUGmGUmUCmCCmCU 3' |
| 579 | F2RL1#29-1: (AS) 5' AGGGGAACCAGAUGACAGAGA 3' |
| 580 | F2RL1#29-2: (S) 5' mGUmCAmUCmUGmGUmUCmCCmCU 3' |
| 581 | F2RL1#29-2: (AS) 5' AGGGGAACCAGAUGmAmCAGAGA 3' |
| 582 | F2RL1#29-3: (S) 5' mGUmCAmUCmUGmGUmUCmCCmCU 3' |

TABLE 8-continued

Modified asiRNA sequences. m = 2'-O-Methyl RNA

| SEQ ID NO: | | |
|---|---|---|
| 583 | F2RL1#29-3: | (AS) 5' AGGGGAACCAGAUGmAmCmAmGAGA 3' |
| 584 | F2RL1#29-4: | (S) 5' mGUmCAmUCmUGmGUmUCmCCmCU 3' |
| 585 | F2RL1#29-4: | (AS) 5' AGGGGAACCAGAUGmAmCmAmGmAmGmA 3' |
| 586 | F2RL1#50-1: | (S) 5' mAGmGAmAGmAAmGGmCAmAAmCA 3' |
| 587 | F2RL1#50-1: (AS) 5' UGUUUGCCUUCUUCCUGGAGU 3' |
| 588 | F2RL1#50-2: | (S) 5' mAGmGAmAGmAAmGGmCAmAAmCA 3' |
| 589 | F2RL1#50-2: | (AS) 5' UGUUUGCCUUCUUCmCmUGGAGU 3' |
| 590 | F2RL1#50-3: | (S) 5' mAGmGAmAGmAAmGGmCAmAAmCA 3' |
| 591 | F2RL1#50-3: | (AS) 5' UGUUUGCCUUCUUCmCmUmGmGAGU 3' |
| 592 | F2RL1#50-4: | (S) 5' mAGmGAmAGmAAmGGmCAmAAmCA 3' |
| 593 | F2RL1#50-4: | (AS) 5' UGUUUGCCUUCUUCmCmUmGmAmGmU 3' |
| 594 | F2RL1#57-1: | (S) 5' mUAmUGmUCmGUmGAmAGmCAmGA 3' |
| 595 | F2RL1#57-1: | (AS) 5' UCUGCUUCACGACAUACAAAG 3' |
| 596 | F2RL1#57-2: | (S) 5' mUAmUGmUCmGUmGAmAGmCAmGA 3' |
| 597 | F2RL1#57-2: | (AS) 5' UCUGCUUCACGACAmUmACAAAG 3' |
| 598 | F2RL1#57-3: | (S) 5' mUAmUGmUCmGUmGAmAGmCAmGA 3' |
| 599 | F2RL1#57-3: | (AS) 5' UCUGCUUCACGACAmUmAmCmAAAG 3' |
| 600 | F2RL1#57-4: | (S) 5' mUAmUGmUCmGUmGAmAGmCAmGA 3' |
| 601 | F2RL1#57-4: | (AS) 5' UCUGCUUCACGACAmUmAmCmAmAmAmG 3' |
| 602 | F2RL1#64-1: | (S) 5' mGAmGAmCAmUGmUUmCAmAUmA 3' |
| 603 | F2RL1#64-1: | (AS) 5' UAAUUGAACAUGUCUCCCACC 3' |
| 604 | F2RL1#64-2: | (S) 5' mGAmGAmCAmUGmUUmCAmAUmA 3' |
| 605 | F2RL1#64-2: | (AS) 5' UAAUUGAACAUGUCmUmCCCACC 3' |
| 606 | F2RL1#64-3: | (S) 5' mGAmGAmCAmUGmUUmCAmAUmA 3' |
| 607 | F2RL1#64-3: | (AS) 5' UAAUUGAACAUGUCmUmCmCmCACC 3' |
| 608 | F2RL1#64-4: | (S) 5' mGAmGAmCAmUGmUUmCAmAUmA 3' |
| 609 | F2RL1#64-4: | (AS) 5' UAAUUGAACAUGUCmUmCmCmCmAmCmC 3' |
| 610 | F2RL1#67-1: | (S) 5' mACmAUmGUmUCmAAmUUmACmUU 3' |
| 611 | F2RL1#67-1: | (AS) 5' AAGUAAUUGAACAUGUCUCCC 3' |
| 612 | F2RL1#67-2: | (S)5' mACmAUmGUmUCmAAmUUmAmCmUU 3' |
| 613 | F2RL1#67-2: | (AS) 5' AAGUAAUUGAACAUmGmUCUCCC 3' |
| 614 | F2RL1#67-3: | (S) 5' mACmAUmGUmUCmAAmUUmACmUU 3' |
| 615 | F2RL1#67-3: | (AS) 5' AAGUAAUUGAACAUmGmUmCmUCCC 3' |
| 616 | F2RL1#67-4: | (S) 5' mACmAUmGUmUCmAAmUUmACmUU 3' |
| 617 | F2RL1#67-4: | (AS) 5' AAGUAAUUGAACAUmGmUmCmUmCmCmC 3' |
| 618 | F2RL1#76-1: | (S) 5' mUGmAAmAAmCUmCAmGAmGAmAG 3' |
| 619 | F2RL1#76-1: | (AS) 5' CUUCUCUGAGUUUUCAUCCAU 3' |

TABLE 8-continued

Modified asiRNA sequences. m = 2'-O-Methyl RNA

| SEQ ID NO: | | |
|---|---|---|
| 620 | F2RL1#76-2: (S) | 5' mUGmAAmAAmCUmCAmGAmGAmAG 3' |
| 621 | F2RL1#76-2: (AS) | 5' CUUCUCUGAGUUUUmCmAUCCAU 3' |
| 622 | F2RL1#76-3: (S) | 5' mUGmAAmAAmCUmCAmGAmGAmAG 3' |
| 623 | F2RL1#76-3: (AS) | 5' CUUCUCUGAGUUUUmCmAmUmCCAU 3' |
| 624 | F2RL1#76-4: (S) | 5' mUGmAAmAAmCUmCAmGAmGAmAG 3' |
| 625 | F2RL1#76-4: (AS) | 5' CUUCUCUGAGUUUUmCmAmUmCmCmAmU 3' |
| 626 | F2RL1#77-1: (S) | 5' mGAmAAmACmUCmAGmAGmAAmGA 3' |
| 627 | F2RL1#77-1: (AS) | 5' UCUUCUCUGAGUUUUCAUCCA 3' |
| 628 | F2RL1#77-2: (S) | 5' mGAmAAmACmUCmAGmAGmAAmGA 3' |
| 629 | F2RL1#77-2: (AS) | 5' UCUUCUCUGAGUUUmUmCAUCCA 3' |
| 630 | F2RL1#77-3: (S) | 5' mGAmAAmACmUCmAGmAGmAAmGA 3' |
| 631 | F2RL1#77-3: (AS) | 5' UCUUCUCUGAGUUUmUmCmAmUCCA 3' |
| 632 | F2RL1#77-4: (S) | 5' mGAmAAmACmUCmAGmAGmAAmGA 3' |
| 633 | F2RL1#77-4: (AS) | 5' UCUUCUCUGAGUUUmUmCmAmUmCmCmA 3' |
| 634 | F2RL1#100-1: (S) | 5' mAAmGUmGUmCCmGCmACmUGmUA 3' |
| 635 | F2RL1#100-1: (AS) | 5' UACAGUGCGGACACUUCGGCA 3' |
| 636 | F2RL1#100-2: (S) | 5' mAAmGUmGUmCCmGCmACmUGmUA 3' |
| 637 | F2RL1#100-2: (AS) | 5' UACAGUGCGGACACmUmUCGGCA 3' |
| 638 | F2RL1#100-3: (S) | 5' mAAmGUmGUmCCmGCmACmUGmUA 3' |
| 639 | F2RL1#100-3: (AS) | 5' UACAGUGCGGACACmUmUmCGGCA 3' |
| 640 | F2RL1#100-4: (S) | 5' mAAmGUmGUmCCmGCmACmUGmUA 3' |
| 641 | F2RL1#100-4: (AS) | 5' UACAGUGCGGACACmUmUmCmGmCmA 3' |

The asiRNAs listed in Table 8 were incubated at 95° C. for 5 minutes and at 37° C. for 1 hour in 1× siRNA duplex buffer (Bioneer). Proper strand annealing was confirmed via gel electrophoresis. For the screen, A549 cells (ATCC) that had been cultured in Dulbecco's modified Eagle's medium (Gibco) containing 10% fetal bovine serum (Gibco), 100 μg/ml penicillin/streptomycin in a 100 mm cell culture dish. One day prior to transfection, 2.5×10⁴ A549 cells were seeded in 24-well plates. The A549 cells were transfected with 0.3 nM of the asiRNAs using RNAiMAX (Invitrogen) according to the manufacturer's instructions.

The F2RL1 mRNA levels in the transfected cells were measured 24 hours after transfection using real-time PCR. Specifically, total RNA was extracted using RNAiso Plus (TaKaRa), and then 500 ng of the extracted RNA was used for cDNA synthesis using the High-capacity cDNA reverse transcription kit (Applied Biosystems), according to the manufacturer's instructions. The synthesized cDNA was diluted and then real-time PCR was performed using THUNDERBIRD® Probe qPCR Mix (TOYOBO) according to manufacturer's instructions. Amplification of the F2RL1 was detected using F2RL1 TaqMan® Probe (Hs00608346_m1). 18S was amplified as an internal control using 18S TaqMan® Probe (Hs03928985_g1).

Figure 20:
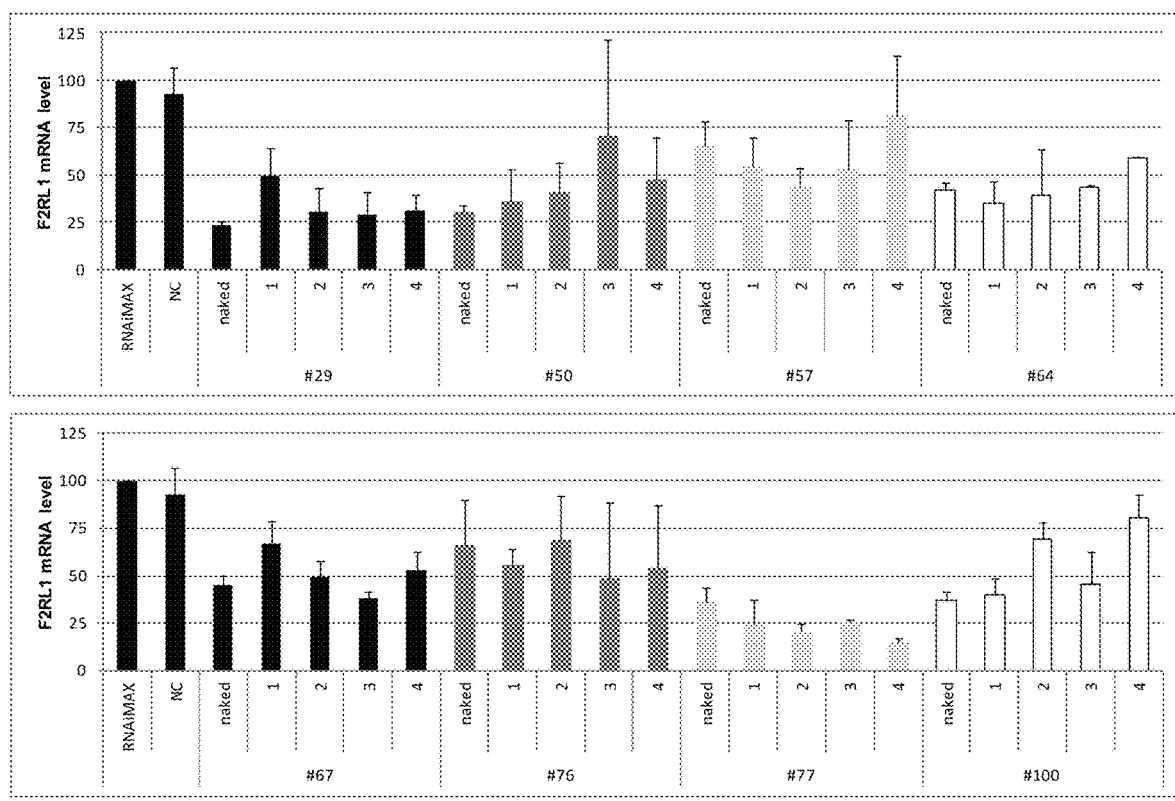
FIG. 20 shows the gene silencing efficiency of 32 exemplary asiRNAs containing 2'-O-Methylation modifications.

The level of F2RL1 inhibition of 32 asiRNAs is provided in FIG. 20.

Example 14: Inhibition of F2RL1 mRNA Expression Using F2RL1-Targeting asiRNAs

The 12 asiRNAs selected in Example 12, asiF2RL1 #1, #22, #29, #50, #64, #67, #76, #77, #87, #88, #92, and #100, were tested for their ability to inhibit F2RL1 expression.

The asiRNAs were incubated at 95° C. for 5 minutes and at 37° C. for 1 hour in 1× siRNA duplex buffer (Bioneer). Proper strand annealing was confirmed via gel electrophoresis. For the screen, A549 cells (ATCC) that had been cultured in Dulbecco's modified Eagle's medium (Gibco) containing 10% fetal bovine serum (Gibco), 100 μg/ml penicillin/streptomycin in a 100 mm cell culture dish. One day prior to transfection, 2.5×10⁴ A549 cells were seeded in 24-well plates. The A549 cells were transfected with 1 nM of the asiRNAs using RNAiMAX (Invitrogen) according to the manufacturer's instructions.

Specifically, total RNA was extracted using RNAiso Plus (TaKaRa), and then 500 ng of the extracted RNA was used for cDNA synthesis using the High-capacity cDNA reverse transcription kit (Applied Biosystems), according to the manufacturer's instructions. Amplification of the F2RL1 was detected using F2RL1 TaqMan® Probe (Hs00608346_m1). 18S was amplified as an internal control using 18S TaqMan® Probe (Hs03928985_g1).

Figure 21:
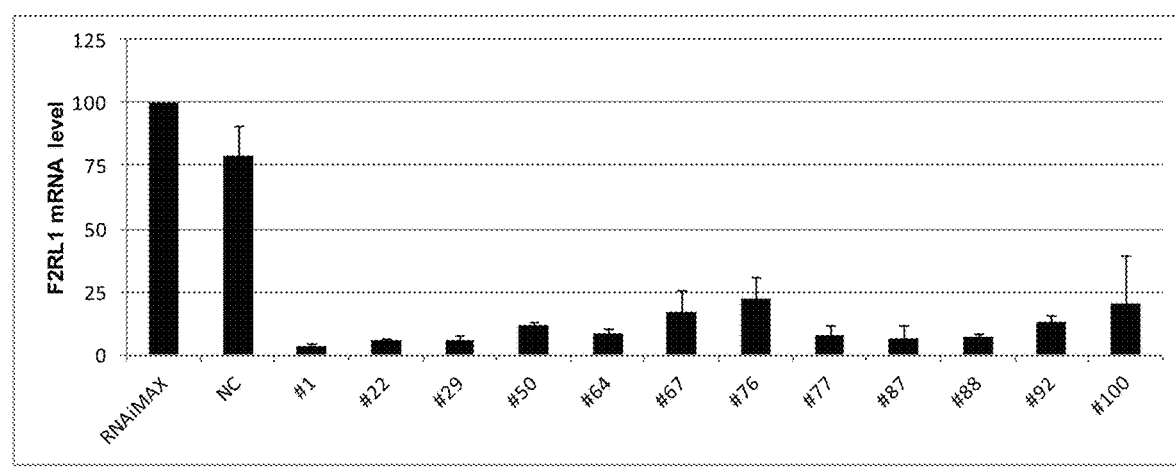
FIG. 21 shows the gene silencing effects of 12 exemplary asiRNAs that target F2RL1.

The level of F2RL1 inhibition of 12 asiRNAs is provided in FIG. 21.

Example 15: Inhibition of F2RL1 Protein Expression Using F2RL1-Targeting asiRNAs The efficacy of asiF2RL1 for the inhibition of F2RL1 protein was tested.

The asiRNAs were incubated at 95° C. for 5 minutes and at 37° C. for 1 hour in 1× siRNA duplex buffer (Bioneer). Proper strand annealing was confirmed via gel electrophoresis.

A549 cells (ATCC) that had been cultured in Dulbecco's modified Eagle's medium (Gibco) containing 10% fetal bovine serum (Gibco), 100 µg/ml penicillin/streptomycin in a 100 mm cell culture dish. One day prior to transfection, $2.5 \times 10^4$ A549 cells were seeded in 24-well plates. A549 cells were transfected with 1 nM of the asiRNAs using RNAiMAX (Invitrogen) according to the manufacturer's instructions.

The levels of F2RL1 protein expression were determined via western blot 72 hours after asiRNA transfection. Briefly, the transfected A549 cells were lysed with TX-100 lysis buffer (1% TX-100, 150 mM NaCl, 100 mM Tris (pH 8.8)). 10 µg of the total protein extracts of A549 cells were loaded onto a 10% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 3% BSA (Bioworld) and then incubated overnight at 4° C. in 3% BSA containing anti-F2RL1 antibody (Abcam) and anti-GAPDH antibody (Santa Cruz). The membrane was then washed with 1×TBST for 10 minutes three times and was incubated for 1 hour at the room temperature in 1×TBST with HRP-conjugated secondary antibody. The membrane was washed with 1×TBST for 10 minutes and treated with 1×ECL for 1 minute. The F2RL1 and GAPDH bands were then imaged using a Chemidoc instrument (Bio-rad).

The results of the western blot assay are depicted in FIG. 22. asiF2RL1 #22, #50, #77, and #92 were selected for the chemical modification.

Example 16: Chemical Modification of asiRNAs for Self-Delivery

Chemical modifications were applied to the 12 asiRNAs selected in Example 15 and the cellular delivery of the modified asiRNAs was tested in the absence of other delivery reagent. As described below, certain of the modifications improved endocytosis and stability of the asiRNAs. Such cell-penetrating asiRNAs (cp-asiRNAs) are able to be delivered into the cell in the absence of a delivery reagent.

12 potential cp-asiRNAs (Table 9) were screened for F2RL1 mRNA inhibition in A549 cells. Each potential cp-asiRNA was incubated with A549 cells at 1 µM and 3 µM without a delivery reagent and F2RL1 mRNA levels were measured by real-time PCR.

TABLE 9

Modified asiRNA sequences tested for self-delivery and F2RL1 inhibition.
m = 2'-O-Methyl RNA, * = phosphorothioate bond.

| SEQ ID NO: | | |
|---|---|---|
| 642 | F2RL1#22-PS4/21(2,4)(S): | 5' mCUmGAmCCmUCmCUmCUmC*U*mG*U*cholesterol 3' |
| 643 | F2RL1#22-PS4/21(2,4)(AS): | 5'ACAGAGAGGAGGUCmAmGC*C*A*A*G 3' |
| 644 | F2RL1#22-PS4/21(4,4)(S): | 5' mCUmGAmCCmUCmCUmCUmC*U*mG*U*cholesterol 3' |
| 645 | F2RL1#22-PS4/21(4,4)(AS): | 5' ACAGAGAGGAGGUCmAmGmC*mC*A*A*G 3' |
| 646 | F2RL1#22-PS4/21(7,4)(S): | 5' mCUmGAmCCmUCmCUmCUmC*U*mG*U*cholesterol 3' |
| 647 | F2RL1#22-PS4/21(7,4)(AS): | 5' ACAGAGAGGAGGUCmAmGmC*mC*mA*mA*mG 3' |
| 648 | F2RL1#50-PS4/21(2,4)(S): | 5' mAGmGAmAGmAAmGGmCAmA*A*mC*A*cholesterol 3' |
| 649 | F2RL1#50-PS4/21(2,4)(AS): | 5' UGUUUGCCUUCUUCmCmUG*G*A*G*U 3' |
| 650 | F2RL1#50-PS4/21(4,4)(S): | 5' mAGmGAmAGmAAmGGmCAmA*A*mC*A*cholesterol 3' |
| 651 | F2RL1#50-PS4/21(4,4)(AS): | 5' UGUUUGCCUUCUUCmCmUmG*mG*A*G*U 3' |
| 652 | F2RL1#50-PS4/21(7,4)(S): | 5' mAGmGAmAGmAAmGGmCAmA*A*mC*A*cholesterol 3' |
| 653 | F2RL1#50-PS4/21(7,4)(AS): | 5' UGUUUGCCUUCUUCmCmUmG*mG*mA*mG*mU 3' |
| 654 | F2RL1#77-PS4/21(2,4)(S): | 5' mGAmAAmACmUCmAGmAGmA*A*mG*A*cholesterol 3' |
| 655 | F2RL1#77-PS4/21(2,4)(AS): | 5' UCUUCUCUGAGUUUmUmCA*U*C*C*A 3' |
| 656 | F2RL1#77-PS4/21(4,4)(S): | 5' mGAmAAmACmUCmAGmAGmA*A*mG*A*cholesterol 3' |
| 657 | F2RL1#77-PS4/21(4,4)(AS): | 5' UCUUCUCUGAGUUUmUmCmA*mU*C*C*A 3' |

TABLE 9-continued

Modified asiRNA sequences tested for self-delivery and F2RL1 inhibition.
m = 2'-O-Methyl RNA, * = phosphorothioate bond.

| SEQ ID NO: | | |
|---|---|---|
| 658 | F2RL1#77-PS4/21(7,4)(S): | 5' mGAmAAmACmUCmAGmAGmA*A*mG*A*cholesterol 3' |
| 659 | F2RL1#77-PS4/21(7,4)(AS): | 5' UCUUCUCUGAGUUUmUmCmA*mU*mC*mC*mA 3' |
| 660 | F2RL1#92-PS4/21(2,4)(S): | 5' mCCmCUmUUmGUmCUmAUmU*A*mC*U*cholesterol 3' |
| 661 | F2RL1#92-PS4/21(2,4)(AS): | 5' AGUAAUAGACAAAGmGG*U*C*G*A 3' |
| 662 | F2RL1#92-PS4/21(4,4)(S): | 5' mCCmCUmUUmGUmCUmAUmU*A*mC*U*cholesterol 3' |
| 663 | F2RL1#92-PS4/21(4,4)(AS): | 5' AGUAAUAGACAAAGmGmGmG*mU*C*G*A 3' |
| 664 | F2RL1#92-PS4/21(7,4)(S): | 5' mCCmCUmUUmGUmCUmAUmU*A*mC*U*cholesterol 3' |
| 665 | F2RL1#92-PS4/21(7,4)(AS): | 5' AGUAAUAGACAAAGmGmGmG*mU*mC*mG*mA 3' |

A549 cells (ATCC) that had been cultured in Dulbecco's modified Eagle's medium (Gibco) containing 10% fetal bovine serum (Gibco), 100 μg/ml penicillin/streptomycin in a 100 mm cell culture dish.

The potential cp-asiRNAs listed in Table 9 were incubated at 95° C. for 5 minutes and at 37° C. for 1 hour in OPTI-MEM buffer (Gibco). Proper strand annealing was confirmed via gel electrophoresis.

One day prior to treatment, 2.5×10⁴ A549 cells were seeded in 24-well plates. Immediately before treatment, the A549 cells were washed with Dulbecco's modified Eagle's medium then cultured in the presence of the potential cp-asiRNAs in OPTI-MEM buffer for 8 and 24 hours, at each point the asiRNA-containing OPTI-MEM media was replaced with a serum-containing media.

Figure 23:
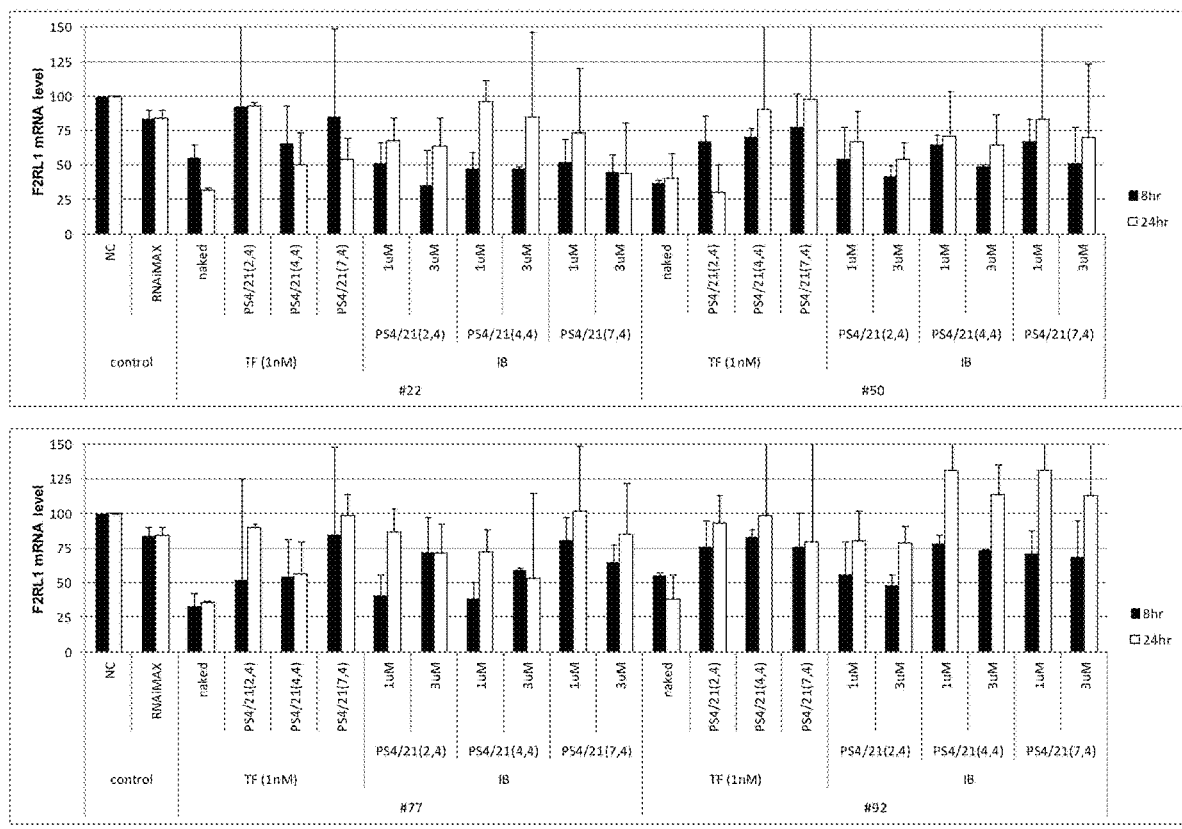
FIG. 23 shows the gene silencing efficiency of exemplary F2RL1-targeting cell-penetrating asiRNAs (cp-asiRNAs or cp-asiF2RL1s) to which various chemical modifications have been applied.

The level of F2RL1 mRNA expression was determined using real-time PCR 48 hours after asiRNAs treatment. The level of F2RL1 inhibition of cp-asiRNAs is provided in FIG. 23.

Example 17: Inhibition of F2RL1 mRNA Expression Using F2RL1-Targeting cp-asiRNAs The efficacies of cp-asiRNAs for the inhibition of F2RL1 RNA were tested.

Each potential cp-asiRNA was incubated with A549 cells at 1 μM and 3 μM without a delivery reagent and F2RL1 mRNA levels were measured using real-time PCR.

A549 cells (ATCC) that had been cultured in Dulbecco's modified Eagle's medium (Gibco) containing 10% fetal bovine serum (Gibco), 100 μg/ml penicillin/streptomycin in a 100 mm cell culture dish.

The cp-asiRNAs were incubated at 95° C. for 5 minutes and at 37° C. for 1 hour in OPTI-MEM buffer (Gibco). Proper strand annealing was confirmed via gel electrophoresis.

One day prior to treatment, 2.5×10⁴ A549 cells were seeded in 24-well plates. Immediately before treatment, the A549 cells were washed with Dulbecco's modified Eagle's medium (Gibco) then cultured in the presence of the potential cp-asiRNAs in OPTI-MEM buffer for 24 hours, at which point the asiRNA-containing OPTI-MEM media was replaced with a serum-containing media.

The level of F2RL1 mRNA expression was determined by real-time PCR 48 hours after asiRNA treatment. Total RNA was extracted using RNAiso Plus (TaKaRa), and then 500 ng of the extracted RNA was used for cDNA synthesis using the High-capacity cDNA reverse transcription kit (Applied Biosystems), according to the manufacturer's instructions. Amplification of the F2RL1 was detected using F2RL1 TaqMan® Probe (Hs00608346_m1). 18S was amplified as an internal control using 18S TaqMan® Probe (Hs03928985_g1).

The level of F2RL1 inhibition by cp-asiRNAs is provided in FIG. 24.

Example 18: Inhibition of F2RL1 Protein Using F2RL1-Targeting cp-asiRNAs

The efficacies of cp-asiRNAs for the inhibition of F2RL1 protein were tested.

Each potential cp-asiRNA was incubated with A549 cells at 1 μM and 3 μM without a delivery reagent and F2RL1 protein levels were detected by western blot.

A549 cells (ATCC) that had been cultured in Dulbecco's modified Eagle's medium (Gibco) containing 10% fetal bovine serum (Gibco), 100 μg/ml penicillin/streptomycin in a 100 mm cell culture dish.

The cp-asiRNAs were incubated at 95° C. for 5 minutes and at 37° C. for 1 hour in OPTI-MEM buffer (Gibco). Proper strand annealing was confirmed via gel electrophoresis.

One day prior to treatment, 2.5×10⁴ A549 cells were seeded in 24-well plates. Immediately before treatment, the A549 cells were washed with Dulbecco's modified Eagle's medium (Gibco) then cultured in the presence of the potential cp-asiRNAs in OPTI-MEM buffer for 24 hours, at which point the asiRNA-containing OPTI-MEM media was replaced with a serum-containing media.

The levels of F2RL1 protein expression were determined via western blot 72 hours after asiRNA transfection. Briefly, the treated A549 cells were lysed with TX-100 lysis buffer (1% TX-100, 150 mM NaCl, 100 mM Tris (pH 8.8)). 10 μg of the total protein extracts were loaded onto a 10% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 3% BSA (Bioworld) and then incubated overnight at 4° C. in 3% BSA containing anti-F2RL1 antibody (Abcam) and anti-GAPDH (Santa Cruz). The membrane was then washed with 1×TBST for 10 minutes three times and was incubated for 1 hour at the room temperature in 1×TBST with HRP-conjugated secondary antibody. The membrane was washed with 1×TBST for 10 minutes and treated with 1×ECL for 1 minute. The F2RL1 and GAPDH bands were then imaged using a Chemidoc instrument (Bio-rad).

Figure 25:
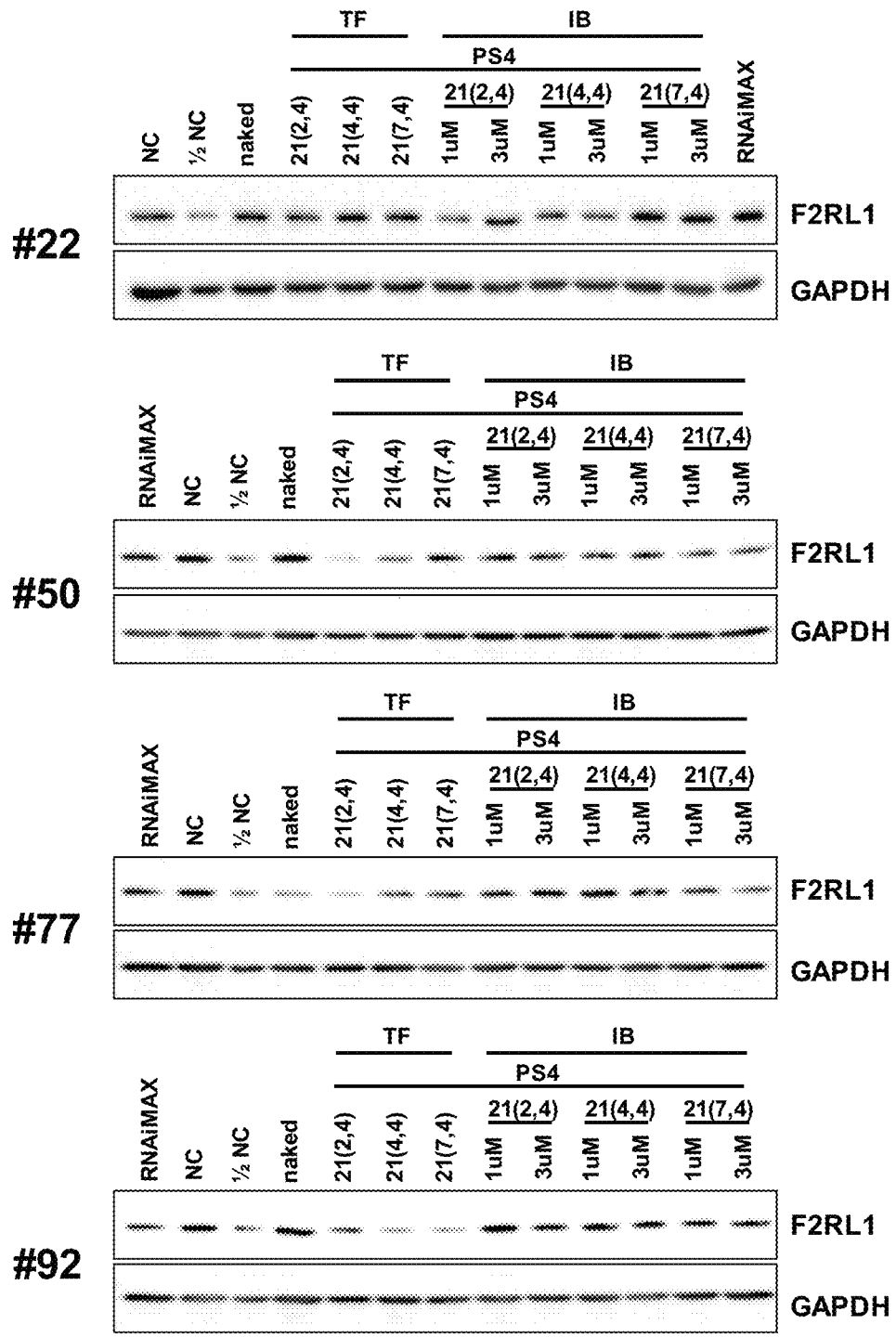
FIG. 25 shows the inhibition of F2RL1 protein expression by exemplary cp-asiRNAs.

The results of the western blot assay are depicted in FIG. 25.

Example 19: Inhibition of F2RL1 mRNA Expression Using Additional F2RL1-Targeting cp-asiRNAs A variety of potential cp-asiF2RL1 #22 and #50 structures having different strand lengths and number of 2'-O-methylation modifications and phosphorothioate bond were synthesized and tested for their ability to inhibit F2RL1 expression (Table 10).

Figure 26:
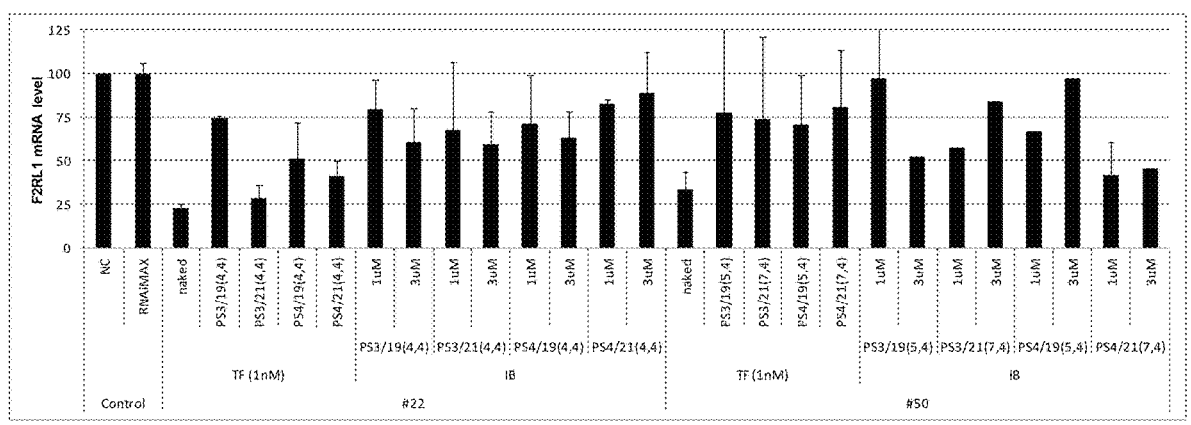
FIG. 26 shows the gene silencing efficiency of 8 cp-asiRNAs of different antisense strand lengths (19 or 21 nucleotides).

The level of F2RL1 inhibition by 8 cp-asiRNAs is provided in FIG. 26.

Example 20: Inhibition of F2RL1 Protein Expression Using Additional F2RL1-Targeting cp-asiRNAs The efficacy of cp-asiRNAs for the inhibition of F2RL1 protein was tested.

Each potential cp-asiRNA was incubated with A549 cells at 1 μM and 3 μM without a delivery reagent and F2RL1 protein levels were measured by western blot.

A549 cells (ATCC) that had been cultured in Dulbecco's modified Eagle's medium (Gibco) containing 10% fetal bovine serum (Gibco), 100 μg/ml penicillin/streptomycin in a 100 mm cell culture dish.

TABLE 10

Additional cp-asiRNA sequences. m = 2'-O-Methyl RNA, * = phosphorothioate bond.

| SEQ ID NO: | | |
|---|---|---|
| 666 | F2RL1#50-PS3/19(5,4)(S): | 5' mAGmGAmAGmAAmGGmCAmAA*mC*A*cholesterol 3' |
| 667 | F2RL1#50-PS3/19(5,4)(AS): | 5' UGUUUGCCUUCUUCmC*mU*mG*mG*mA 3' |
| 668 | F2RL1#50-PS3/21(7,4)(S): | 5' mAGmGAmAGmAAmGGmCAmAA*mC*A*cholesterol 3' |
| 669 | F2RL1#50-PS3/21(7,4)(AS): | 5' UGUUUGCCUUCUUCmCmUmG*mG*mA*mG*mU 3' |
| 670 | F2RL1#50-PS4/19(5,4)(S): | 5' mAGmGAmAGmAAmGGmCAmA*A*mC*A*cholesterol 3' |
| 671 | F2RL1#50-PS4/19(5,4)(AS): | 5' UGUUUGCCUUCUUCmC*mU*mG*mG*mA 3' |
| 672 | F2RL1#22-PS3/19(4,4)(S): | 5' mCUmGAmACCmUCmCUmCUmCU*mG*U*cholesterol 3' |
| 673 | F2RL1#22-PS4/19(4,4)(AS): | 5' ACAGAGAGGAGGUCmA*mG*mC*mC*A 3' |
| 674 | F2RL1#22-PS3/21(4,4)(S): | 5' mCUmGAmACCmUCmCUmCUmCU*mG*U*cholesterol 3' |
| 675 | F2RL1#22-PS4/21(4,4)(AS): | 5' ACAGAGAGGAGGUCmAmGmC*mC*A*A*G 3' |
| 676 | F2RL1#22-PS4/19(4,4)(S): | 5' mCUmGAmACCmUCmCUmCUmC*U*mG*U*cholesterol 3' |
| 677 | F2RL1#22-PS4/19(4,4)(AS): | 5' ACAGAGAGGAGGUCmA*mG*mC*mC*A 3' |

The ability of 1 μM and 3 μM of each of the potential cp-asiRNAs listed in Table 10 to inhibit F2RL1 mRNA in A549 cells was tested.

A549 cells (ATCC) that had been cultured in Dulbecco's modified Eagle's medium (Gibco) containing 10% fetal bovine serum (Gibco), 100 μg/ml penicillin/streptomycin in a 100 mm cell culture dish.

The potential cp-asiRNAs listed in Table 4 were incubated at 95° C. for 5 minutes and at 37° C. for 1 hour in OPTI-MEM buffer (Gibco). Proper strand annealing was confirmed via gel electrophoresis.

One day prior to treatment, 2.5×10⁴A549 cells were seeded in 24-well plates. Immediately before treatment, the A549 cells were washed with Dulbecco's modified Eagle's medium (Gibco) then cultured in the presence of the potential cp-asiRNAs in OPTI-MEM buffer for 24 hours, at which point the asiRNA-containing OPTI-MEM media was replaced with a serum-containing media.

The level of F2RL1 mRNA expression was determined 48 hours after asiRNA treatment.

The cp-asiRNAs were incubated at 95° C. for 5 minutes and at 37° C. for 1 hour in OPTI-MEM buffer (Gibco). Proper strand annealing was confirmed via gel electrophoresis.

One day prior to treatment, 2.5×10⁴A549 cells were seeded in 24-well plates. Immediately before treatment, the A549 cells were washed with Dulbecco's modified Eagle's medium (Gibco) then cultured in the presence of the potential cp-asiRNAs in OPTI-MEM buffer for 24 hours, at which point the asiRNA-containing OPTI-MEM media was replaced with a serum-containing media.

The level of F2RL1 protein expression was determined via western blot 72 hours after asiRNA treatment. Briefly, the treated A549 cells were lysed with TX-100 lysis buffer (1% TX-100, 150 mM NaCl, 100 mM Tris (pH 8.8)). 10 μg of the total protein extracts were loaded onto a 10% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 3% BSA (Bioworld) and then incubated overnight at 4° C. in 3% BSA containing anti-F2RL1 antibody (Abcam) and anti-GAPDH antibody (Santa Cruz). The membrane was then washed with 1×TBST for 10 minutes three times and was incubated for 1 hour at the room temperature in 1×TBST with HRP-conjugated secondary antibody. The membrane was washed with 1×TBST for 10 minutes and treated with 1× ECL for 1 minute. The F2RL1 and GAPDH bands were then imaged using a Chemidoc instrument (Bio-rad).

Figure 27:
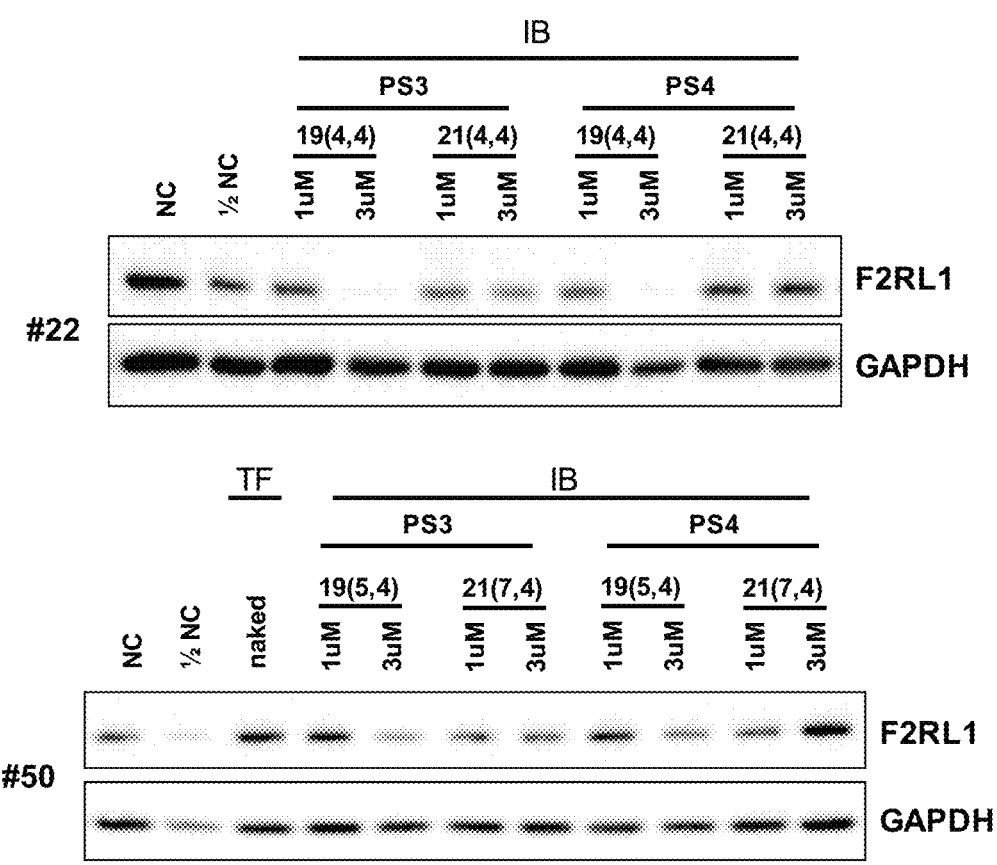
FIG. 27 shows the inhibition of F2RL1 protein expression by 8 exemplary cp-asiRNAs.

The results of the western blot assay are depicted in FIG. 27.

Example 21: In Vivo Efficacy Study

Figure 29:
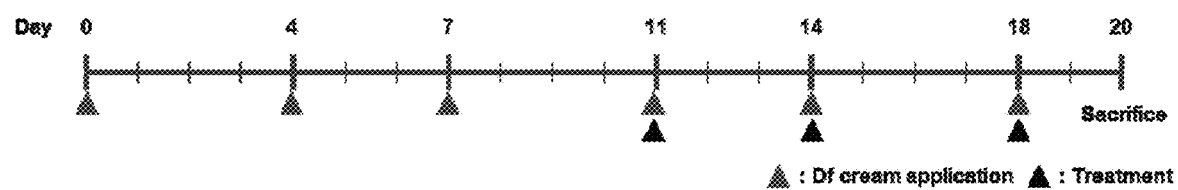
FIG. 29 shows the experimental timeline of cp-asiRNA treatment in an induced model of atopic dermatitis.

After shaving the dorsal region of NC/Nga mice, Dermatophagoides farinae body extract (D) cream was painted in presented schedule for inducing atopic dermatitis. At day 11, 14 and 18, cp-asiRNA was administered by intradermal injection or spreading of cream emulsified cp-asiRNA before Biostir® AD ointment application (FIG. 29). The dose of intradermal injection was 80 μg/50 μl*4 sites/head, and the dose of the cream emulsified cp-asiRNA was 800 μg/head. Mouse behavior was recorded and scratching behavior for 480 seconds were analyzed. Increased scratching time was observed in Dermatophagoides farinae body extract (Df) cream treated samples (1×PBS+Df). In both intradermal injection (FIG. 30, Part A) and cream emulsified cp-asiRNA application (FIG. 30, Part B) condition, IL4RA #5-PS3/19(4,4), TRPA1 #81-PS3/19(4,4), F2RL1 #22-PS4/19(4,4) treated samples showed reduced scratching time compared to vehicle control (1×PBS +Df). Results are presented as bar graph (mean±S.D) in FIG. 30. The results were statistically analyzed by Student's t-test methods (n=5).

Transepidermal water loss (TEWL) was measured using hand-held evaporimeter (VapoMeter, Delfin Technologies Ltd, Kuopio, Finland). Increased TEWL was observed in Dermatophagoides farinae body extract (Df) cream treated samples (1×PBS+Df). In both intradermal injection (FIG. 31, Part A) and cream emulsified cp-asiRNA application (FIG. 31, Part B) conditions, IL4RA #5-PS3/19(4,4), TRPA1 #81-PS3/19(4,4), F2RL1 #22-PS4/19(4,4) treated samples showed reduced TEWL compared to vehicle control (1×PBS +Df). Data are expressed as mean±S.E.M. The results were statistically analyzed by Student's t-test methods (n=5).

Figure 32:
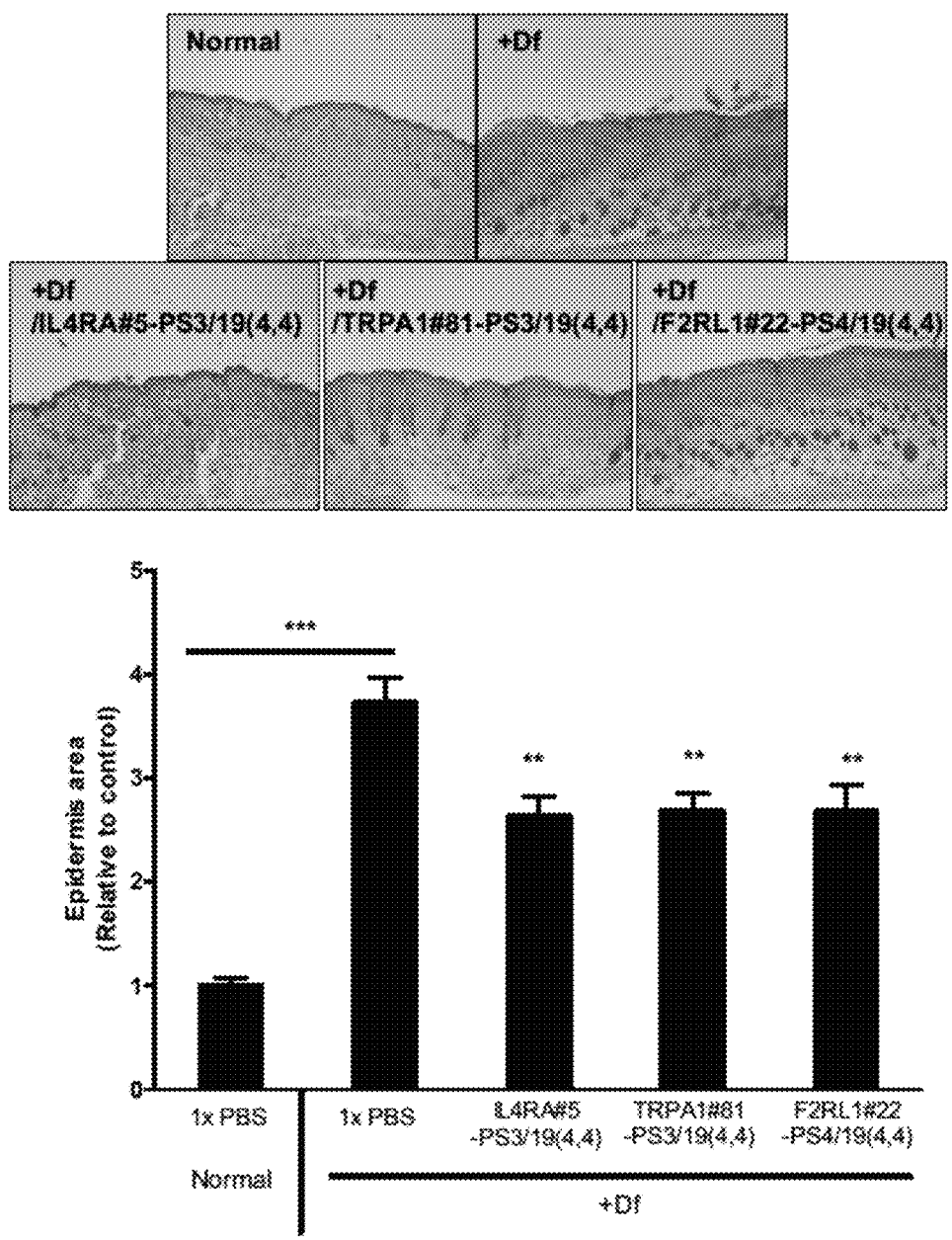
FIG. 32 shows H&E staining of skin sections and quantified epidermis area by analyzing skin section image of a rodent model of atopic dermatitis.
Figure 32:
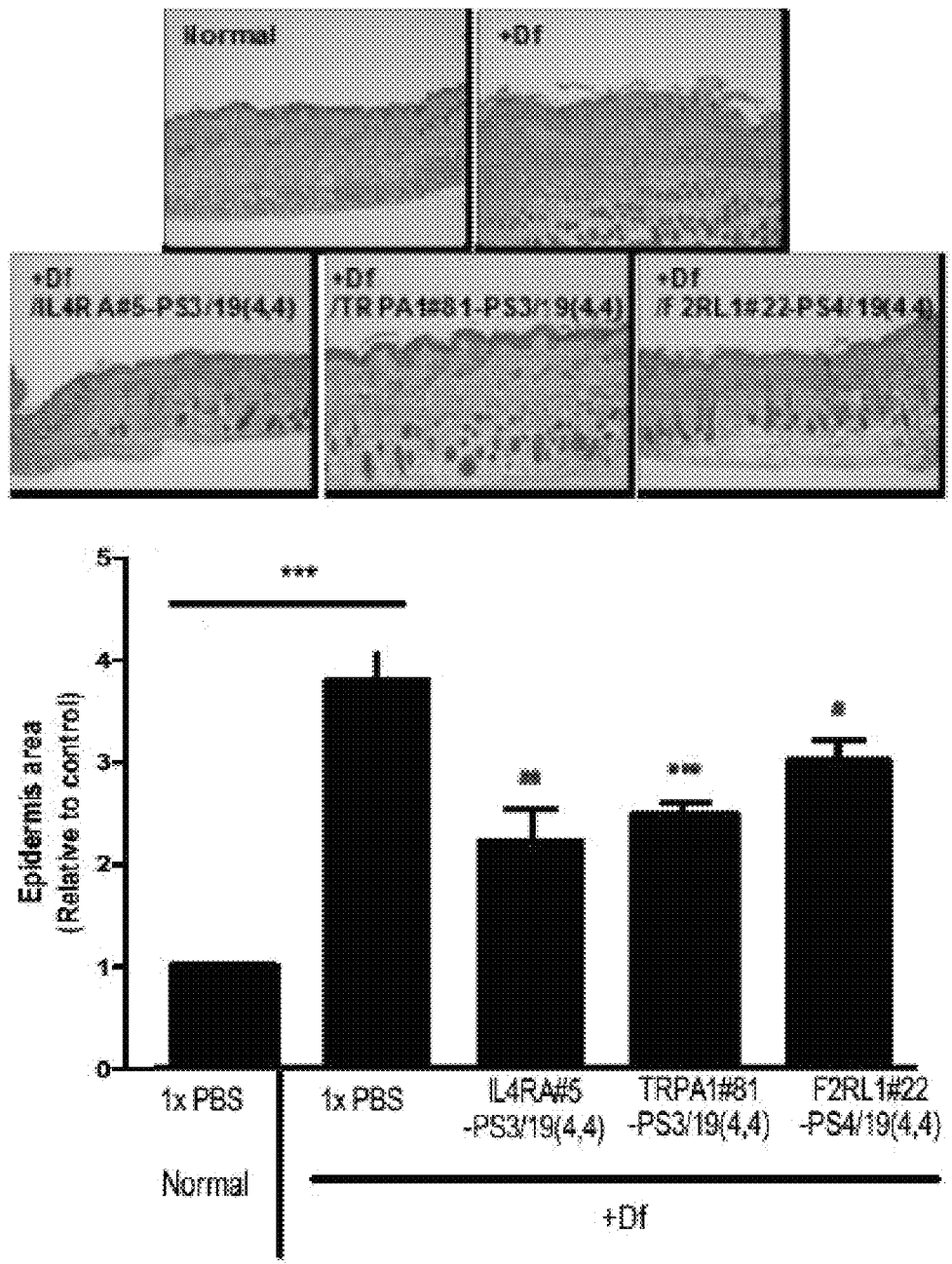

Histological analysis of treated skin region was conducted. Upper panels show H&E staining of skin sections and lower panels show quantified epidermis area by analyzing skin section image. Increased epidermis region thickness, hyperkeratosis, and acanthosis was observed in Dermatophagoides farinae body extract (Df) cream treated samples (+Df). In both intradermal injection (FIG. 32, Part A) and cream emulsified cp-asiRNA application (FIG. 32, Part B) condition, IL4RA #5-PS3/19(4,4), TRPA1 #81-PS3/19(4,4), F2RL1 #22-PS4/19(4,4) treated samples showed reduced symptoms caused by Df treatment compared to vehicle control (+Df). In both intradermal injection (FIG. 32, Part A) and cream emulsified cp-asiRNA application (FIG. 32, Part B) conditions, IL4RA #5-PS3/19(4,4), TRPA1 #81-PS3/19(4,4), F2RL1 #22-PS4/19(4,4) treated samples showed reduced level of epidermis thickness compared to vehicle control (1×PBS+Df). Data are expressed as mean±S.E.M. The results were statistically analyzed by student's t-test methods (n=5).

Mast cell infiltration analysis of treated skin region was conducted. FIG. 33 shows toluidine blue staining of skin sections and quantification results of the stained skin section image. Increased mast cell infiltration was observed in Dermatophagoides farinae body extract (Df) cream treated samples (+Df). In both intradermal injection (FIG. 33, Part A) and cream emulsified cp-asiRNA application (FIG. 33, Pan B) conditions, IL4RA #5-PS3/19(4,4), TRPA1 #81-PS3/19(4,4), F2RL1 #22-PS4/19(4,4) treated samples showed reduced mast cell infiltration compared to vehicle control el-DO. In both intradermal injection and cream emulsified cp-asjRNA application conditions, IL4RA #5-PS3/19(4,4), TRPA1 #81-PS3/19(4,4), F2RL1 #22-PS4/19(4,4) treated samples showed reduced level of mast cell infiltration area compared to vehicle control (1×PBS+Df). Data are expressed as mean±S.E.M. The results were statistically analyzed by Student's t-test methods (n=5).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A nucleic acid complex for inducing RNA interference to inhibit expression of F2RL1 gene, the nucleic acid complex comprising an antisense strand and a sense strand, the antisense strand being 21 nucleotides in length and having the base sequence of SEQ ID NO: 421, and the sense strand being 15 to 17 nucleotides in length and having sequence complementarity to the antisense strand.

2. The nucleic acid complex of claim 1, wherein the sense strand comprises the base sequence of SEQ ID NO: 420.

3. The nucleic acid complex of claim 1, wherein the 5' end of the antisense strand and the 3' end of the sense strand form a blunt end.

4. The nucleic acid complex of claim 3, wherein the RNA complex comprises a chemical modification.

5. The nucleic acid complex of claim 4, wherein the chemical modification is a 2'-O-methylated nucleoside, a phosphorothioate bond, or a hydrophobic moiety.

6. The nucleic acid complex of claim 5, wherein the hydrophobic moiety is a cholesterol moiety.

7. The nucleic acid complex of claim 5, wherein the nucleic acid complex is a modified nucleic acid complex selected from:

(a) a nucleic acid complex comprising:

a sense strand of:
(SEQ ID NO: 642)
5' mCUmGAmCCmUCmCUmCUmC*U*mG*U*cholesterol 3';
and an antisense strand of:
(SEQ ID NO: 643)
5' ACAGAGAGGAGGUCmAmGC*C*A*A*G 3';

(b) a nucleic acid complex comprising:

a sense strand of:
(SEQ ID NO: 644)
5' mCUmGAmCCmUCmCUmCUmC*U*mG*U*cholesterol 3';
and an antisense strand of:
(SEQ ID NO: 645)
5' ACAGAGAGGAGGUCmAmGmC*mC*A*A*G 3';

(c) a nucleic acid complex comprising:

```
a sense strand of:
                                    (SEQ ID NO: 646)
5' mCUmGAmCCmUCmCUmCUmC*U*mG*U*cholesterol 3';
and an antisense strand of
                                    (SEQ ID NO: 647)
5' ACAGAGAGGAGGUCmAmGmC*mC*mA*mA*mG 3';
```

(d) a nucleic acid complex comprising:

```
a sense strand of:
                                    (SEQ ID NO: 672)
5' mCUmGAmCCmUCmCUmCUmCU*mG*U*cholesterol 3';
and an antisense strand of
                                    (SEQ ID NO: 673)
5' ACAGAGAGGAGGUCmA*mG*mC*mC*A 3';
```

(e) a nucleic acid complex comprising:

```
a sense strand of:
                                    (SEQ ID NO: 674)
5' mCUmGAmCCmUCmCUmCUmCU*mG*U*cholesterol 3';
and an antisense strand of
                                    (SEQ ID NO: 675)
5' ACAGAGAGGAGGUCmAmGmC*mC*A*A*G 3';
```

(f) a nucleic acid complex comprising:

```
a sense strand of:
                                    (SEQ ID NO: 676)
5' mCUmGAmCCmUCmCUmCUmC*U*mG*U*cholesterol 3';
and an antisense strand of
                                    (SEQ ID NO: 677)
5' ACAGAGAGGAGGUCmA*mG*mC*mC*A 3';
``` wherein m represents 2'-O-methyl RNA and * represents a phosphorothioate bond.

8. The nucleic acid complex of claim 7, wherein the nucleic acid complex is capable of penetrating a cellular membrane of a cell in the absence of a delivery vehicle.

9. The nucleic acid complex of claim 1, wherein the nucleic acid complex is for delivery to a cell comprising an A549, an epithelial cell or a keratinocyte.

10. The nucleic acid complex of claim 1, wherein the nucleic acid complex is for delivery to a cell present in the skin or respiratory tract of a human subject.

11. A pharmaceutical composition comprising the nucleic acid complex of claim 1 and a pharmaceutically acceptable carrier.

12. The pharmaceutical composition of claim 11, wherein the pharmaceutical composition is formulated for inhalation.

13. The pharmaceutical composition of claim 11, wherein the pharmaceutical composition is formulated for topical administration.

14. The pharmaceutical composition of claim 11, wherein the pharmaceutical composition is formulated for intradermal injection.

15. A method for treating a disorder or condition related to F2RL1 expression, comprising administering the nucleic acid complex of claim 1 to a subject in need thereof, wherein the disorder or condition is atopic dermatitis.

16. The method of claim 15, comprising administering the nucleic acid complex topically.

17. The method of claim 15, comprising administering the nucleic acid complex via intradermal injection.

18. The method of claim 15, wherein the nucleic acid complex is a modified nucleic acid complex selected from:

(a) a nucleic acid complex comprising:

```
a sense strand of:
                                    (SEQ ID NO: 642)
5' mCUmGAmCCmUCmCUmCUmC*U*mG*U*cholesterol 3';
and an antisense strand of:
                                    (SEQ ID NO: 643)
5' ACAGAGAGGAGGUCmAmGC*C*A*A*G 3';
```

(b) a nucleic acid complex comprising:

```
a sense strand of:
                                    (SEQ ID NO: 644)
5' mCUmGAmCCmUCmCUmCUmC*U*mG*U*cholesterol 3';
and an antisense strand of:
                                    (SEQ ID NO: 645)
5' ACAGAGAGGAGGUCmAmGmC*mC*A*A*G 3';
```

(c) a nucleic acid complex comprising:

```
a sense strand of:
                                    (SEQ ID NO: 646)
5' mCUmGAmCCmUCmCUmCUmC*U*mG*U*cholesterol 3';
and an antisense strand of
                                    (SEQ ID NO: 647)
5' ACAGAGAGGAGGUCmAmGmC*mC*mA*mA*mG 3';
```

(d) a nucleic acid complex comprising:

```
a sense strand of:
                                    (SEQ ID NO: 672)
5' mCUmGAmCCmUCmCUmCUmCU*mG*U*cholesterol 3';
and an antisense strand of
                                    (SEQ ID NO: 673)
5' ACAGAGAGGAGGUCmA*mG*mC*mC*A 3';
```

(e) a nucleic acid complex comprising:

```
a sense strand of:
                                    (SEQ ID NO: 674)
5' mCUmGAmCCmUCmCUmCUmCU*mG*U*cholesterol 3';
and an antisense strand of
                                    (SEQ ID NO: 675)
5' ACAGAGAGGAGGUCmAmGmC*mC*A*A*G 3';
``` and (f) a nucleic acid complex comprising:

```
a sense strand of:
                                    (SEQ ID NO: 676)
5' mCUmGAmCCmUCmCUmCUmC*U*mG*U*cholesterol 3';
and an antisense strand of
                                    (SEQ ID NO: 677)
5' ACAGAGAGGAGGUCmA*mG*mC*mC*A 3';
``` wherein m represents 2'-O-methyl RNA and * represents a phosphorothioate bond.

19. The method of claim 18, wherein the nucleic acid complex is capable of penetrating the cellular membrane of the cell in the absence of a delivery vehicle.

* * * * *

SEQUENCE LISTING

```
<160> NUMBER OF SEQ ID NOS: 680

<210> SEQ ID NO 1
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aucaccaaga uuaaga                                                        16

<210> SEQ ID NO 2
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ucuuaaucuu ggugaugcug a                                               21

<210> SEQ ID NO 3
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ucaccaagau uaagaa                                                     16

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uucuuaaucu uggugaugcu g                                               21

<210> SEQ ID NO 5
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gccuucucaa gccugc                                                     16

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gcaggcuuga gaaggccuug u                                               21

<210> SEQ ID NO 7
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ccuucucaag ccugcu                                                     16

<210> SEQ ID NO 8
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
agcaggcuug agaaggccuu g                                              21

<210> SEQ ID NO 9
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9 ugcguuccg acuaca                                                     16

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uguagucgga gacgcaggug g                                              21

<210> SEQ ID NO 11
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gcgucuccga cuacau                                                    16

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
auguagucgg agacgcaggu g                                              21

<210> SEQ ID NO 13
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
guggaagggc uccuuc                                                    16

<210> SEQ ID NO 14
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 14
gaaggagccc uuccacagca g                                              21

<210> SEQ ID NO 15
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uggaagggcu ccuuca                                                    16

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ugaaggagcc cuuccacagc a                                              21

<210> SEQ ID NO 17
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
caucaccaag auuaag                                                    16

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
cuuaaucuug gugaugcuga c                                              21

<210> SEQ ID NO 19
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
caccaagauu aagaaa                                                    16

<210> SEQ ID NO 20
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 20
uuucuuaauc uuggugaugc u                                                    21

<210> SEQ ID NO 21
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ugggaucaga uuccca                                                          16

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ugggaaucug aucccaccau u                                                    21

<210> SEQ ID NO 23
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gggaucagau ucccaa                                                          16

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uugggaaucu gaucccacca u                                                    21

<210> SEQ ID NO 25
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
aagacagucc ucuggc                                                          16

<210> SEQ ID NO 26
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 26
gccagaggac ugucuugcug a                                              21

<210> SEQ ID NO 27
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
agacaguccu cuggcc                                                    16

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ggccagagga cugucuugcu g                                              21

<210> SEQ ID NO 29
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gacaguccuc uggcca                                                    16

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uggccagagg acugucuugc u                                              21

<210> SEQ ID NO 31
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
acaguccucu ggccag                                                    16

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 32
cuggccagag gacugucuug c                                              21

<210> SEQ ID NO 33
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
caguccucug gccaga                                                    16

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ucuggccaga ggacugucuu g                                              21

<210> SEQ ID NO 35
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
aguccucugg ccagag                                                    16

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
cucuggccag aggacugucu u                                              21

<210> SEQ ID NO 37
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
guccucuggc cagaga                                                    16

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ucucuggcca gaggacuguc u                                              21

<210> SEQ ID NO 39
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
cuccagcaug gggcag                                                    16

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cugccccaug cuggaggaca u                                              21

<210> SEQ ID NO 41
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ggcuaucagg aguuug                                                    16

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
caaacuccug auagccacug g                                              21

<210> SEQ ID NO 43
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
gcuaucagga guuugu                                                    16

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 44
acaaacuccu gauagccacu g                                              21

<210> SEQ ID NO 45
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cuucucaagc cugcuu                                                    16

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aagcaggcuu gagaaggccu u                                              21

<210> SEQ ID NO 47
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47 aaugggugg cuuugc                                                     16

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gcaaagccac cccauuggga g                                              21

<210> SEQ ID NO 49
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49 auggggggc uuugcu                                                     16

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
```
agcaaagcca ccccauuggg a                                          21

<210> SEQ ID NO 51
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cgucuccgac uacaug                                                16

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
cauguagucg gagacgcagg u                                          21

<210> SEQ ID NO 53
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
gacaguucac accaau                                                16

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
auugguguga acugucaggu u                                          21

<210> SEQ ID NO 55
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
acaguucaca ccaaug                                                16

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
cauuggugug aacugucagg u                                            21

<210> SEQ ID NO 57
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
caguucacac caaugu                                                  16

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
acauuggugu gaacugucag g                                            21

<210> SEQ ID NO 59
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
aguucacacc aauguc                                                  16

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
gacauuggug ugaacuguca g                                            21

<210> SEQ ID NO 61
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
cuggagugag uggagc                                                  16

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gcuccacuca cuccaggugg u                                            21

<210> SEQ ID NO 63
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
cagcaucacc aagauu                                                       16

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
aaucuuggug augcugacau a                                                 21

<210> SEQ ID NO 65
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
agcaucacca agauua                                                       16

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uaaucuuggu gaugcugaca u                                                 21

<210> SEQ ID NO 67
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
gcaucaccaa gauuaa                                                       16

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uuaaucuugg ugaugcugac a                                                 21

<210> SEQ ID NO 69
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uaagaaagaa uggugg                                                       16

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
ccaccauucu uucuuaaucu u                                                 21

<210> SEQ ID NO 71
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
aagaaagaau gguggg                                                       16

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
cccaccauuc uuucuuaauc u                                                 21

<210> SEQ ID NO 73
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
agaaagaaug guggga                                                       16

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
ucccaccauu cuuucuuaau c                                                 21

```
<210> SEQ ID NO 75
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gauucccaac ccagcc                                                        16

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
ggcuggguug ggaaucugau c                                                  21

<210> SEQ ID NO 77
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
agcaagacag uccucu                                                        16

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
agaggacugu cuugcugauc u                                                  21

<210> SEQ ID NO 79
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gcaagacagu ccucug                                                        16

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
cagaggacug ucuugcugau c                                                  21

<210> SEQ ID NO 81
```

```
<210> SEQ ID NO 81
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
caagacaguc cucugg                                                       16

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
ccagaggacu gucuugcuga u                                                 21

<210> SEQ ID NO 83
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
guuguuugag gccccg                                                       16

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
cggggccuca aacaacucca c                                                 21

<210> SEQ ID NO 85
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
aacagagagc cuguuc                                                       16

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gaacaggcuc ucuguuagcc g                                                 21

<210> SEQ ID NO 87
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
cugggagcag auccuc                                                    16

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
gaggaucugc ucccagguuu c                                              21

<210> SEQ ID NO 89
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
cuaucaggag uuugua                                                    16

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uacaaacucc ugauagccac u                                              21

<210> SEQ ID NO 91
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
ggcugguuac aaggcc                                                    16

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
ggccuuguaa ccagccucuc c                                              21

<210> SEQ ID NO 93
<211> LENGTH: 16
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 93
gcugguuaca aggccu                                                      16

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
aggccuugua accagccucu c                                                21

<210> SEQ ID NO 95
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
cugguuacaa ggccuu                                                      16

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
aaggccuugu aaccagccuc u                                                21

<210> SEQ ID NO 97
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ugguuacaag gccuuc                                                      16

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
gaaggccuug uaaccagccu c                                                21

<210> SEQ ID NO 99
<211> LENGTH: 16
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 99
gguuacaagg ccuucu                                                      16

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
agaaggccuu guaaccagcc u                                                21

<210> SEQ ID NO 101
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
guuacaaggc cuucuc                                                      16

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gagaaggccu uguaaccagc c                                                21

<210> SEQ ID NO 103
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
uuacaaggcc uucuca                                                      16

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
ugagaaggcc uuguaaccag c                                                21

<210> SEQ ID NO 105
<211> LENGTH: 16
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 105
gugcggccac cugaaa                                                          16

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
uuucaggugg ccgcacaggu g                                                    21

<210> SEQ ID NO 107
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
gcuguggcug cugcug                                                          16

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
cagcagcagc cacagcaagg a                                                    21

<210> SEQ ID NO 109
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
agccgagccu agaaac                                                          16

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
guuucuaggc ucggcuucua g                                                    21

<210> SEQ ID NO 111
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 111
gggaacauga aggucu                                                    16

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
agaccuucau guucccagag c                                              21

<210> SEQ ID NO 113
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
cuugcaggag cccacc                                                    16

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
ggugggcucc ugcaagaccu u                                              21

<210> SEQ ID NO 115
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
uugcaggagc ccaccu                                                    16

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
aggugggcuc cugcaagacc u                                              21

<210> SEQ ID NO 117
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
aguucacacc aauguc                                                       16

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
gacauuggug ugaacuguca g                                                 21

<210> SEQ ID NO 119
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uuucagaauc uauaac                                                       16

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
guuauagauu cugaaaucug c                                                 21

<210> SEQ ID NO 121
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
uauaacguga ccuacc                                                       16

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gguaggucac guuauagauu c                                                 21

<210> SEQ ID NO 123
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 123
caccuggagu gagugg                                                         16

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
ccacucacuc cagguggugu u                                                   21

<210> SEQ ID NO 125
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
accuggagug agugga                                                         16

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
uccacucacu ccagguggug u                                                   21

<210> SEQ ID NO 127
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ugugcuaugu cagcau                                                         16

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
augcugacau agcacaacag g                                                   21

<210> SEQ ID NO 129
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
```
gucagcauca ccaaga        16

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ucuuggugau gcugacauag c        21

<210> SEQ ID NO 131
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
ucagcaucac caagau        16

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
aucuugguga ugcugacaua g        21

<210> SEQ ID NO 133
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
uggugggauc agauuc        16

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
gaaucugauc ccaccauucu u        21

<210> SEQ ID NO 135
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135 gguggggauca gauucc                                               16

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ggaaucugau cccaccauuc u                                          21

<210> SEQ ID NO 137
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
gugcccacac uggaag                                                16

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
cuuccagugu gggcacuugg c                                          21

<210> SEQ ID NO 139
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
cuggaagaau ugucuu                                                16

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
aagacaauuc uuccagugug g                                          21

<210> SEQ ID NO 141
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
guccuccagc augggg                                                16

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ccccaugcug gaggacauuu c                                              21

<210> SEQ ID NO 143
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
aguggcuauc aggagu                                                    16

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
acuccugaua gccacuggug g                                              21

<210> SEQ ID NO 145
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
guggcuauca ggaguu                                                    16

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
aacuccugau agccacuggu g                                              21

<210> SEQ ID NO 147
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ugcgucuccg acuaca                                                    16

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
uguagucgga gacgcaggug g                                              21

<210> SEQ ID NO 149
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
gcgucuccga cuacau                                                    16

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
auguagucgg agacgcaggu g                                              21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
auguagucgg agacgcaggu g                                              21

<210> SEQ ID NO 152
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
ugcgucuccg acuaca                                                    16

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
uguagucgga gacgcaggu                                                 19

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 154
uguagucgga gacgcaggug g   21

<210> SEQ ID NO 155
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 155
gcgucuccga cuacau   16

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 156
auguagucgg agacgcagg   19

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 157
auguagucgg agacgcaggu g   21

<210> SEQ ID NO 158
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 158
ugaaggacgc ucucca   16

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 159
uggagagcgu ccuucagaau c   21

<210> SEQ ID NO 160

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
gaaggacgcu cuccac                                                    16

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
guggagagcg uccuucagaa u                                              21

<210> SEQ ID NO 162
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
ugaaggacgc ucucca                                                    16

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
uggagagcgu ccuucagaau c                                              21

<210> SEQ ID NO 164
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
aggacgcucu ccacuu                                                    16

<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
aaguggagag cguccuucag a                                              21

<210> SEQ ID NO 166
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ggacgcucuc cacuua                                                    16

<210> SEQ ID NO 167
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
uaaguggaga gcguccuuca g                                              21

<210> SEQ ID NO 168
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
gacgcucucc acuuau                                                    16

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
auaaguggag agcguccuuc a                                              21

<210> SEQ ID NO 170
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
uuuugcagcc aguuau                                                    16

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
auaacuggcu gcaaaaugca g                                              21

<210> SEQ ID NO 172
<211> LENGTH: 16
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 172
uuugcagcca guuaug                                                    16

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
cauaacuggc ugcaaaaugc a                                              21

<210> SEQ ID NO 174
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
uugcagccag uuaugg                                                    16

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
ccauaacugg cugcaaaaug c                                              21

<210> SEQ ID NO 176
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
ugcagccagu uauggg                                                    16

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
cccauaacug gcugcaaaau g                                              21

<210> SEQ ID NO 178
<211> LENGTH: 16
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 178
gcagccaguu augggc                                                         16

<210> SEQ ID NO 179
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
gcccauaacu ggcugcaaaa u                                                   21

<210> SEQ ID NO 180
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
cagccaguua ugggcg                                                         16

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
cgcccauaac uggcugcaaa a                                                   21

<210> SEQ ID NO 182
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
cauaagugau acgagg                                                         16

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
ccucguauca cuuaugucuu g                                                   21

<210> SEQ ID NO 184
<211> LENGTH: 16
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 184
auaagugaua cgaggc                                                        16

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
aagacauaag ugauacgagg c                                                  21

<210> SEQ ID NO 186
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uaagugauac gaggcu                                                        16

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
agccucguau cacuuauguc u                                                  21

<210> SEQ ID NO 188
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
aagugauacg aggcuu                                                        16

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
aagccucgua ucacuuaugu c                                                  21

<210> SEQ ID NO 190
<211> LENGTH: 16
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 190
cagugaccac aauggc                                                    16

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
gccauugugg ucacugagaa a                                              21

<210> SEQ ID NO 192
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
agugaccaca auggcu                                                    16

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
agccauugug gucacugaga a                                              21

<210> SEQ ID NO 194
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
gugaccacaa uggcug                                                    16

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
cagccauugu ggucacugag a                                              21

<210> SEQ ID NO 196
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
ugaccacaau ggcugg                                                    16

<210> SEQ ID NO 197
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
ccagccauug uggucacuga g                                              21

<210> SEQ ID NO 198
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
gaccacaaug gcugga                                                    16

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
uccagccauu guggucacug a                                              21

<210> SEQ ID NO 200
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
accacaaugg cuggac                                                    16

<210> SEQ ID NO 201
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
guccagccau uguggucacu g                                              21

<210> SEQ ID NO 202
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 202
cacucagacc augaag                                                          16

<210> SEQ ID NO 203
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
cuucaugguc ugaguguacc c                                                    21

<210> SEQ ID NO 204
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
acucagacca ugaagg                                                          16

<210> SEQ ID NO 205
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
ccuucauggu cugaguguac c                                                    21

<210> SEQ ID NO 206
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
cucagaccau gaaggu                                                          16

<210> SEQ ID NO 207
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
accuucaugg ucugagugua c                                                    21

<210> SEQ ID NO 208
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
```

```
ucagaccaug aagguc                                                   16
```

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209

```
gaccuucaug gucugagugu a                                             21
```

<210> SEQ ID NO 210
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210

```
cagaccauga agguca                                                   16
```

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211

```
ugaccuucau ggucugagug u                                             21
```

<210> SEQ ID NO 212
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212

```
agaccaugaa ggucau                                                   16
```

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213

```
augaccuuca uggucugagu g                                             21
```

<210> SEQ ID NO 214
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
gaccaugaag gucauu                                                           16

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
aaugaccuuc auggucugag u                                                     21

<210> SEQ ID NO 216
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
accaugaagg ucauuc                                                           16

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
gaaugaccuu cauggucuga g                                                     21

<210> SEQ ID NO 218
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
ccaugaaggu cauucu                                                           16

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
agaaugaccu ucauggucug a                                                     21

<210> SEQ ID NO 220
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
caugaagguc auucuu                                                           16

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
aagaaugacc uucauggucu g                                              21

<210> SEQ ID NO 222
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
augaagguca uucuug                                                    16

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
caagaaugac cuucaugguc u                                              21

<210> SEQ ID NO 224
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
ugaaggucau ucuuga                                                    16

<210> SEQ ID NO 225
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
ucaagaauga ccuucauggu c                                              21

<210> SEQ ID NO 226
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
gaaggucauu cuugau                                                    16

<210> SEQ ID NO 227
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
aucaagaaug accuucaugg u                                              21

<210> SEQ ID NO 228
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
aaggucauuc uugaua                                                    16

<210> SEQ ID NO 229
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
uaucaagaau gaccuucaug g                                              21

<210> SEQ ID NO 230
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
aggucauucu ugauac                                                    16

<210> SEQ ID NO 231
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
guaucaagaa ugaccuucau g                                              21

<210> SEQ ID NO 232
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
ggucauucuu gauacu                                                    16

```
<210> SEQ ID NO 233
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
aguaucaaga augaccuuca u                                              21

<210> SEQ ID NO 234
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
gucauucuug auacua                                                    16

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
uaguaucaag aaugaccuuc a                                              21

<210> SEQ ID NO 236
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
ucauucuuga uacuaa                                                    16

<210> SEQ ID NO 237
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
uuaguaucaa gaaugaccuu c                                              21

<210> SEQ ID NO 238
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
cagaagacaa guccug                                                    16

<210> SEQ ID NO 239
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
caggacuugu cuucugugga a                                                  21

<210> SEQ ID NO 240
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
uuuccaacag aaaagg                                                        16

<210> SEQ ID NO 241
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
ccuuuucugu uggaaaauuu g                                                  21

<210> SEQ ID NO 242
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
ggcaaugugg agcaau                                                        16

<210> SEQ ID NO 243
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
auugcuccac auugccacug c                                                  21

<210> SEQ ID NO 244
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
gcagguggaa cuucau                                                        16

<210> SEQ ID NO 245
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
augaaguucc accugcauag c                                              21

<210> SEQ ID NO 246
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
cagguggaac uucaua                                                    16

<210> SEQ ID NO 247
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
uaugaaguuc caccugcaua g                                              21

<210> SEQ ID NO 248
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
agguggaacu ucauac                                                    16

<210> SEQ ID NO 249
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
guaugaaguu ccaccugcau a                                              21

<210> SEQ ID NO 250
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
gguggaacuu cauacc                                                    16

<210> SEQ ID NO 251
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 251
gguaugaagu uccaccugca u                                              21

<210> SEQ ID NO 252
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
guggaacuuc auacca                                                    16

<210> SEQ ID NO 253
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
ugguaugaag uuccaccugc a                                              21

<210> SEQ ID NO 254
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
ugauuaugga aauacc                                                    16

<210> SEQ ID NO 255
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
gguauuucca uaaucaucca u                                              21

<210> SEQ ID NO 256
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
aauaccccuc ugcauu                                                    16

<210> SEQ ID NO 257
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 257
aaugcagagg gguauuucca u                                              21

<210> SEQ ID NO 258
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
uaccccucug cauugu                                                    16

<210> SEQ ID NO 259
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
acaaugcaga gggguauuuc c                                              21

<210> SEQ ID NO 260
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
accccucugc auugug                                                    16

<210> SEQ ID NO 261
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
cacaaugcag agggguauuu c                                              21

<210> SEQ ID NO 262
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
uugugcugua gaaaaa                                                    16

<210> SEQ ID NO 263
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 263
uuuuucuaca gcacaaugca g                                              21

<210> SEQ ID NO 264
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
acgcucucca cuuaua                                                    16

<210> SEQ ID NO 265
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
uauaagugga gagcguccuu c                                              21

<210> SEQ ID NO 266
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
ccacuuauau uagcaa                                                    16

<210> SEQ ID NO 267
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
uugcuaauau aaguggagag c                                              21

<210> SEQ ID NO 268
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
gugcccaagu agacau                                                    16

<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic

```
oligonucleotide

<400> SEQUENCE: 269
augucuacuu gggcaccuuu a                                              21

<210> SEQ ID NO 270
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
ugcccaagua gacaua                                                    16

<210> SEQ ID NO 271
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
uaugucuacu ugggcaccuu u                                              21

<210> SEQ ID NO 272
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
gcccaaguag acauaa                                                    16

<210> SEQ ID NO 273
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
uuaugucuac uugggcaccu u                                              21

<210> SEQ ID NO 274
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
cccaaguaga cauaaa                                                    16

<210> SEQ ID NO 275
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 275
uuuaugucua cuugggcacc u            21

<210> SEQ ID NO 276
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
caaguagaca uaaaag            16

<210> SEQ ID NO 277
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
cuuuuauguc uacuugggca c            21

<210> SEQ ID NO 278
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
aaguagacau aaaaga            16

<210> SEQ ID NO 279
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
ucuuuuaugu cuacuugggc a            21

<210> SEQ ID NO 280
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
aguagacaua aaagau            16

<210> SEQ ID NO 281
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 281
aucuuuuaug ucuacuuggg c                                              21

<210> SEQ ID NO 282
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
auuuaugcag augcaa                                                    16

<210> SEQ ID NO 283
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
uugcaucugc auaaauucag g                                              21

<210> SEQ ID NO 284
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
uaugggcgua ucaaua                                                    16

<210> SEQ ID NO 285
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
uauugauacg cccauaacug g                                              21

<210> SEQ ID NO 286
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
augggcguau caauac                                                    16

<210> SEQ ID NO 287
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
```

-continued guauugauac gcccauaacu g                                              21

<210> SEQ ID NO 288
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
cgaggcuucu gaauga                                                    16

<210> SEQ ID NO 289
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
ucauucagaa gccucguauc a                                              21

<210> SEQ ID NO 290
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
gaggcuucug aaugaa                                                    16

<210> SEQ ID NO 291
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
uucauucaga agccucguau c                                              21

<210> SEQ ID NO 292
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
aggcuucuga augaag                                                    16

<210> SEQ ID NO 293
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
cuucauucag aagccucgua u                                          21

<210> SEQ ID NO 294
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
ucucagugac cacaau                                                16

<210> SEQ ID NO 295
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
auugugguca cugagaaaca a                                          21

<210> SEQ ID NO 296
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
cucagugacc acaaug                                                16

<210> SEQ ID NO 297
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
cauugugguc acugagaaac a                                          21

<210> SEQ ID NO 298
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
acacucagac caugaa                                                16

<210> SEQ ID NO 299
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
uucauggucu gaguguaccc g                                          21

<210> SEQ ID NO 300
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
acugucuugg ucucau                                                   16

<210> SEQ ID NO 301
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
augagaccaa gacaguaaga u                                             21

<210> SEQ ID NO 302
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
cugucuuggu cucaua                                                   16

<210> SEQ ID NO 303
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
uaugagacca agacaguaag a                                             21

<210> SEQ ID NO 304
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ugucuugguc ucauac                                                   16

<210> SEQ ID NO 305
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
guaugagacc aagacaguaa g                                             21

<210> SEQ ID NO 306
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
auauuugggu auugca                                                        16

<210> SEQ ID NO 307
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
ugcaauaccc aaauauacuu g                                                  21

<210> SEQ ID NO 308
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
ggguauugca aagaag                                                        16

<210> SEQ ID NO 309
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
cuucuuugca auacccaaau a                                                  21

<210> SEQ ID NO 310
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
uuuuccaaca gaaaag                                                        16

<210> SEQ ID NO 311
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
cuuuucuguu ggaaaauuug c                                                  21

```
<210> SEQ ID NO 312
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
gcaaugugga gcaauu                                                        16

<210> SEQ ID NO 313
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
aauugcucca cauugccacu g                                                  21

<210> SEQ ID NO 314
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
uuuuggacuc agcuuu                                                        16

<210> SEQ ID NO 315
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
aaagcugagu ccaaaagcca g                                                  21

<210> SEQ ID NO 316
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
uuuggacuca gcuuuu                                                        16

<210> SEQ ID NO 317
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
aaaagcugag uccaaaagcc a                                                  21

<210> SEQ ID NO 318
```

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
uuggacucag cuuuua                                                        16

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
uaaaagcuga guccaaaagc c                                                  21

<210> SEQ ID NO 320
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
cuaggagaua ucaauu                                                        16

<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
aauugauauc uccuagcauc a                                                  21

<210> SEQ ID NO 322
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
uaggagauau caauua                                                        16

<210> SEQ ID NO 323
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
uaauugauau cuccuagcau c                                                  21

<210> SEQ ID NO 324
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
ggagauauca auuauc                                                     16

<210> SEQ ID NO 325
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
gauaauugau aucuccuagc a                                               21

<210> SEQ ID NO 326
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
gagauaucaa uuaucg                                                     16

<210> SEQ ID NO 327
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
cgauaauuga uaucuccuag c                                               21

<210> SEQ ID NO 328
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
agauaucaau uaucga                                                     16

<210> SEQ ID NO 329
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
ucgauaauug auaucuccua g                                               21

<210> SEQ ID NO 330
<211> LENGTH: 16
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 330
auauuugucc caauug                                                     16

<210> SEQ ID NO 331
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
caauugggac aaauauugug a                                               21

<210> SEQ ID NO 332
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
uauuuguccc aauugu                                                     16

<210> SEQ ID NO 333
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
acaauuggga caaauauugu g                                               21

<210> SEQ ID NO 334
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
ccaauugucc ucauga                                                     16

<210> SEQ ID NO 335
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
ucaugaggac aauugggaca a                                               21

<210> SEQ ID NO 336
<211> LENGTH: 16
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 336
caauuguccu caugaa                                                       16

<210> SEQ ID NO 337
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
uucaugagga caauugggac a                                                 21

<210> SEQ ID NO 338
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
ugcugagguc cagaaa                                                       16

<210> SEQ ID NO 339
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
uuucuggacc ucagcaaugu c                                                 21

<210> SEQ ID NO 340
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
agaggauagc uaugca                                                       16

<210> SEQ ID NO 341
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
ugcauagcua uccucuucaa u                                                 21

<210> SEQ ID NO 342
<211> LENGTH: 16
<212> TYPE: RNA
<213> ORGANISM: Artificial Sequence
<220> FEATURE:
```

<223> OTHER INFORMATION: Description of Artificial Sequence: Synthetic
     oligonucleotide

<400> SEQUENCE: 342
gaggauagcu augcag                                                          16

<210> SEQ ID NO 343
<211> LENGTH: 21
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 343
cugcauagcu auccucuuca a                                                    21

<210> SEQ ID NO 344
<211> LENGTH: 16
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 344
uaugcaggug gaacuu                                                          16

<210> SEQ ID NO 345
<211> LENGTH: 21
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 345
aaguuccacc ugcauagcua u                                                    21

<210> SEQ ID NO 346
<211> LENGTH: 16
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 346
augcaggugg aacuuc                                                          16

<210> SEQ ID NO 347
<211> LENGTH: 21
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 347
gaaguuccac cugcauagcu a                                                    21

<210> SEQ ID NO 348
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 348
ugcaggugga acuuca                                                        16

<210> SEQ ID NO 349
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
ugaaguucca ccugcauagc u                                                  21

<210> SEQ ID NO 350
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
aacagcauga gcucau                                                        16

<210> SEQ ID NO 351
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
augagcucau gcuguuuuc c                                                   21

<210> SEQ ID NO 352
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
cagaagaugg agauca                                                        16

<210> SEQ ID NO 353
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
ugaucuccau cuucugaaug a                                                  21

<210> SEQ ID NO 354
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 354
agaagaugga gaucau                                                    16

<210> SEQ ID NO 355
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
augaucucca ucuucugaau g                                              21

<210> SEQ ID NO 356
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
gaagauggag aucauc                                                    16

<210> SEQ ID NO 357
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
gaugaucucc aucuucugaa u                                              21

<210> SEQ ID NO 358
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
aagauggaga ucaucu                                                    16

<210> SEQ ID NO 359
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
agaugaucuc caucuucuga a                                              21

<210> SEQ ID NO 360
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 360
gauggagauc aucucu                                                      16

<210> SEQ ID NO 361
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
agagaugauc uccaucuucu g                                                21

<210> SEQ ID NO 362
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
acacucagac caugaa                                                      16

<210> SEQ ID NO 363
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
uucauggucu gaguguaccc g                                                21

<210> SEQ ID NO 364
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
uucauggucu gaguguaccc g                                                21

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
uucauggucu gaguguaccc g                                                21

<210> SEQ ID NO 366
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
```

```
uuggacucag cuuuua                                              16

<210> SEQ ID NO 367
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
uaaaagcuga guccaaaagc c                                        21

<210> SEQ ID NO 368
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
uaaaagcuga guccaaaagc c                                        21

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
uaaaagcuga guccaaaagc c                                        21

<210> SEQ ID NO 370
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
acacucagac caugaa                                              16

<210> SEQ ID NO 371
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
acacucagac caugaa                                              16

<210> SEQ ID NO 372
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
```

```
uucauggucu gaguguacc                                              19
```

<210> SEQ ID NO 373
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373

```
uucauggucu gaguguaccc g                                           21
```

<210> SEQ ID NO 374
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374

```
uuggacucag cuuuua                                                 16
```

<210> SEQ ID NO 375
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375

```
uuggacucag cuuuua                                                 16
```

<210> SEQ ID NO 376
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376

```
uaaaagcuga guccaaaag                                              19
```

<210> SEQ ID NO 377
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377

```
uaaaagcuga guccaaaagc c                                           21
```

<210> SEQ ID NO 378
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378

```
ccucucuguc aucugg                                                 16
```

```
<210> SEQ ID NO 379
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
ccagaugaca gagaggaggu c                                              21

<210> SEQ ID NO 380
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
cucucuguca ucuggu                                                    16

<210> SEQ ID NO 381
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
accagaugac agagaggagg u                                              21

<210> SEQ ID NO 382
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
ucucugucau cugguu                                                    16

<210> SEQ ID NO 383
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
aaccagauga cagagaggag g                                              21

<210> SEQ ID NO 384
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
cucugucauc ugguuc                                                    16
```

<210> SEQ ID NO 385
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
gaaccagaug acagagagga g                                              21

<210> SEQ ID NO 386
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
ucugucaucu gguucc                                                    16

<210> SEQ ID NO 387
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
ggaaccagau gacagagagg a                                              21

<210> SEQ ID NO 388
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
cugucaucug guuccc                                                    16

<210> SEQ ID NO 389
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
gggaaccaga ugacagagag g                                              21

<210> SEQ ID NO 390
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
ugucaucugg uuccccc                                                   16

```
<210> SEQ ID NO 391
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
ggggaaccag augacagaga g                                              21

<210> SEQ ID NO 392
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
caccaucccu uuguau                                                    16

<210> SEQ ID NO 393
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
auacaaaggg auggugacca g                                              21

<210> SEQ ID NO 394
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
accaucccuu uguaug                                                    16

<210> SEQ ID NO 395
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
cauacaaagg gauggugacc a                                              21

<210> SEQ ID NO 396
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
ccaucccuuu guaugu                                                    16

<210> SEQ ID NO 397
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
acauacaaag ggauggugac c                                              21

<210> SEQ ID NO 398
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
caucccuuug uauguc                                                    16

<210> SEQ ID NO 399
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
gacauacaaa gggaugguga c                                              21

<210> SEQ ID NO 400
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
acaaagggau ggugac                                                    16

<210> SEQ ID NO 401
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
gucaccaucc cuuuguaugu c                                              21

<210> SEQ ID NO 402
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
uucaauuacu uccucu                                                    16

<210> SEQ ID NO 403
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
agaggaagua auugaacaug u                                              21

<210> SEQ ID NO 404
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
ucaauuacuu ccucuc                                                    16

<210> SEQ ID NO 405
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
gagaggaagu aauugaacau g                                              21

<210> SEQ ID NO 406
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
cuuugucuau uacuuu                                                    16

<210> SEQ ID NO 407
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
aaaguaauag acaaaggggu c                                              21

<210> SEQ ID NO 408
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
uuugucuauu acuuug                                                    16

<210> SEQ ID NO 409
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 409
caaaguaaua gacaaagggg u                                           21

<210> SEQ ID NO 410
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
uugucuauua cuuugu                                                 16

<210> SEQ ID NO 411
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
acaaaguaau agacaaaggg g                                           21

<210> SEQ ID NO 412
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
auggccaauc uggccu                                                 16

<210> SEQ ID NO 413
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
aggccagauu ggccauguaa a                                           21

<210> SEQ ID NO 414
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
uuggcugacc uccucu                                                 16

<210> SEQ ID NO 415
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 415
agaggagguc agccaaggcc a                                              21

<210> SEQ ID NO 416
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
ggcugaccuc cucucu                                                    16

<210> SEQ ID NO 417
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
agaggaggag ucagccaagg c                                              21

<210> SEQ ID NO 418
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
gcugaccucc ucucug                                                    16

<210> SEQ ID NO 419
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
cagagaggag gucagccaag g                                              21

<210> SEQ ID NO 420
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
cugaccuccu cucugu                                                    16

<210> SEQ ID NO 421
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 421
acagagagga ggucagccaa g                                                    21

<210> SEQ ID NO 422
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
ugaccuccuc ucuguc                                                          16

<210> SEQ ID NO 423
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
gacagagagg aggucagcca a                                                    21

<210> SEQ ID NO 424
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
gaccuccucu cuguca                                                          16

<210> SEQ ID NO 425
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
ugacagagag gaggucagcc a                                                    21

<210> SEQ ID NO 426
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426 accuccucu ugucau                                                           16

<210> SEQ ID NO 427
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 427
augacagaga ggaggucagc c					21

<210> SEQ ID NO 428
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
ccuccucucu gucauc					16

<210> SEQ ID NO 429
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
gaugacagag aggaggucag c					21

<210> SEQ ID NO 430
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
cuccucucug ucaucu					16

<210> SEQ ID NO 431
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
agaugacaga gaggagguca g					21

<210> SEQ ID NO 432
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
uccucucugu caucug					16

<210> SEQ ID NO 433
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
cagaugacag agaggagguc a                                              21

<210> SEQ ID NO 434
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
gucaucuggu uccccu                                                    16

<210> SEQ ID NO 435
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
aggggaacca gaugacagag a                                              21

<210> SEQ ID NO 436
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
acauggcaac aacugg                                                    16

<210> SEQ ID NO 437
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
ccaguuguug ccauguaugu g                                              21

<210> SEQ ID NO 438
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
uauuggcuuu uucuau                                                    16

<210> SEQ ID NO 439
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
auagaaaaag ccaauaagca c                                              21

<210> SEQ ID NO 440
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
auuggcuuuu ucuaug                                                    16

<210> SEQ ID NO 441
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
cauagaaaaa gccaauaagc a                                              21

<210> SEQ ID NO 442
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
uuggcuuuuu cuaugg                                                    16

<210> SEQ ID NO 443
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
ccauagaaaa agccaauaag c                                              21

<210> SEQ ID NO 444
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
uucuauggca acaugu                                                    16

<210> SEQ ID NO 445
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
acauguugcc auagaaaaag c                                            21

<210> SEQ ID NO 446
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
ucuauggcaa caugua                                                  16

<210> SEQ ID NO 447
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
uacauguugc cauagaaaaa g                                            21

<210> SEQ ID NO 448
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
cucuucauga ccugcc                                                  16

<210> SEQ ID NO 449
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
ggcaggucau gaagagaaug g                                            21

<210> SEQ ID NO 450
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
ucuucaugac cugccu                                                  16

<210> SEQ ID NO 451
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
aggcagguca ugaagagaau g                                         21

<210> SEQ ID NO 452
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
cuucaugacc ugccuc                                               16

<210> SEQ ID NO 453
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
gaggcagguc augaagagaa u                                         21

<210> SEQ ID NO 454
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
uucaugaccu gccuca                                               16

<210> SEQ ID NO 455
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
ugaggcaggu caugaagaga a                                         21

<210> SEQ ID NO 456
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
ucaugaccug ccucag                                               16

<210> SEQ ID NO 457
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
cugaggcagg ucaugaagag a                                         21

```
<210> SEQ ID NO 458
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
caugaccugc cucagu                                                     16

<210> SEQ ID NO 459
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
acugaggcag gucaugaaga g                                               21

<210> SEQ ID NO 460
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
ugccucagug ugcaga                                                     16

<210> SEQ ID NO 461
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
ucugcacacu gaggcagguc a                                               21

<210> SEQ ID NO 462
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
gccucagugu gcagag                                                     16

<210> SEQ ID NO 463
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
cucugcacac ugaggcaggu c                                               21
```

<210> SEQ ID NO 464
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
cucagugugc agaggu                                                     16

<210> SEQ ID NO 465
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
accucugcac acugaggcag g                                               21

<210> SEQ ID NO 466
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
ucagugugca gaggua                                                     16

<210> SEQ ID NO 467
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
uaccucugca cacugaggca g                                               21

<210> SEQ ID NO 468
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468
caucgugaac cccaug                                                     16

<210> SEQ ID NO 469
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
caugggguuc acgaugaccc a                                               21

```
<210> SEQ ID NO 470
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
aucgugaacc ccaugg                                                      16

<210> SEQ ID NO 471
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
ccaugggguu cacgaugacc c                                                21

<210> SEQ ID NO 472
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
ucgugaaccc cauggg                                                      16

<210> SEQ ID NO 473
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
cccauggggu ucacgaugac c                                                21

<210> SEQ ID NO 474
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
caggaagaag gcaaac                                                      16

<210> SEQ ID NO 475
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
guuugccuuc uuccuggagu g                                                21

<210> SEQ ID NO 476
```

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
aggaagaagg caaaca                                                    16

<210> SEQ ID NO 477
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
uguuugccuu cuuccuggag u                                              21

<210> SEQ ID NO 478
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
ggaagaaggc aaacau                                                    16

<210> SEQ ID NO 479
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
auguuugccu ucuuccugga g                                              21

<210> SEQ ID NO 480
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
gucaccaucc cuuugu                                                    16

<210> SEQ ID NO 481
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
acaaagggau ggugaccagc a                                              21

<210> SEQ ID NO 482
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
ucaccauccc uuugua                                                         16

<210> SEQ ID NO 483
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
uacaaaggga uggugaccag c                                                   21

<210> SEQ ID NO 484
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
aucccuuugu augucg                                                         16

<210> SEQ ID NO 485
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
cgacauacaa agggauggug a                                                   21

<210> SEQ ID NO 486
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
uguaugucgu gaagca                                                         16

<210> SEQ ID NO 487
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
ugcuucacga cauacaaagg g                                                   21

<210> SEQ ID NO 488
<211> LENGTH: 16
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 488
guaugucgug aagcag                                                    16

<210> SEQ ID NO 489
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
cugcuucacg acauacaaag g                                              21

<210> SEQ ID NO 490
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
uaugucguga agcaga                                                    16

<210> SEQ ID NO 491
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
ucugcuucac gacauacaaa g                                              21

<210> SEQ ID NO 492
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
gucgugaagc agacca                                                    16

<210> SEQ ID NO 493
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
uggucugcuu cacgacauac a                                              21

<210> SEQ ID NO 494
<211> LENGTH: 16
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 494
ucgugaagca gaccau                                                        16

<210> SEQ ID NO 495
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
auggucugcu ucacgacaua c                                                  21

<210> SEQ ID NO 496
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
cgugaagcag accauc                                                        16

<210> SEQ ID NO 497
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
gauggucugc uucacgacau a                                                  21

<210> SEQ ID NO 498
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
gugaagcaga ccaucu                                                        16

<210> SEQ ID NO 499
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
agauggucug cuucacgaca u                                                  21

<210> SEQ ID NO 500
<211> LENGTH: 16
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 500
gggagacaug uucaau                                                            16

<210> SEQ ID NO 501
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
auugaacaug ucucccacca a                                                      21

<210> SEQ ID NO 502
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
ggagacaugu ucaauu                                                            16

<210> SEQ ID NO 503
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
aauugaacau gucucccacc a                                                      21

<210> SEQ ID NO 504
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
gagacauguu caauua                                                            16

<210> SEQ ID NO 505
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
uaauugaaca ugucucccac c                                                      21

<210> SEQ ID NO 506
<211> LENGTH: 16
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 506
agacauguuc aauuac                                                         16

<210> SEQ ID NO 507
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
guaauugaac augucuccca c                                                   21

<210> SEQ ID NO 508
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
gacauguuca auuacu                                                         16

<210> SEQ ID NO 509
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
aguaauugaa caugucuccc a                                                   21

<210> SEQ ID NO 510
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
acauguucaa uuacuu                                                         16

<210> SEQ ID NO 511
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
aaguaauuga acaugucucc c                                                   21

<210> SEQ ID NO 512
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
cauguucaau uacuuc                                                      16

<210> SEQ ID NO 513
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
gaaguaauug aacaugucuc c                                                21

<210> SEQ ID NO 514
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
auguucaauu acuucc                                                      16

<210> SEQ ID NO 515
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
ggaaguaauu gaacaugucu c                                                21

<210> SEQ ID NO 516
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
uguucaauua cuuccu                                                      16

<210> SEQ ID NO 517
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
aggaaguaau ugaacauguc u                                                21

<210> SEQ ID NO 518
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 518
caauuacuuc cucucu                                                      16

<210> SEQ ID NO 519
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
agagaggaag uaauugaaca u                                                21

<210> SEQ ID NO 520
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
uuccucucuc uggcca                                                      16

<210> SEQ ID NO 521
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
uggccagaga gaggaaguaa u                                                21

<210> SEQ ID NO 522
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
ccucucucug gccauu                                                      16

<210> SEQ ID NO 523
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
aauggccaga gagaggaagu a                                                21

<210> SEQ ID NO 524
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
```
cucucucugg ccauug                                            16

<210> SEQ ID NO 525
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
caauggccag agagaggaag u                                      21

<210> SEQ ID NO 526
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
ucucucuggc cauugg                                            16

<210> SEQ ID NO 527
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
ccaauggcca gagagaggaa g                                      21

<210> SEQ ID NO 528
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
ugaaaacuca gagaag                                            16

<210> SEQ ID NO 529
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
cuucucugag uuuucaucca u                                      21

<210> SEQ ID NO 530
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530

```
gaaaacucag agaaga                                                          16
```

<210> SEQ ID NO 531
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531

```
ucuucucuga guuuucaucc a                                                    21
```

<210> SEQ ID NO 532
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532

```
aaaacucaga gaagaa                                                          16
```

<210> SEQ ID NO 533
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533

```
uucuucucug aguuuucauc c                                                    21
```

<210> SEQ ID NO 534
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534

```
aaacucagag aagaaa                                                          16
```

<210> SEQ ID NO 535
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535

```
uuucuucucu gaguuuucau c                                                    21
```

<210> SEQ ID NO 536
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536

```
acucagagaa gaaaag                                                          16
```

<210> SEQ ID NO 537
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537 cuuucuucu cugaguuuuc a                                          21

<210> SEQ ID NO 538
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
cucagagaag aaaagg                                               16

<210> SEQ ID NO 539
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539 ccuuucuuc ucugaguuuu c                                          21

<210> SEQ ID NO 540
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
cugcaucgac cccuuu                                               16

<210> SEQ ID NO 541
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 541
aaaggggucg augcagcugu u                                         21

<210> SEQ ID NO 542
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
ugcaucgacc ccuuug                                               16

<210> SEQ ID NO 543
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
caaagggguc gaugcagcug u                                               21

<210> SEQ ID NO 544
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
gcaucgaccc cuuugu                                                     16

<210> SEQ ID NO 545
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545 acaaggggu cgaugcagcu g                                                21

<210> SEQ ID NO 546
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
caucgacccc uuuguc                                                     16

<210> SEQ ID NO 547
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
gacaaagggg ucgaugcagc u                                               21

<210> SEQ ID NO 548
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
aucgaccccu uugucu                                                     16

```
<210> SEQ ID NO 549
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
agacaaaggg gucgaugcag c                                              21

<210> SEQ ID NO 550
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
ucgaccccuu ugucua                                                    16

<210> SEQ ID NO 551
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
uagacaaagg ggucgaugca g                                              21

<210> SEQ ID NO 552
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
cgaccccuuu gucuau                                                    16

<210> SEQ ID NO 553
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
auagacaaag gggucgaugc a                                              21

<210> SEQ ID NO 554
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
gaccccuuug ucuauu                                                    16

<210> SEQ ID NO 555
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555
aauagacaaa ggggucgaug c                                               21

<210> SEQ ID NO 556
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
accccuuugu cuauua                                                     16

<210> SEQ ID NO 557
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
uaauagacaa agggucgau g                                                21

<210> SEQ ID NO 558
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
ccccuuuguc uauuac                                                     16

<210> SEQ ID NO 559
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 559
guaauagaca aagggucga u                                                21

<210> SEQ ID NO 560
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560
cccuuugucu auuacu                                                     16

<210> SEQ ID NO 561
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 561
aguaauagac aaaggggucg a                                          21

<210> SEQ ID NO 562
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
ccuuugucua uuacuu                                                16

<210> SEQ ID NO 563
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 563
aaguaauaga caaagggguc g                                          21

<210> SEQ ID NO 564
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
ugucuauuac uuuguu                                                16

<210> SEQ ID NO 565
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
aacaaaguaa uagacaaagg g                                          21

<210> SEQ ID NO 566
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
ugccgaagug uccgca                                                16

<210> SEQ ID NO 567
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 567
ugcggacacu ucggcaaagg a                                              21

<210> SEQ ID NO 568
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
gccgaagugu ccgcac                                                    16

<210> SEQ ID NO 569
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 569
gugcggacac uucggcaaag g                                              21

<210> SEQ ID NO 570
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 570 ccgaagoguc cgcacu                                                    16

<210> SEQ ID NO 571
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 571
agugcggaca cuucggcaaa g                                              21

<210> SEQ ID NO 572
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 572
cgaagugucc gcacug                                                    16

<210> SEQ ID NO 573
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 573
cagugcggac acuucggcaa a                                              21

<210> SEQ ID NO 574
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
gaaguguccg cacugu                                                    16

<210> SEQ ID NO 575
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
acagugcgga cacuucggca a                                              21

<210> SEQ ID NO 576
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
aaguguccgc acugua                                                    16

<210> SEQ ID NO 577
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
uacagugcgg acacuucggc a                                              21

<210> SEQ ID NO 578
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
gucaucuggu uccccu                                                    16

<210> SEQ ID NO 579
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 579
aggggaacca gaugacagag a                                              21

<210> SEQ ID NO 580
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
gucaucuggu uccccu                                                    16

<210> SEQ ID NO 581
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
aggggaacca gaugacagag a                                              21

<210> SEQ ID NO 582
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
gucaucuggu uccccu                                                    16

<210> SEQ ID NO 583
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
aggggaacca gaugacagag a                                              21

<210> SEQ ID NO 584
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
gucaucuggu uccccu                                                    16

<210> SEQ ID NO 585
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
oligonucleotide

<400> SEQUENCE: 585
aggggaacca gaugacagag a                                              21

<210> SEQ ID NO 586
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
aggaagaagg caaaca                                                    16

<210> SEQ ID NO 587
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 587
uguuugccuu cuuccuggag u                                              21

<210> SEQ ID NO 588
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
aggaagaagg caaaca                                                    16

<210> SEQ ID NO 589
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
uguuugccuu cuuccuggag u                                              21

<210> SEQ ID NO 590
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
aggaagaagg caaaca                                                    16

<210> SEQ ID NO 591
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 591
uguuugccuu cuuccuggag u                    21

<210> SEQ ID NO 592
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
aggaagaagg caaaca                          16

<210> SEQ ID NO 593
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 593
uguuugccuu cuuccuggag u                    21

<210> SEQ ID NO 594
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
uaugucguga agcaga                          16

<210> SEQ ID NO 595
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
ucugcuucac gacauacaaa g                    21

<210> SEQ ID NO 596
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
uaugucguga agcaga                          16

<210> SEQ ID NO 597
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 597
ucugcuucac gacauacaaa g                                              21

<210> SEQ ID NO 598
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
uaugucguga agcaga                                                    16

<210> SEQ ID NO 599
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 599
ucugcuucac gacauacaaa g                                              21

<210> SEQ ID NO 600
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
uaugucguga agcaga                                                    16

<210> SEQ ID NO 601
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
ucugcuucac gacauacaaa g                                              21

<210> SEQ ID NO 602
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602
gagacauguu caauua                                                    16

<210> SEQ ID NO 603
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
```
uaauugaaca ugucucccac c                          21

<210> SEQ ID NO 604
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
gagacauguu caauua                                16

<210> SEQ ID NO 605
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
uaauugaaca ugucucccac c                          21

<210> SEQ ID NO 606
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
gagacauguu caauua                                16

<210> SEQ ID NO 607
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
uaauugaaca ugucucccac c                          21

<210> SEQ ID NO 608
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608
gagacauguu caauua                                16

<210> SEQ ID NO 609
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 609
uaauugaaca ugucucccac c    21

<210> SEQ ID NO 610
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
acauguucaa uuacuu    16

<210> SEQ ID NO 611
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 611
aaguaauuga acaugucucc c    21

<210> SEQ ID NO 612
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
acauguucaa uuacuu    16

<210> SEQ ID NO 613
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
aaguaauuga acaugucucc c    21

<210> SEQ ID NO 614
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
acauguucaa uuacuu    16

<210> SEQ ID NO 615
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
aaguaauuga acaugucucc c    21

<210> SEQ ID NO 616
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 616
acauguucaa uuacuu                                                    16

<210> SEQ ID NO 617
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 617
aaguaauuga acaugucucc c                                              21

<210> SEQ ID NO 618
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
ugaaaacuca gagaag                                                    16

<210> SEQ ID NO 619
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
cuucucugag uuuucaucca u                                              21

<210> SEQ ID NO 620
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
ugaaaacuca gagaag                                                    16

<210> SEQ ID NO 621
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 621
cuucucugag uuuucaucca u                                              21

<210> SEQ ID NO 622
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
ugaaaacuca gagaag                                                      16

<210> SEQ ID NO 623
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 623
cuucucugag uuuucaucca u                                                21

<210> SEQ ID NO 624
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624
ugaaaacuca gagaag                                                      16

<210> SEQ ID NO 625
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 625
cuucucugag uuuucaucca u                                                21

<210> SEQ ID NO 626
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
gaaaacucag agaaga                                                      16

<210> SEQ ID NO 627
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 627
ucuucucuga guuuucaucc a                                                21

```
<210> SEQ ID NO 628
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628
gaaaacucag agaaga                                                       16

<210> SEQ ID NO 629
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 629
ucuucucuga guuuucaucc a                                                 21

<210> SEQ ID NO 630
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
gaaaacucag agaaga                                                       16

<210> SEQ ID NO 631
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
ucuucucuga guuuucaucc a                                                 21

<210> SEQ ID NO 632
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 632
gaaaacucag agaaga                                                       16

<210> SEQ ID NO 633
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
ucuucucuga guuuucaucc a                                                 21

<210> SEQ ID NO 634
```

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
aaguguccgc acugua                                                        16

<210> SEQ ID NO 635
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 635
uacagugcgg acacuucggc a                                                  21

<210> SEQ ID NO 636
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
aaguguccgc acugua                                                        16

<210> SEQ ID NO 637
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
uacagugcgg acacuucggc a                                                  21

<210> SEQ ID NO 638
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
aaguguccgc acugua                                                        16

<210> SEQ ID NO 639
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
uacagugcgg acacuucggc a                                                  21

<210> SEQ ID NO 640
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 640
aaguguccgc acugua                                                       16

<210> SEQ ID NO 641
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 641
uacagugcgg acacuucggc a                                                 21

<210> SEQ ID NO 642
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 642
cugaccuccu cucugu                                                       16

<210> SEQ ID NO 643
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 643
acagagagga ggucagccaa g                                                 21

<210> SEQ ID NO 644
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 644
cugaccuccu cucugu                                                       16

<210> SEQ ID NO 645
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 645
acagagagga ggucagccaa g                                                 21

<210> SEQ ID NO 646
<211> LENGTH: 16
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 646
cugaccuccu cucugu                                                         16

<210> SEQ ID NO 647
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 647
acagagagga ggucagccaa g                                                   21

<210> SEQ ID NO 648
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 648
aggaagaagg caaaca                                                         16

<210> SEQ ID NO 649
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 649
uguuugccuu cuuccuggag u                                                   21

<210> SEQ ID NO 650
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650
aggaagaagg caaaca                                                         16

<210> SEQ ID NO 651
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 651
uguuugccuu cuuccuggag u                                                   21

<210> SEQ ID NO 652
<211> LENGTH: 16
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 652
aggaagaagg caaaca                                                         16

<210> SEQ ID NO 653
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 653
uguuugccuu cuuccuggag u                                                   21

<210> SEQ ID NO 654
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 654
gaaaacucag agaaga                                                         16

<210> SEQ ID NO 655
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 655
ucuucucuga guuuucaucc a                                                   21

<210> SEQ ID NO 656
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 656
gaaaacucag agaaga                                                         16

<210> SEQ ID NO 657
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 657
ucuucucuga guuuucaucc a                                                   21

<210> SEQ ID NO 658
<211> LENGTH: 16
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 658
gaaaacucag agaaga                                                       16

<210> SEQ ID NO 659
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 659
ucuucucuga guuuucaucc a                                                 21

<210> SEQ ID NO 660
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 660
cccuuugucu auuacu                                                       16

<210> SEQ ID NO 661
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 661
aguaauagac aaggggucg a                                                  21

<210> SEQ ID NO 662
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 662
cccuuugucu auuacu                                                       16

<210> SEQ ID NO 663
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
aguaauagac aaggggucg a                                                  21

<210> SEQ ID NO 664
<211> LENGTH: 16
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 664
cccuuugucu auuacu                                               16

<210> SEQ ID NO 665
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 665
aguaauagac aaagggguvg a                                         21

<210> SEQ ID NO 666
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 666
aggaagaagg caaaca                                               16

<210> SEQ ID NO 667
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 667
uguuugccuu cuuccugga                                            19

<210> SEQ ID NO 668
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 668
aggaagaagg caaaca                                               16

<210> SEQ ID NO 669
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 669
uguuugccuu cuuccuggag u                                         21

<210> SEQ ID NO 670
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 670
aggaagaagg caaaca                                                    16

<210> SEQ ID NO 671
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 671
uguuugccuu cuuccugga                                                 19

<210> SEQ ID NO 672
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 672
cugaccuccu cucugu                                                    16

<210> SEQ ID NO 673
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 673
acagagagga ggucagcca                                                 19

<210> SEQ ID NO 674
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 674
cugaccuccu cucugu                                                    16

<210> SEQ ID NO 675
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 675
acagagagga ggucagccaa g                                              21

<210> SEQ ID NO 676
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 676
cugaccuccu cucugu                                                16

<210> SEQ ID NO 677
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 677
acagagagga ggucagcca                                             19

<210> SEQ ID NO 678
<211> LENGTH: 3710
<212> TYPE: DNA
<213> ORGANISM: Homo sapiens

<400> SEQUENCE: 678
gggtctccgc gcccaggaaa gccccgcgcg gcgcgggcca gggaagggcc acccagggg       60 ccccccacttc ccgcttgggc gcccggacgg cgaatggagc aggggcgcgc agataattaa   120
agatttacac acagctggaa gaaatcatag agaagccggg cgtggtggct catgcctata   180
atcccagcac ttttggaggc tgaggcgggc agatcacttg agatcaggag ttcgagacca   240
gcctggtgcc ttggcatctc ccaatggggt ggctttgctc tgggctcctg ttccctgtga   300
gctgcctggt cctgctgcag gtggcaagct ctgggaacat gaaggtcttg caggagccca   360
cctgcgtctc cgactacatg agcatctcta cttgcgagtg gaagatgaat ggtcccacca   420
attgcagcac cgagctccgc ctgttgtacc agctggtttt tctgctctcc gaagcccaca   480
cgtgtatccc tgagaacaac ggaggcgcgg ggtgcgtgtg ccacctgctc atggatgacg   540
tggtcagtgc ggataactat acactggacc tgtgggctgg gcagcagctg ctgtggaagg   600
gctccttcaa gcccagcgag catgtgaaac ccagggcccc aggaaacctg acagttcaca   660
ccaatgtctc cgacactctg ctgctgacct ggagcaaccc gtatcccct gacaattacc    720 tgtataatca tctcacctat gcagtcaaca tttggagtga aaacgacccg gcagatttca   780
gaatctataa cgtgacctac ctagaaccct ccctccgcat cgcagccagc acctgaagt    840 ctgggatttc ctacagggca cgggtgaggg cctgggctca gtgctataac cacctggga   900 gtgagtggag ccccagcacc aagtggcaca actcctacag ggagcccttc gagcagcacc   960
tcctgctggg cgtcagcgtt tcctgcattg tcatcctggc cgtctgcctg ttgtgctatg  1020
tcagcatcac caagattaag aaagaatggt gggatcagat tcccaaccca gcccgcagcc  1080
gcctcgtggc tataataatc caggatgctc aggggtcaca gtgggagaag cggtcccgag  1140
gccaggaacc agccaagtgc ccacactgga agaattgtct taccaagctc ttgccctgtt  1200
ttctggagca acatgaaa agggatgaag atcctcacaa ggctgccaaa gagatgcctt    1260
tccagggctc tggaaaatca gcatggtgcc cagtggagat cagcaagaca gtcctctggc  1320
cagagagcat cagcgtggtg cgatgtgtgg agttgtttga ggccccggtg gagtgtgagg  1380
aggaggagga ggtagaggaa gaaaaaggga gcttctgtgc atcgcctgag agcagcaggg  1440
atgacttcca ggagggaagg gagggcattg tggcccggct aacagagagc ctgttcctgg  1500
acctgctcgg agaggagaat gggggctttt gccagcagga catgggggag tcatgccttc  1560
ttccaccttc gggaagtacg agtgctcaca tgccctggga tgagttccca agtgcagggc  1620
```

| | |
|---|---|
| ccaaggaggc acctccctgg ggcaaggagc agcctctcca cctggagcca agtcctcctg | 1680 |
| ccagcccgac ccagagtcca gacaacctga cttgcacaga gacgcccctc gtcatcgcag | 1740 |
| gcaaccctgc ttaccgcagc ttcagcaact ccctgagcca gtcaccgtgt cccagagagc | 1800 |
| tgggtccaga cccactgctg gccagacacc tggaggaagt agaacccgag atgccctgtg | 1860 |
| tcccccagct ctctgagcca accactgtgc cccaacctga gccagaaacc tgggagcaga | 1920 |
| tcctccgccg aaatgtcctc cagcatgggg cagctgcagc ccccgtctcg gcccccacca | 1980 |
| gtggctatca ggagtttgta catgcggtgg agcagggtgg cacccaggcc agtgcggtgg | 2040 |
| tgggcttggg tccccaggga gaggctggtt acaaggcctt ctcaagcctg cttgccagca | 2100 |
| gtgctgtgtc cccagagaaa tgtgggtttg ggctagcag tggggaagag gggtataagc | 2160 |
| ctttccaaga cctcattcct ggctgccctg ggaccctgc cccagtccct gtcccccttgt | 2220 |
| tcacctttgg actggacagg gagccacctc gcagtccgca gagctcacat ctcccaagca | 2280 |
| gctccccaga gcacctgggt ctggagccgg gggaaaaggt agaggacatg ccaaagcccc | 2340 |
| cacttcccca ggagcaggcc acagaccccc ttgtggacag cctgggcagt ggcattgtct | 2400 |
| actcagccct tacctgccac ctgtgcggcc acctgaaaca gtgtcatggc caggaggatg | 2460 |
| gtggccagac ccctgtcatg gccagtcctt gctgtggctg ctgctgtgga gacaggtcct | 2520 |
| cgcccctac aacccccctg agggccccag accctctcc aggtgggggtt ccactggagg | 2580 |
| ccagtctgtg tccggcctcc ctggcaccct cgggcatctc agagaagagt aaatcctcat | 2640 |
| catccttcca tcctgccccct ggcaatgctc agagctcaag ccagaccccc aaaatcgtga | 2700 |
| actttgtctc cgtgggaccc acatacatga gggtctctta ggtgcatgtc ctcttgttgc | 2760 |
| tgagtctgca gatgaggact agggcttatc catgcctggg aaatgccacc tcctggaagg | 2820 |
| cagccaggct ggcagatttc caaaagactt gaagaaccat ggtatgaagg tgattggccc | 2880 |
| cactgacgtt ggcctaacac tgggctgcag agactggacc ccgcccagca ttgggctggg | 2940 |
| ctcgccacat cccatgagag tagagggcac tgggtcgccg tgcccacgg caggcccctg | 3000 |
| caggaaaact gaggcccttg ggcacctcga cttgtgaacg agttgttggc tgctccctcc | 3060 |
| acagcttctg cagcagactg tccctgttgt aactgcccaa ggcatgtttt gcccaccaga | 3120 |
| tcatggccca cgtggaggcc cacctgcctc tgtctcactg aactagaagc cgagcctaga | 3180 |
| aactaacaca gccatcaagg gaatgacttg ggcggccttg ggaaatcgat gagaaattga | 3240 |
| acttcaggga gggtggtcat tgcctagagg tgctcattca tttaacagag cttccttagg | 3300 |
| ttgatgctgg aggcagaatc ccggctgtca aggggtgttc agttaagggg agcaacagag | 3360 |
| gacatgaaaa attgctatga ctaaagcagg gacaatttgc tgccaaacac ccatgcccag | 3420 |
| ctgtatggct gggggctcct cgtatgcatg gaaccccag aataaatatg ctcagccacc | 3480 |
| ctgtgggccg ggcaatccag acagcaggca taaggcacca gttaccctgc atgttggccc | 3540 |
| agacctcagg tgctagggaa ggcgggaacc ttgggttgag taatgctcgt ctgtgtgttt | 3600 |
| tagtttcatc acctgttatc tgtgtttgct gaggagagtg gaacagaagg ggtggagttt | 3660 |
| tgtataaata aagtttcttt gtctctttaa aaaaaaaaa aaaaaaaaa | 3710 |

<210> SEQ ID NO 679
<211> LENGTH: 5190
<212> TYPE: DNA
<213> ORGANISM: Homo sapiens

<400> SEQUENCE: 679

| | |
|---|---|
| ccagaagttc tccagggctt ccgcagagcg acttttttcgc tgcctgtgag ctgcagcgcg | 60 |

```
ggagagctcg ggctcgcgcg acccccagcg cctggcaggc tgacagcgct ctctcgcccc    120
aggtgcccgc gcgcgtggtg agcagctgca ccaggtggcg tccggggtgg ggtcaatgaa    180
gcgcagcctg aggaagatgt ggcgccctgg agaaaagaag gagccccagg gcgttgtcta    240
tgaggatgtg ccgacgaca cggaggattt caaggaatcg cttaaggtgg tttttgaagg     300
aagtgcatat ggattacaaa actttaataa gcaaagaaa ttaaaaagat gtgacgatat     360
ggacaccttc ttcttgcatt atgctgcagc agaaggccaa attgagctaa tggagaagat    420
caccagagat tcctctttgg aagtgctgca tgaaatggat gattatggaa ataccccctct   480 gcattgtgct gtagaaaaaa accaaattga agcgttaag tttcttctca gcagaggagc     540
aaacccaaat ctccgaaact tcaacatgat ggctcctctc cacatagctg tgcagggcat    600
gaataatgag gtgatgaagg tcttgcttga gcatagaact attgatgtta atttggaagg    660
agaaaatgga aacacagctg tgatcattgc gtgcaccaca aataatagcg aagcattgca    720
gattttgctt aaaaaaggag ctaagccatg taaatcaaat aaatgggat gtttccctat     780 tcaccaagct gcattttcag gttccaaaga atgcatggaa ataatactaa ggtttggtga    840
agagcatggg tacagtagac agttgcacat taactttatg aataatggga aagccacccc    900
tctccacctg gctgtgcaaa atggtgactt ggaaatgatc aaaatgtgcc tggacaatgg    960
tgcacaaata gacccagtgg agaagggaag gtgcacagcc attcattttg ctgccaccca   1020
gggagccact gagattgtta aactgatgat atcgtcctat tctggtagcg tggatattgt   1080
taacacaacc gatggatgtc atgagaccat gcttcacaga gcttcattgt ttgatcacca   1140
tgagctagca gactatttaa tttcagtggg agcagatatt aataagatcg attctgaagg   1200
acgctctcca cttatattag caactgcttc tgcatcttgg aatattgtaa atttgctact   1260
ctctaaaggt gcccaagtag acataaaaga taattttgga cgtaatttc tgcatttaac    1320 tgtacagcaa ccttatggat taaaaaatct gcgacctgaa tttatgcaga tgcaacagat   1380
caaagagctg gtaatggatg aagacaacga tgggtgtact cctctacatt atgcatgtag   1440
acaggggggc cctggttctg taaataacct acttggcttt aatgtgtcca ttcattccaa   1500
aagcaaagat aagaaatcac ctctgcattt tgcagccagt tatgggcgta tcaatacctg   1560
tcagaggctc ctacaagaca taagtgtgatac gaggcttctg aatgaaggtg accttcatgg   1620
aatgactcct ctccatctgg cagcaaagaa tggacatgat aaagtagttc agcttcttct   1680 gaaaaaggt gcattgtttc tcagtgacca caatggctgg acagctttgc atcatgcgtc    1740
catgggcggg tacactcaga ccatgaaggt cattcttgat actaatttga agtgcacaga   1800
tcgcctggat gaagacggga acactgcact tcactttgct gcagggaag gccacgccaa    1860 agccgttgcg cttcttctga ccacaatgc tgacatagtc ctgaacaagc agcaggcctc    1920 cttttttgcac cttgcacttc acaataagag gaaggaggtt gttcttacga tcatcaggag   1980
caaaagatgg gatgaatgtc ttaagatttt cagtcataat tctccaggca ataaatgtcc   2040
aattacagaa atgatagaat acctccctga atgcatgaag gtactttag atttctgcat    2100 gttgcattcc acagaagaca agtcctgccg agactattat atcgagtata atttcaaata   2160
tcttcaatgt ccattagaat tcaccaaaaa aacacctaca caggatgtta tatatgaacc   2220
gcttacagcc ctcaacgcaa tggtacaaaa taaccgcata gagcttctca atcatcctgt   2280
gtgtaaagaa tatttactca tgaaatggtt ggcttatgga tttagagctc atatgatgaa   2340
tttaggatct tactgtcttg gtctcatacc tatgaccatt ctcgttgtca atataaaacc   2400
```

```
aggaatggct ttcaactcaa ctggcatcat caatgaaact agtgatcatt cagaaatact    2460
agataccacg aattcatatc taataaaaac ttgtatgatt ttagtgtttt tatcaagtat    2520
atttgggtat tgcaaagaag cggggcaaat tttccaacag aaaaggaatt attttatgga    2580
tataagcaat gttcttgaat ggattatcta cacgacgggc atcatttttg tgctgccctt    2640
gtttgttgaa ataccagctc atctgcagtg gcaatgtgga gcaattgctg tttacttcta    2700
ttggatgaat tcttattgt atcttcaaag atttgaaaat tgtggaattt ttattgttat     2760
gttggaggta attttgaaaa ctttgttgag gtctacagtt gtatttatct tccttcttct    2820
ggcttttgga ctcagctttt acatcctcct gaatttacag gatcccttca gctctccatt    2880
gctttctata atccagacct tcagcatgat gctaggagat atcaattatc gagagtcctt    2940
cctagaacca tatctgagaa atgaattggc acatccagtt ctgtcctttg cacaacttgt    3000
ttccttcaca atatttgtcc caattgtcct catgaattta cttattggtt tggcagttgg    3060
cgacattgct gaggtccaga acatgcatc attgaagagg atagctatgc aggtggaact     3120
tcataccagc ttagagaaga agctgccact ttggtttcta cgcaaagtgg atcagaaatc    3180
caccatcgtg tatcccaaca aacccagatc tggtgggatg ttattccata tattctgttt    3240
tttattttgc actggggaaa taagacaaga aataccaaat gctgataaat ctttagaaat    3300
ggaaatatta aagcagaaat accggctgaa ggatcttact tttctcctgg aaaaacagca    3360
tgagctcatt aaactgatca ttcagaagat ggagatcatc tctgagacag aggatgatga    3420
tagccattgt tcttttcaag acaggtttaa gaaagagcag atggaacaaa ggaatagcag    3480
atggaatact gtgttgagag cagtcaaggc aaaaacacac catcttgagc cttagctcct    3540
cagaccttca gtgaggcttc taatgggggg tgcatgactt gctggttcta actttcaatt    3600 taaaagagt gaggaagaag cagaatgatt cattttgctg cgtgtgaaat catggttcct     3660
gcatgctgta taaagtaaa ccatcttta tcctctattc atattttcta ccaatcacta      3720
tgtattgggg atatctttgc agatatgttc aaattggact ggactttgat gagatataat    3780
ctcattattt gaatgggtag aaaatgaatt tgctagaaca cacatttta atgaaaagaa     3840 gtaataaatg taactattaa gctaaaatgc aaatgtcagt actgaattcc tgcttgttaa    3900
ttacataata tgtgatgctc tagaaaatag tcacaagtat taataatgcc ttagatgata    3960
gtcttaaata ttaggttgag gtctacctaa cctaagctgc ttcctggaaa gcttcatgtt    4020
gaaagaacct atgggtggca ccatgtggac ttttctgtcc ctactgtgat gaatagcccc    4080
acccttcttg ctgtccccaa cacacctgat gtcactttga gccatatagt tgaagtacaa    4140
attaataggc cttatgatat gcacgaattt tactatagat aatatatgtt gtttctggtt    4200
ttgtttgcca atgagcataa taatgtaaa acctatatag tatccctgtg attattgtat     4260
gagcctttgt ttgagatttg aaaacaacat ggctccatca catattccct tttttctttt    4320
gatgtctact caaatcatga attaatcaca tacctcatca ttaatctttt caaggtcctt    4380
ctattgtttt gtctgatttt ctccatcatc ctgattagca tgtttattcc ctcactaccc    4440
ccaggagata ttcactgtaa tgaatatgtc tttggctatg tatgtgtcct tgtgttatgt    4500
tgtacagtgt tgttttgagt ctgttattat ttacacagat gttattatgc tatagcttct    4560
atttctgttt ttgcttctta tttctcttat aattctcact tatttcctat tttttctact    4620
catttctatt tgttactcct ttttactgga catgatgttt acaagataca actgtgttac    4680
tgtattccat ctagtacggg gcctttggtg tggcttacta tttcattgtg tgcacccacc    4740
cacccaccac actggacttt tctagagatg gacagcttgg ttacctccac cttcctgcac    4800
```

-continued

| | |
|---|---|
| tcattctcaa acatactgat gttcatacaa accagcagag tgctgaggga cgatatgtac | 4860 |
| tattacaaaa ccagacactt ttacattcat ggtccaacag atcacatggc ctagaggcaa | 4920 |
| tgttgcatat accttaatct tgatatgaa taatatcttt gttctttata tttcttaaaa | 4980 |
| cagaaagggt ggaaaatcac tatacagaag caatatccaa agatctcctg atcataaaga | 5040 |
| caaggggtct tttcagtctt ccctctcctc aaaccttgtg tagcattgca caatatagat | 5100 |
| ctcagtcaac attcactgag tgccaagaat gtgagaaaca ctgtaccatg cctgtcatgc | 5160 |
| gaaatattta aataaacaga ttgtcttaca | 5190 |

<210> SEQ ID NO 680
<211> LENGTH: 2883
<212> TYPE: DNA
<213> ORGANISM: Homo sapiens

<400> SEQUENCE: 680

| | |
|---|---|
| acgctgctcc ttcggtttcc ctgaaaccta acccgccctg gggaggcgcg cagcagaggc | 60 |
| tccgattcgg ggcaggtgag aggctgactt tctctcggtg cgtccagtgg agctctgagt | 120 |
| ttcgaatcgg cggcggcgga ttccccgcgc gccggcgtc ggggcttcca ggaggatgcg | 180 |
| gagccccagc gcggcgtggc tgctgggggc cgccatcctg ctagcagcct ctctctcctg | 240 |
| cagtggcacc atccaaggaa ccaatagatc ctctaaagga agaagcctta ttggtaaggt | 300 |
| tgatggcaca tcccacgtca ctggaaaagg agttacagtt gaaacagtct tttctgtgga | 360 |
| tgagttttct gcatctgtcc tcactggaaa actgaccact gtcttccttc caattgtcta | 420 |
| cacaattgtg tttgtggtgg gtttgccaag taacggcatg gccctgtggg tctttctttt | 480 |
| ccgaactaag aagaagcacc ctgctgtgat ttacatggcc aatctggcct tggctgacct | 540 |
| cctctctgtc atctggttcc ccttgaagat tgcctatcac atacatggca caactggat | 600 |
| ttatggggaa gctcttttgta atgtgcttat tggcttttc tatggcaaca tgtactgttc | 660 |
| cattctcttc atgacctgcc tcagtgtgca gaggtattgg gtcatcgtga accccatggg | 720 |
| gcactccagg aagaaggcaa acattgccat tggcatctcc ctggcaatat ggctgctgat | 780 |
| tctgctggtc accatccctt tgtatgtcgt gaagcagacc atcttcattc ctgccctgaa | 840 |
| catcacgacc tgtcatgatg ttttgcctga gcagctcttg gtgggagaca tgttcaatta | 900 |
| cttcctctct ctggccattg gggtcttct gttcccagcc ttcctcacag cctctgccta | 960 |
| tgtgctgatg atcagaatgc tgcgatcttc tgccatggat gaaaactcag agaagaaaag | 1020 |
| gaagagggcc atcaaactca ttgtcactgt cctggccatg tacctgatct gcttcactcc | 1080 |
| tagtaacctt ctgcttgtgg tgcattattt tctgattaag agccagggcc agagccatgt | 1140 |
| ctatgccctg tacattgtag ccctctgcct ctctaccctt aacagctgca tcgacccctt | 1200 |
| tgtctattac tttgtttcac atgatttcag ggatcatgca agaacgctc tcctttgccg | 1260 |
| aagtgtccgc actgtaaagc agatgcaagt atccctcacc tcaaagaaac actccaggaa | 1320 |
| atccagctct tactcttcaa gttcaaccac tgttaagacc tcctattgag ttttccaggt | 1380 |
| cctcagatgg gaattgcaca gtaggatgtg gaacctgttt aatgttatga ggacgtgtct | 1440 |
| gttatttcct aatcaaaaag gtctcaccac ataccatgtg gatgcagcac ctctcaggat | 1500 |
| tgctaggagc tcccctgttt gcatgagaaa agtagtcccc caaattaaca tcagtgtctg | 1560 |
| tttcagaatc tctctactca gatgacccca gaaactgaac caacagaagc agactttca | 1620 |
| gaagatggtg aagacagaaa cccagtaact tgcaaaaagt agacttggtg tgaagactca | 1680 |

```
cttctcagct gaaattatat atatacacat atatatattt tacatctggg atcatgatag    1740
acttgttagg gcttcaaggc cctcagagat gatcagtcca actgaacgac cttacaaatg    1800
aggaaaccaa gataaatgag ctgccagaat caggtttcca atcaacagca gtgagttggg    1860
attggacagt agaatttcaa tgtccagtga gtgaggttct tgtaccactt catcaaaatc    1920
atggatcttg gctgggtgcg gtgcctcatg cctgtaatcc tagcactttg ggaggctgag    1980
gcaggcaatc acttgaggtc aggagttcga gaccagcctg gccatcatgg cgaaacctca    2040
tctctactaa aaatacaaaa gttaaccagg tgtgtggtgc acgtttgtaa tcccagttac    2100
tcaggaggct gaggcacaag aattgagtat cactttaact caggaggcag aggttgcagt    2160
gagccgagat tgcaccactg cactccagct tgggtgataa aataaaataa aatagtcgtg    2220
aatcttgttc aaaatgcaga ttcctcagat tcaataatga gagctcagac tgggaacagg    2280
gcccaggaat ctgtgtggta caaacctgca tggtgtttat gcacacagag atttgagaac    2340
cattgttctg aatgctgctt ccatttgaca aagtgccgtg ataattttg aaaagagaag     2400 caaacaatgg tgtctctttt atgttcagct tataatgaaa tctgtttgtt gacttattag    2460
gactttgaat tatttcttta ttaaccctct gagtttttgt atgtattatt attaaagaaa    2520
aatgcaatca ggattttaaa catgtaaata caaattttgt ataacttttg atgacttcag    2580
tgaaattttc aggtagtctg agtaatagat tgttttgcca cttagaatag catttgccac    2640
ttagtatttt aaaaaataat tgttggagta tttattgtca gttttgttca cttgttatct    2700
aatacaaaat tataaagcct tcagagggtt tggaccacat ctctttggaa aatagtttgc    2760
aacatattta agagatactt gatgccaaaa tgactttata caacgattgt atttgtgact    2820
tttaaaaata attattttat tgtgtaattg atttataaat aacaaaattt tttttacaac    2880
tta                                                                  2883
```